US007252968B2

(12) United States Patent
Jenuwein et al.

(10) Patent No.: US 7,252,968 B2
(45) Date of Patent: Aug. 7, 2007

(54) CHROMATIN REGULATOR GENES

(75) Inventors: Thomas Jenuwein, Vienna (AT); Götz Laible, Hamilton (NZ); Donal O'Carroll, Greystones (IE); Frank Eisenhaber, Vienna (AT); Stephen Rea, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 408 days.

(21) Appl. No.: 10/773,302

(22) Filed: Feb. 9, 2004

(65) Prior Publication Data

US 2005/0089880 A1 Apr. 28, 2005

Related U.S. Application Data

(60) Division of application No. 09/589,892, filed on Jun. 9, 2000, now Pat. No. 6,689,583, and a continuation-in-part of application No. 08/945,988, filed as application No. PCT/EP96/01818 on Nov. 10, 1997, now abandoned.

(30) Foreign Application Priority Data

May 10, 1995 (DE) .............................. 195 16 776

(51) Int. Cl.
*C12P 21/02* (2006.01)
*C12N 15/00* (2006.01)
*C12N 15/12* (2006.01)
(52) U.S. Cl. ............... 435/69.1; 435/320.1; 435/252.3; 435/325; 536/23.5
(58) Field of Classification Search ..................... None
See application file for complete search history.

(56) References Cited

U.S. PATENT DOCUMENTS

| 5,972,608 A | 10/1999 | Peterson et al. ............... 435/6 |
| 6,555,329 B2 | 4/2003 | Jenuwein et al. ............. 435/15 |
| 6,689,583 B1 | 2/2004 | Jenuwein et al. .......... 435/69.1 |
| 2002/0039776 A1 | 4/2002 | Jenuwein et al. ........... 435/193 |
| 2002/0164620 A1 | 11/2002 | Peters et al. .................... 435/6 |
| 2003/0087368 A1 | 5/2003 | Maupin-Furlow et al. . 435/69.1 |
| 2003/0104599 A1 | 6/2003 | Jenuwein et al. ........... 435/193 |
| 2003/0157532 A1 | 8/2003 | Jenuwein et al. ............... 435/6 |

FOREIGN PATENT DOCUMENTS

| DE | 195 16 776 | 11/1996 |
| EP | 1 227 160 A1 | 7/2002 |
| WO | WO 95/15749 | 6/1995 |
| WO | WO 98/27994 | 7/1998 |
| WO | WO 98/49190 | 11/1998 |
| WO | WO 00/48627 | 8/2000 |

OTHER PUBLICATIONS

Aagaard, L., et al., "Functional mammalian homologues of the Drosophila PEV-modifier Su(var)3-9 encode centromere-associated proteins which complex with the heterochromatin component M31," *EMBO J.* 18:1923-1938, Oxford University Press (Apr. 1999).

Aagaard, L., et al., "Mitotic phosphorylation of SUV39H1, a novel component of active centromeres, coincides with transient accumulation at mammalian centromeres," *J. Cell Sci.* 113:817-829, The Company of Biologists Ltd. (Mar. 2000; Published on the WWW on Feb. 14, 2000).

Aasland, R. and Stewart, A.F., "The chromo shadow domain, a second chromo domain in heterochromatin-binding protein 1, HP1," *Nucleic Acids Res.* 23:3168-3173, Oxford University Press (Aug. 1995).

Adams, B., et al., "Pax-5 encodes the transcription factor BSAP and is expressed in B lymphocytes, the developing CNS, and adult testis," *Genes & Dev.* 6:1589-1607, Cold Spring Harbor Laboratory Press (1992).

Adams, R.R., et al., "INCENP binds the Aurora-related kinase AIRK2 and is required to target it to chromosomes, the central spindle and cleavage furrow," *Curr. Biol.* 10:1075-1078, Elsevier Science. Ltd. (Sep. 2000).

Ainsztein, A.M., et al., "INCENP Centromere and Spindle Targeting: Identification of Essential Conserved Motifs and Involvement of Heterochromatin Protein HP1," *J. Cell Biol.* 143:1763-1774, The Rockefeller University Press (Dec. 1998).

Alkema, M.J., et al., "Transformation of axial skeleton due to overexpression of*bmi*-1 in transgenic mice," *Nature* 374:724-727, Nature Publishing Group (Apr. 1995).

Allshire, R.C., et al., "Mutations derepressing silent centromeric domains in fission yeast disrupt chromosome segregation," *Genes & Dev.* 9:218-233, Cold Spring Harbor Laboratory Press (Jan. 1995).

Altschul, S.F., et al., "Gapped BLAST and PSI-BLAST: a new generation of protein database search programs," *Nucl. Acids Res.* 25:3389-3402, Oxford University Press (Sep. 1997).

Ambrose, W.P., et al., "Detection System for Reaction-Rate Analysis in a Low-Volume Proteinase-Inhibition Assay," *Anal. Biochem.* 263:150-157, Academic Press (1998).

Baksa, K., et al., "Mutations in the Protein Phosphatase 1 Gene at 87B Can Differentially Affect Suppression of Position-Effect Variegation and Mitosis in *Drosophila melanogaster,*" *Genet.* 135:117-125, The Genetics Society of America (1993).

Ball, L.J., et al. , "Structure of the chromatin binding (chromo) domain from mouse modifier protein 1," *EMBO J.* 16:2473-2481, Oxford University Press (May 1997).

Bannister, A.J., et al., "Selective recognition of methylated lysine 9 on histone H3 by the HP1 chromo domain," *Nature* 410:120-124, Nature Publishing Group (Mar. 2001).

Barrett, A.J. and Kirschke, H., "Cathepsin B, Cathepsin H, and Cathepsin L," *Methods Enzym.* 80:535-561, Academic Press (1981).

Bassett, D.E., Jr., et al., "Comparative genomics, genome cross-referencing and XREFdb," *Trends Genet.* 11:372-373, Elsevier Science Ltd. (Sep. 1995).

(Continued)

*Primary Examiner*—James Martinell
(74) *Attorney, Agent, or Firm*—Sterne, Kessler, Goldstein & Fox PLLC

(57) ABSTRACT

The invention concerns the deregulation of the chromatin-regulator genes which have a SET domain, such deregulation being of importance in certain cancer conditions. These genes can be used in the diagnosis and therapy of such conditions.

13 Claims, 16 Drawing Sheets

OTHER PUBLICATIONS

Baudat, F., et al., "Chromosome Synapsis Defects and Sexually Dimorphic Meiotic Progression in Mice Lacking Spo11" *Mol. Cell.* 6:989-998, Cell Press (Nov. 2000).

Bernard, P., et al., "Fission Yeast Bub1 is a Mitotic Centromere Protein Essential for the Spindle Checkpoint and the Preservation of Correct Ploidy through Mitosis," *J. Cell Biol.* 143:1775-1787, The Rockefeller University Press (Dec. 1998).

Boulianne, G.L., et al., "Production of functional chimaeric mouse/human antibody," *Nature* 312:643-646, Macmillan Magazines Ltd. (1984).

Brown, A.M., et al., "Biotinylated and Cysteine-Modified Peptides as Useful Reagents for Studying the Inhibition of Cathepsin G," *Anal. Biochem.* 217:139-147, Academic Press, Inc. (Feb. 1994).

Brunk, B.P., et al., "Drosophila genes *Posterior Sex Combs* and *Suppressor two of zeste* encode proteins with homology to the murine *bmi*-1 oncogene," *Nature* 353:351-353, Nature Publishing Group (1991).

Buck, S.W, and Shore, D., "Action of a RAP1 carboxy-terminal silencing domain reveals an underlying competition between *HMR* and telomeres in yeast," *Genes & Dev.* 9:370-384, Cold Spring Harbor Laboratory Press (Feb. 1995).

Bunick, D., et al., "Transcription of the testis-specific mouse protamine 2 gene in a homologous *in vitro* transcription system, " *Proc. Natl. Acad. Sci. USA*, 87: 891-895, National Academy of Sciences (1990).

Buonomo, S.B.C., et al., "Disjunction of Homologous Chromosomes in Meiosis I Depends on Proteolytic Cleavage of the Meiotic Cohesin Rec8 by Separin," *Cell* 103:387-398, Cell Press (Oct. 2000).

Burgoyne, P.S., "Genetic Homology and Crossing Over in the X and Y Chromosomes of Mammals," *Hum. Genet.* 61:85-90, Springer-Verlag (1982).

Cai, J. et al., "Reconstitution of human replication factor C from its five subunits in baculovirus-infected insect cells," *Proc. Natl. Acad. Sci. USA* 93:12896-12901, National Academy of Sciences (Nov. 1996).

Calenda, A., et al., "The meiosis-specific *Xmr* gene product is homologous to the lymphocyte Xlr protein and is a component of the XY body," *EMBO J.* 13:100-109, Oxford University Press (Jan. 1994).

Cerretani, M., et al., "A High-Throughput Radiometric Assay for Hepatitis C Virus NS3 Protease," *Anal. Biochem.* 266:192-197, Academic Press (Jan. 1999).

Chen, D., et al., "Regulation of Transcription by a Protein Methyltransferase," *Science* 284:2174-2177, American Association for the Advancement of Science (Jun. 1999).

Ciosk, R., et al., "An ESP1/PDS1 Complex Regulates Loss of Sister Chromatid Cohesion at the Metaphase to Anaphase Transition in Yeast," *Cell* 93:1067-1076, Cell Press (Jun. 1998).

Clark, D.A., et al., "Protease Inhibitors Suppress In Vitro Growth of Human Small Cell Lung Cancer," *Peptides* 14:1021-1028, Pergamon Press, Ltd. (1993).

Cléard, F. et al., "SU(VAR) 3-7, a *Drosophila* heterochromatin-associated protein and companion of HP1 in the genomic silencing of position-effect variegation," *The EMBO Journal* 16:5280-5288, Oxford University Press (Sep. 1997).

Cobb, J., et al., "Meiotic events at the centromeric heterochromatin: histone H3 phosphorylation, topoisomerase IIa localization and chromosome condensation," *Chromosoma* 108:412-425, Springer-Verlag (Dec. 1999).

Cohen-Fix, O. et al., "Anaphase initiation in *Saccharomyces cerevisiae* is controlled by the APC-dependent degradation of the anaphase inhibitor Pds1p," *Genes & Dev.* 10:3081-3093, Cold Spring Harbor Laboratory Press (Dec. 1996).

Cortez, D. and Elledge, S.J., "Conducting the mitotic symphony," *Nature* 406:354-356, Nature Publishing Group (Jul. 2000).

Csink, A. and Henikoff, S., "Genetic modification of heterochromatic association and nuclear organization in *Drosophila*," *Nature* 381:529-531, Nature Publishing Group (Jun. 1996).

Cutts, S.M., et al., "Defective chromosome segregation, microtubule bundling and nuclear bridging in inner centromere protein gene (*Incenp* )-disrupted mice," *Hum. Mol. Genet.* 8:1145-1155, Oxford University Press (Jul. 1999).

Czvitkovich, S., et al., "Over-expression of the SUV39H1 histone methyltransferase induces altered proliferation and differentiation in transgenic mice," *Mech. Dev.* 107:141-153, Elsevier Science Ireland Ltd. (Sep. 2001).

DeCamillis, M., et al., "The *Polyhomeotic* gene of *Drosophila* encodes a chromatin protein that shares polytene chromosome-binding sites with *Polycomb,* " *Genes & Dev.* 6:223-232, Cold Spring Harbor Laboratory Press (1992).

Dernburg, A.F., et al., "Perturbation of Nuclear Architecture by Long-Distance Chromosome Interactions," *Cell* 85:745-759, Cell Press (May 1996).

Dernburg, A.F., et al., "Direct Evidence of a Role for Heterochromatin in Meiotic Chromosome Segregation," *Cell* 86:135-146, Cell Press (Jul. 1996).

De Rubertis, F. et al., "The histone deacetylase RPD3 counteracts genomic silencing in *Drosophila* and yeast," *Nature* 384:589-591, Nature Publishing Group (Dec. 1996).

de Vries, S.S., et al., "Mouse MutS-like protein Msh5 is required for proper chromosome synapsis in male and female meiosis," *Genes & Dev.* 13:523-531, Cold Spring Harbor Laboratory Press (Mar. 1999).

Dominguez, A., et al., "*hpttg*, a human homologue of rat *pttg*, is overexpressed in hematopoietic neoplasms. Evidence for a transcriptional activation function of hPTTG," *Oncogene* 17:2187-2193, Nature Publishing Group (Oct 1998).

Dougherty, W., et al., "Molecular Genetic Analysis of a Plant Virus Polyprotein Cleavage Site: A Model," *Virology* 171:356-364, Academic Press (1989).

Dugaiczyk, A., et al., "Cloning and Sequencing of a Deoxyribonucleic Acid Copy of Glyceraldehyde-3-phosphate Dehydrogenase Messenger Ribonucleic.Acid Isolated from Chicken Muscle," *Biochemistry* 22:1605-1613, American Chemical Society (1983).

Eissenberg, J.C., et al., "The Heterochromatin-Associated Protein HP-1 Is an Essential Protein in Drosophila With Dosage-Dependent Effects on Position-Effect Variegation," *Genetics* 131:345-352, Genetics Society of America (1992).

Ekwall, K., et al., "Mutations in the fission yeast silencing factors *clr* 4+ and *rik* 1+ disrupt the localisation of the chromo domain protein Swi6p and impair centromere function," *J. Cell Sci.* 109:2637-2648, The Company of Biologists Limited (Nov. 1996).

Ekwall, K., et al., "Transient Inhibition of Histone Deacetylation Alters the Structural and Functional Imprint at Fission Yeast Centromeres," *Cell* 91:1021-1032, Cell Press (Dec. 1997).

Elbashir, S.M., et al., "Duplexes of 21-nucleotide RNAs mediate RNA interference in cultured mammalian cells," *Nature* 411:494-498, Nature Publishing Company (May 2001).

Epstein, C.B., and Cross, F.R. "*CLB5*: a novel B cyclin from budding yeast with a role in S phase," *Genes & Dev.* 6:1695-1706, Cold Spring Harbor laboratory Press (1992).

Faleiro, L., et al., "Multiple species of CPP32 and Mch2 are the major active caspases present in apoptotic cells," *EMBO J.* 16:2271-2281, Oxford University Press (May 1997).

Foon, K.A., and Gale, R.P. "Chronic Lymphoid Leukemias," in: *Blood : Principles and Practice of Hematology*, Handin, R.I., et al., eds., J.B. Lippincott Company, Philadelphia, PA, pp. 783-811 (Jan. 1995).

Friedman, L.S., et al., "The Search for *BRCA1,*" *Cancer Res.* 54:6374-6382, American Association for Cancer Research (Dec. 1994).

Friedman, L.S., et al., "22 Genes from Chromosome 17q21: Cloning, Sequencing, and Characterization of Mutations in Breast Cancer Families and Tumors," *Genomics* 25:256-263, Academic Press (Jan. 1995).

Funabiki, H., et al., "Cut2 proteolysis required for sister-chromatid separation in fission yeast," *Nature* 381:438-441, Nature Publishing Company (May 1996).

Garzino, V., et al., "Cell lineage-specific expression of *modulo*, a dose-dependent modifier of variegation in *Drosophila*," *EMBO J. 11*:4471-4479, Oxford University Press (1992).

Gentz, R., et al., "Bioassay for trans-activation using purified human immunodeficiency virus *tat*-encoded protein: Trans-activation requires mRNA synthesis," *Proc. Natl. Acad. Sci. USA 86*:821-824, National Academy of Sciences (1989).

Geraghty, M.T., et al., "The Isolation of cDNAs from OATL1 at Xp11.2 Using a 480-kb YAC," *Genomics 16*:440-446, Academic Press, Inc. (1993).

Gershkovich, A.A. and Kholodovych, V.V., "Fluorogenic substrates for proteases based on intramolecular fluorescence energy transfer (IFETS)," *J. Biochem. Biophys. Methods 33*:135-162, Elsevier Science B.V. (Dec. 1996).

Gibbons, R.J., et al., "Mutations in a Putative Global Transcriptional Regulator Cause X-Linked Mental Retardation with α-Thalassemia (ATR-X Syndrome)," *Cell 80*:837-845, Cell Press (Mar. 1995).

Gietz, R.D. and Sugino, A., "New Yeast-*Escherichia coli* shuttle vectors constructed with in vitro mutagenized yeast genes lacking six-base pair restriction sites," *Gene 74*:527-534, Elsevier Science Publishers B.V. (1988).

Gmachl, M., et al., "The RING-H2 finger protein APC11 and the E2 enzyme UBC4 are sufficient to ubiquitinate substrates of the anaphase-promoting complex," *Proc. Natl. Acad. Sci. USA 97*:8973-8978, National Academy of Sciences (Aug. 2000).

Gray, N.M., et al., "Discovery and Analysis of a Series of $C_2$-Symmetric HIV-1 Proteinase Inhibitors Derived from Penicillin," *Anal. Biochem. 216*:89-96, Academic Press (Jan. 1994).

Graziano, R.F., et al., "Construction and Characterization of a Humanized Anti-γ-lg Receptor Type I (FcγRI) Monoclonal Antibody," *J. Immunol. 155*: 4996-5002, American Association of Immunologists (Nov. 1995).

Griffin, D.K., et al., "Sex Ratio in Normal and Disomic Sperm: Evidence That the Extra Chromosome 21 Preferentially Segregates with Y Chromosome," *Am. J. Hum. Genet. 59*:1108-1113, The University of Chicago Press (Nov. 1996).

Grunstein, M., "Yeast Heterochromatin: Regulation of Its Assembly and Inheritance by Histones," *Cell 93*:325-328, Cell Press (May 1998).

Gu, Y., et al., "The t(4;11) Chromosome Translocation of Human Acute Leukemias Fuses the *ALL-1* Gene, Related to Drosophila *trithorax*, to the *AF-4* Gene," *Cell 71*:701-708, Cell Press (1992).

Handel, M.A. and Hunt, P.A., "Sex-Chromosome Pairing and Activity during Mammalian Meiosis," *Bioessays 14*:817-22, John Wiley and Sons, Inc. (1992).

Hauf, S., et al., "Cohesion Cleavage by Separase Required for Anaphase and Cytokinesis in Human Cells," *Science 293*:1320-1323. The American Association for the Advancement of Science (Aug. 2001).

Haupt, Y., et al., "Novel Zinc Finger Gene Implicated as *myc* Collaborator by Retrovirally Accelerated Lymphomagenesis in Eμ-*myc* Transgenic Mice," *Cell 65*:753-763, Cell Press (1991).

Hawley, R.S., et al., "There are Two Mechanisms of Achiasmate Segregation in *Drosophila* Females, One of Which Requires Heterochromatic Homology," *Dev. Genet. 13*:440-467, Wiley-Liss, Inc. (1993).

Hayden, J.H., et al., "Kinetochores Capture Astral Microtubules During Chromosome Attachment to the Mitotic Spindle: Direct Visualization in Live Newt Lung Cells," *J. Cell Biol. 111*:1039-1045, The Rockefeller University Press (1990).

Hendzel, M.J., et al., "Mitosis-specific phosphorylation of histone H3 initiates primarily within pericentromeric heterochromatin during G2 and spreads in an ordered fashion coincident with mitotic chromosome condensation," *Chromosoma 106*:348-360, Springer-Verlag (Nov. 1997).

Henikoff, S., "Position-effect Variegation in *Drosophila*: Recent Progress," in *Epigenetic Mechanisms of Gene Regulation*, Russo, V.E.A., et al., eds., Cold Spring Harbor Laboratory Press, Plainview, New York, pp. 319-334 (Dec. 1996).

Hobert, O., et al., "Interaction of Vav with ENX-1, a Putative Transcriptional Regulator of Homeobox Gene Expression," *Mol. Cell. Biol. 16*:3066-3073, American Society for Microbiology (Jun. 1996).

Hsu, J.Y., et al., "Mitotic Phosphorylation of Histone H3 is Governed by Ipl1/aurora Kinase and Glc7/PP1 Phosphatase in Budding Yeast and Nematodes," *Cell 102*:279-291, Cell Press (Aug. 2000).

Ivanova, A.V., et al., "The chromo and SET domains of the Clr4 protein are essential for silencing in fission yeast," *Nat. Genet. 19*:192-195, Nature Publishing Company (Jun. 1998).

Jacobson, S. and Pillus, L., "Modifying chromatin and concepts of cancer," *Curr. Opin. Genet. Dev. 9*:175-184, Current Biology Publications (Apr. 1999).

Jenuwein, T., et al., "SET domain proteins modulate chromatin domains in eu- and heterochromatin," *Cell Mol. Life Sci. 54*:80-93, Birkhäuser Verlag (Jan. 1998).

Jenuwein, T., "Re-SET-ting heterochromatin by histone methyltransferases," *Trends Cell Biol. 11*:266-273, Elsevier Science Ltd. (Jun. 2001).

Jolley, M.E., "Fluorescence Polarization Assays for the Detection of Proteases and Their Inhibitors," *J. Biomol. Scr. 1*:33-38, Mary Ann Liebert, Inc. (Spring 1996).

Jones, D.O., et al., "Mammalian chromodomain proteins: their role in genome organisation and expression," *Bioessays 22*:124-137, John Wiley and Sons, Inc. (Feb. 2000).

Jones, R.S., and Gelbart, W.M., "The *Drosophila* Polycomb-Group Gene *Enhancer of zeste* Contains a Region with Sequence Similarity to *trithorax*," *Mol. Cell Biol. 13*:6357-6366, American Society for Microbiology (1993).

Kaitna, S., et al., "Incenp and an Aurora-like kinase form a complex essential for chromosome segregation and efficient completion of cytokinesis," *Curr. Biol. 10*:1172-1181, Elsevier Science Ltd. (Sep. 2000).

Karpen, G. H., et al., "Centric Heterochromatin and the Efficiency of Achiasmate Disjunction in *Drosophila* Female Meiosis," *Science 273*:118-122, American Association for the Advancement of Science (Jul. 1996).

Karpen, G.H. and Allshire, R.C., "The case for epigenetic effects on centromere identity and function," *Trends Genet. 13*:489-496, Elsevier Science Ltd. (Dec. 1997).

Kerrebrock, A.W., et al., "Mei-S332, a Drosophila Protein Required for Sister-Chromatid Cohesion, Can Localize to Meiotic Centromere Regions," *Cell 83*:247-256, Cell Press (Oct. 1995).

Klein, F., et al., "A Central Role for Cohesins in Sister Chromatid Cohesion, Formation of Axial Elements, and Recombination during Yeast Meiosis," *Cell 98*:91-103, Cell Press (Jul. 1999).

Klein, R.R. and Houtz, R.L., "Cloning and developmental expression of pea ribulose-1,5-bisphosphate carboxylase/oxygenase large subunit N-methyltransferase," *Plant Mol. Biol. 27*:249-261, Kluwer Academic Publishers (Jan. 1995).

Köhler, G. and Milstein, C., "Continuous cultures of fused cells secreting antibody of predefined specificity," *Nature 256*:495-497, Nature Publishing Company (1975).

Koonin, E.V., et al., "The chromo superfamily: new members, duplication of the chromo domain and possible role in delivering transcription regulators to chromatin," *Nucl. Acids Res. 23*:4229-4233, Oxford University Press (Nov. 1995).

Kot, M.C. and Handel, M.A. "Spermatogenesis in XO,*Sxr* Mice: Role of the Y Chromosome," *J. Exp. Zool. 256*:92-105, Wiley-Liss, Inc. (1990).

Kramer, E.R., et al., "Activation of the human anaphase-promoting complex by proteins of the CDC20/Fizzy family," *Curr. Biol. 8*:1207-1210, Current Biology Ltd. (Oct. 1998).

Lachner, M., et al., "Methylation of histone H3 lysine 9 creates a binding site for HP1 proteins," *Nature 410*:116-120, Nature Publishing Group (Mar. 2001).

Laible, G., et al., "Mammalian homologues of the *Polycomb*-group gene *Enhancer of zeste* mediate gene silencing in *Drosophila* heterochromatin and at *S. cerevisiae* telomeres," *EMBO J. 16*:3219-3232, Oxford University Press (Jun. 1997).

Lamb, D.J. and Niederberger, C.S. "Animal Models that Mimic Human Male Reproductive Defects," *Urol. Clin. North Am. 21*:377-387, W.B. Saunders Co. (Aug. 1994).

Lammers, J.H.M., et al., "The Gene Encoding a Major Component of the Lateral Elements of Synaptonemal Complexes of the Rat Is Related to X-Linked Lymphocyte-Regulated Genes," *Mol. Cell. Biol.* 14:1137-1146, American Society for Microbiology (Feb. 1994).

Lammers, J.H.M., et al., "A change in the phosphorylation pattern of the 30,000-33,000 $M_r$ synaptonemal complex proteins of the rat between early and mid-pachytene," *Chromosoma* 104:154-163, Springer-Verlag (Nov. 1995).

Larsson, J., et al., "Mutations in the *Drosophila melanogaster* Gene Encoding S-adenosylmethionine Suppress Position-Effect Variegation," *Genetics* 143:887-896, The Genetics Society of America (Jun. 1996).

Lee, I.A., et al., "Cloning and Expression of Human cDNA Encoding Human Homologue of Pituitary Tumor Transforming Gene," *Biochem. Mol. Biol. Intl.* 47:891-897, Taylor & Francis (May 1999).

Lengauer, C., et al., "Genetic instability in colorectal cancers," *Nature* 386:623-627, Nature Publishing Group (Apr. 1997).

Levine, L.M., et al., "Measurement of Specific Protease Activity Utilizing Fluorescence Polarization," *Anal. Biochem.* 247:83-88, Academic Press (Apr. 1997).

Lewis, J.D. and Tollervey, D., "Like Attracts Like: Getting RNA Processing Together in the Nucleus," *Science* 288:1385-1389, The American Association for the Advancement of Science (May 2000).

Liang, C. and Stillman, B., "Persistent initiation of DNA replication and chromatin-bound MCM proteins during the cell cycle in *cdc6* mutants," *Genes & Dev.* 11:3375-3386, Cold Spring Harbor Laboratory Press (Dec. 1997).

Lim H.H. et al., "Cdc20 is essential for the cyclosome-mediated proteolysis of both Pds1 and Clb2 during M phase in budding yeast," *Curr. Biol.* 8:231-234, Current Biology Ltd. (Feb. 1998).

Locke, J., et al., "Dosage-Dependent Modifiers of Position Effect Variegation in Drosphila and a Mass Action Model That Explains Their Effect," *Genetics* 120:181-198, Genetics Society of America (1988).

Losada, A., et al., "Identification of *Xenopus* SMC protein complexes required for sister chromatid cohesion," *Genes & Dev.* 12:1986-1997, Cold Spring Harbor Laboratory Press (Jul. 1998).

Martzen, M.R., et al., "A Biochemical Genomics Approach for Identifying Genes by the Activity of Their Products," *Science* 286:1153-1155, American Association for the Advancement of Science (Nov. 1999).

Matayoshi, E.D., et al., "Novel Fluorogenic Substrates for Assaying Retroviral Proteases by Resonance Energy Transfer," *Science* 247:954-958, The American Association for the Advancement of Science (1990).

Matsuda, Y., et al., "Genetic basis of X-Y chromosome dissociation and male sterility in interspecific hybrids," *Proc. Natl. Acad. Sci. USA* 88:4850-4854, National Academy of Sciences (1991).

McGrew, J.T., et al., "Requirement for *ESP1* in the Nuclear Division of *Saccharomyces cerevisiae*," *Mol. Biol. Cell* 3:1443-1454, American Society for Cell Biology (1992).

McKay, M.J., et al., "Sequence Conservation of the *rad21 Schizosaccharomyces pombe* DNA Double-Strand Break Repair Gene in Human and Mouse," *Genomics* 36:305-315, Academic Press, Inc. (Sep. 1996).

Meistrich, M.L. and Brock, W.A., "Proteins of the Meiotic Cell Nucleus," In *Meiosis*, Moens, P.B., ed., Academic Press, New York, N.Y., pp. 333-353 (1987).

Melcher, M., et al., "Structure-Function Analysis of SUV39H1 Reveals a Dominant Role in Heterochromatin Organization, Chromosome Segregation, and Mitotic Progression," *Mol. Cell. Biol.* 20:3728-3741, American Society for Microbiology (May 2000).

Merdes, A. and De Mey, J., "The mechanism of kinetochore-spindle attachment and polewards movement analyzed in $PtK_2$ cells at the prophase-prometaphase transition," *Eur. J. Cell Biol.* 53:313-325, Wissenschaftliche verlagsgesellschaft mbH (1990).

Messmer, S., et al., "Analysis of the functional role of the *Polycomb* chromo domain in *Drosophila melanogaster*," *Genes & Dev.* 6:1241-1254, Cold Spring Harbor Laboratory Press (1992).

Michaelis, C., et al., "Cohesions: Chromosomal Proteins that Prevent Premature Separation of Sister Chromatids," *Cell* 91:35-45, Cell Press (Oct. 1997).

Milner, C.M., and Campbell, R.D., "The G9a gene in the human major histocompatibility complex encodes a novel protein containing ankyrin-like repeats," *Biochem. J.* 290:811-818, Biochemical Society/Portland Press (1993).

Miyazaki, W.Y. and Orr-Weaver, T.L., "Sister-Chromatid Cohesion in Mitosis and Meiosis," *Annu. Rev. Genet.* 28:167-187, Annual Reviews (Dec. 1994).

Moens, P.B., "Histones H1 and H4 of surface-spread meiotic chromosomes," *Chromosoma* 104:169-174, Springer-Verlag (Nov. 1995).

Moore, D.P., et al., "The Cohesion Protein MEI-S332 Localizes to Condensed Meiotic and Mitotic Centromeres until Sister Chromatids Separate," *J. Cell. Biol.* 140:1003-1012, The Rockefeller University Press (Mar. 1998).

Motzkus, D., et al., "M31, a murine homolog of Drosophila HP1, is concentrated in the XY body during spermatogenesis," *Cytogenet. Cell Genet.* 86:83-88, S. Karger AG (Oct. 1999).

Murray, A.W., "Cell Cycle Extracts," *Meth. Cell Biol.* 36:581-605, Academic Press, Inc. (1991).

Murray, M.G., et al., "Inactivation of a yeast transactivator by the fused HIV-1 proteinase: a simple assay for inhibitors of the viral enzyme activity," *Gene* 134:123-128, Elsevier Science Publishers B.V. (1993).

Nagase, T., et al., "Prediction of the Coding Sequences of Unidentified Human Genes. V. The Coding Sequences of 40 New Genes (KIAA0161-KIAA0200) Deduced by Analysis of cDNA Clones from Human Cell Line KG-1," *DNA Res.* 3:17-24, Kazusa DNA Research Institute and Universal Academy Press, Inc. (Feb. 1996).

Nakayama, J., et al., "Role of Histone H3 Lysine 9 Methylation in Epigenetic Control of Heterochromatin Assembly," *Science* 292:110-113, American Association for the Advancement of Science (Apr. 2001).

Nasmyth, K., et al., "Splitting the Chromosome: Cutting the Ties That Bind Sister Chromatids," *Science* 288:1379-1384, The American Association for the Advancement of Science (May 2000).

Neuberger, M.S., et al., "Recombinant antibodies possessing novel effector functions," *Nature* 312:604-608, Macmillan Magazines Ltd. (1984).

Nicholson, D.W., et al., "Identification and inhibition of the ICE/CED-3 protease necessary for mammalian apoptosis," *Nature* 376:37-43, Nature Publishing Company (Jul. 1995).

O'Carroll, D., et al., "Isolation and Characterization of *Suv39h2*, a Second Histone H3 Methyltransferase Gene That Displays Testis-Specific Expression," *Mol. Cell. Biol.* 20:9423-9433, American Society for Microbiology (Dec. 2000).

Offenberg, H.H., et al., "Tissue distribution of two major components of synaptonemal complexes of the rat," *Chromosoma* 101:83-91, Springer-Verlag (1991).

Orlando V., and Paro, R., "Mapping Polycomb-Repressed Domains in the Bithorax Complex Using In Vivo Formaldehyde Cross-Linked Chromatin," *Cell* 75:1187-1198, Cell Press (1993).

Pandita, T.K., et al., "*Atm* Inactivation Results in Aberrant Telomere Clustering during Meiotic Prophase," *Mol. Cell. Biol.* 19:5096-5105, American Society for Microbiology (Jul. 1999).

Pardue, M.L. and Gall, J.G., "Chromosomal Localization of Mouse Satellite DNA," *Science* 168:1356-1358, American Association for the Advancement of Science (1970).

Park, I.K., et al., "Interrelationship Between Nuclear Histone Binding and Cell Proliferation," *Int. J. Biochem.* 20:183-187, Pergamon Press (1988).

Paro, R. and Harte, P.J., "The Role of Polycomb Group and Trithorax Group Chromatin Complexes in the Maintenance of Determined Cell States," in *Epigenetic Mechanisms of Gene Regulation*, Russo, V.E.A., et al., eds., Cold Spring Harbor Laboratory Press, Plainview, N.Y., pp. 507-528 (Dec. 1996).

Paro, R. and Hogness, D.S. "The Polycomb protein shares a homologous domain with a heterochromatin-associated protein of Drosophila," *Proc. Natl. Acad. Sci. USA* 88:263-267, National Academy of Sciences (1991).

Pehrson, J.R. and Fried, V.A., "MacroH2A, a Core Histone Containing a Large Nonhistone Region," *Science* 257:1398-1400, American Association for the Advancement of Science (1992).

Peters, A.H.F.M., et al., "A drying-down technique for the spreading of mammalian meiocytes from the male and female germline," *Chromosome Res.* 5:66-68, Rapid Science Publishers (Feb. 1997).

Peters, A.H.F.M., et al., "Meiosis in carriers of heteromorphic bivalents: sex differences and implications for male fertility," *Chromosome Res.* 5:313-324, Rapid Science Publishers (Aug. 1997).

Peters, J. -M., "SCF and APC: the Yin and Yang of cell cycle regulated proteolysis," *Curr. Opin. Cell Biol.* 10:759-768, Current Biology Ltd. (Dec. 1998).

Platero, J.S., et al., "Functional analysis of the chromo domain HP1," *EMBO J.* 14:3977-3986, Oxford University Press (Aug. 1995).

Rastelli, L., et al., "Related chromosome binding sites for *zeste*, suppressors of *zeste and Polycomb* group proteins in *Drosophila* and their dependence on *Enhancer of zeste* function, " *EMBO J.* 12:1513-1522, Oxford University Press (1993).

Rea, S., et al., "Regulation of chromatin structure by site-specific histone H3 methyltransferases," *Nature* 406:593-599, Nature Publishing Company (Aug. 2000).

Reuter G., and Spierer, P., "Position Effect Variegation and Chromatin Proteins," *BioEssays* 14:605-612, The Company of Biologists, Ltd. (1992).

Rice, J.C. and Allis, C.D., "Histone methylation versus acetylation: new insights into epigenetic regulation," *Curr. Opin. Cell. Biol.* 13:263-273, Elsevier Science Ltd. (Jun. 2001).

Riechmann, L., et al., "Reshaping human antibodies for therapy," *Nature 332*: 323-327, Macmillan Magazines Ltd. (1988).

Rieder, C.L. and Salmon, E.D., "The vertebrate cell kinetochore and its roles during mitosis," *Trends in Cell Biol.* 8:310-318, Elsevier Science Ltd. (Aug. 1998).

Sarubbi, E., et al., "A high throughput assay for inhibitors of HIV-1 protease. Screening of microbial metabolites," *FEBS* 279:265-269, Elsevier Science Publishers B.V. (1991).

Sassone-Corsi, P., et al., "Requirement for Rsk-2 for Epidermal Growth Factor-Activated Phosphorylation of Histone H3," *Science* 285:886-891, American Association for the Advancement of Science (Aug. 1999).

Scherthan, H., et al., "Centromere and Telomere Movements during Early Meiotic Prophase of Mouse and Man are Associated with the Onset of Chromosome Pairing," *J. Cell Biol.* 134:1109-1125, The Rockefeller University Press (Sep. 1996).

Schotta, G. and Reuter, G., "Controlled expression of tagged proteins in *Drosophila* using a new modular P-element vector system," *Mol. Gen. Genet.* 262:916-920, Springer-Verlag (Jan. 2000).

Singh, J., et al., "Lead Development: Validation and Application of High Throughput Screening for Determination of Pharmacokinetic Parameters for Enzyme Inhibitors," *Bioorg. Med. Chem.* 4:639-643, Pergamon Press (May 1996).

Smouse, D. and Perrimon, N., "Genetic Dissection of a Complex Neurological Mutant, *polyhomeotic*, in *Drosophila,*" *Dev. Biol.* 139:169-185, Academic Press (1990).

Solari, A.J. "The Behavior of the XY Pair in Mammals," *Int. Rev. Cytol.* 38:273-317, Academic Press, Inc. (1974).

Stassen, M.J., et al., "The *Drosophila trithorax* proteins contain a novel variant of the nuclear receptor type DNA binding domain and an ancient conserved motif found in other chromosomal proteins," *Mech. Dev.* 52:209-223, Elsevier Science Ireland Ltd. (Aug. 1995).

Stebbins, J. and Debouck, C., "A Microtiter Colorimetric Assay for the HIV-1 Protease," *Anal. Biochem.* 248:246-250, Academic Press (Jun. 1997).

Strahl, B.D. and Allis, C.D., "The language of covalent histone modifications," *Nature* 403:41-45, Nature Publishing Group (Jan. 2000).

Strahl, B.D., et al., "Methylation of histone H3 at lysine 4 is highly conserved and correlates with transcriptionally active nuclei in *Tetrahymena,*" *Proc. Natl. Acad. Sci. USA* 96:14967-14972, National Academy of Sciences (Dec. 1999).

Sullivan, K.F., et al., "Human CENP-A Contains a Histone H3 Related Histone Fold Domain That Is Required for Targeting to the Centromere," *J. Cell Biol.* 127:581-592, The Rockefeller University Press (1994).

Tachibana, M., et al., "SET Domain-containing Protein, G9a, Is a Novel Lysine-preferring Mammalian Histone Methyltransferase with Hyperactivity and Specific Selectivity to Lysines 9 and 27 of Histone H3," *J. Biol. Chem.* 276:25309-25317, The American Society for Biochemistry and Molecular Biology, Inc. (Jul. 2001).

Taliani, M., et al., "A Continuous Assay of *Hepatitis C Virus* Protease Based on Resonance Energy Transfer Depsipeptide Substrates," *Anal. Biochem.* 240:60-67, Academic Press (Aug. 1996).

Tkachuk, D.C., et al., "Involvement of a Homolog of *Drosophila trithorax* by 11q23 Chromosomal Translocations in Acute *Leukemias*" *Cell* 71:691-700, Cell Press (1992).

Tschiersch, B., et al., "The protein encoded by the *Drosophila* position-effect variegation suppressor gene *Su(var)*3-9 combines domains of antagonistic regulators of homeotic gene complexes," *EMBO J.* 13:3822-3831, Oxford University Press (Aug. 1994).

Turner, B.M., "Histone acetylation as an epigenetic determinant of long-term transcriptional competence," *Cell. Mol. Life Sci.* 54:21-31, Birkhäuser Verlag (Jan. 1998).

Turner, J.M.A., et al., "Analysis of male meiotic "sex body" proteins during XY female meiosis provides new insights into their functions," *Chromosoma* 109:426-432, Springer-Verlag (Aug. 2000).

Uhlmann, F. and Nasmyth, K., "Cohesion between sister chromatids must be established during DNA replication," *Curr. Biol.* 8:1095-1101, Current Biology Ltd. (Sep. 1998).

Uhlmann, F., et al., "Sister-chromatid separation at anaphase onset is promoted by cleavage of the cohesin subunit Scc1," *Nature* 400:37-42, Nature Publishing Company (Jul. 1999).

Uhlmann, F., et al., "Cleavage of Cohesin by the CD Clan Protease Separin Triggers Anaphase in Yeast," *Cell* 103:375-386, Cell Press (Oct. 2000).

Vigil, P. and Bustos-Obregon, E., "Alkylating Agents and Mouse Spermatogenesis: Effects of a Single Dose of Cyclophosphamide," *Andrologia* 17:276-282, Grosse-Verlag (1985).

Waizenegger, I.C., "Two Distinct Pathways Remove Mammalian Cohesin from Chromosome Arms in Prophase and from Centromeres in Anaphase," *Cell* 103:399-410, Cell Press (Oct. 2000).

Wallrath, L.L., "Unfolding the mysteries of heterochromatin," *Curr. Opin. Genet. Dev.* 8:147-153, Current Biology Ltd. (Apr. 1998).

Wei, Y., et al., "Phosphorylation of Histone H3 Is Required for Proper Chromosome Condensation and Segregation," *Cell* 97:99-109, Cell Press (Apr. 1999).

Weinbauer, G.F., et al., "Quantitative Analysis of Spermatogenesis and Apoptosis in the Common Marmoset (*Callithrix jacchus*) Reveals High Rates of Spermatogonial Turnover and High Spermatogenic Efficiency," *Biol. Reprod.* 64:120-126, The Society for the Study of Reproduction, Inc. (Jan. 2001).

Wilson, I.A., et al., "The Structure of an Antigenic Determinant in a Protein," *Cell 37*: 767-778, Massachusetts Institute of Technology (1984).

Working, P.K., "Male Reproductive Toxicology: Comparison of the Human to Animal Models," *Environ. Health Perspect.* 77:37-44, U.S. Department of Health and Human Services (1988).

Wreggett, K.A., et al., "A mammalian homologue of *Drosophila* heterochromatin protein 1 (HP1) is a component of constitutive heterochromatin," *Cytogenet. Cell Genet.* 66:99-103, S. Karger AG (1994).

Xu, X., et al., "Centrosome Amplification and a Defective $G_2$-M Cell Cycle Checkpoint Induce Genetic Instability in BRCA1 Exon 11 Isoform-Deficient Cells," *Mol. Cell* 3:389-395, Cell Press (Mar. 1999).

Xu, Y., et al., "Targeted disruption of *ATM* leads to growth retardation, chromosomal fragmentation during meiosis, immune defects, and thymic lymphoma," *Genes Dev.* 10:2411-2422, Cold Spring Harbor Laboratory Press (Oct. 1996).

Yoshida, K., et al., "The Mouse *RecA*-like Gene *Dmc1* is Required for Homologous Chromosome Synapsis during Meiosis," *Mol. Cell* 1:707-718, Cell Press (Apr. 1998).

Yuan, L., et al., "The Murine *SCP3* Gene is Required for Synaptonemal Complex Assembly, Chromosome Synapsis, and Male Fertility," *Mol. Cell* 5:73-83, Cell Press (Jan. 2000).

Zhang, X., et al., "Pituitary Tumor Transforming Gene (PTTG) Expression in Pituitary Adenomas," *J. Clin. Endocrin. Metab:* 84:761-767, The Endocrine Society (Feb. 1999).

Zheng, Q., et al., "Expression, Purification, and Characterization of Recombinant Ribulose-1,5- Bisphosphate Carboxylase/Oxygenase Large Subunit $N^\varepsilon$—Methyltransferase," *Protein Express. Purif.* 14:104-112, Academic Press (Oct. 1998).

Zimmerman, M., et al., "Sensitive Assays for Trypsin, Elastase, and Chymotrypsin Using New Fluorogenic Substrates," *Anal. Biochem.* 78:47-51, Academic Press, Inc. (1977).

Zou, H. et al., "Identification of a Vertebrate Sister-Chromatid Separation Inhibitor Involved in Transformation and Tumorigenesis," *Science* 285:418-422, American Association for the Advancement of Science (Jul. 1999).

GenBank Report for Accession No. AAC29137, from Ying, Z. et al. (last updated Dec. 1999).

GenBank Report for Accession No. AAD39289, from Federspiel, N.A. et al. (last updated Oct. 2002).

GenBank Report for Accession No. D31891, from Nomura, N., et al. (last updated Jan. 2004).

GenBank Report for Accession No. D79987, from Nagase T., et al. (last updated Jan. 2004).

GenBank Report for Accession No. L08238, from Geraghty, M.T. (last updated Jan. 1995).

GenBank Report for Accession No. U18003, from Ostermeyer, E.A. (last updated Aug. 1998).

GenBank Report for Accession No. U52965, from Hobert, O., et al. (last updated Jul. 1996).

Co-Pending U.S. Appl. No. 09/500,991, Uhlmann et al., filed Feb. 15, 2000.

International Search Report for International Patent Application No. PCT/EP00/01183, mailed Jun. 29, 2000.

Dialog File 351, Accession No. 1996-518672, WPI English language abstract for document DE 195 16 776 (Document AM1).

Parisi, S., et al., "Rec8p, a Meiotic Recombination and Sister Chromatid Cohesion Phosphoprotein of the Rad21p Family Conserved from Fission Yeast to Humans," *Molec. Cell. Biol.* 19:3515-3528, American Society for Microbiology (May 1999).

```
EZH2 ─ 1    MGQTGKKSEKGPVCWRKRVKSEYMRLRQLKRFRRADEVKSMFSSNRQKIL    50
            ..|.|.|. |::|||||:::|| ||::||||:|. : .|::.
E(z)  ─ 1   .....MNSTKVPPEWKRRVKSEYIKIRQQKRYKRADEIKEAWIRNWDEHN    45

51     ERTEILNQEWKQRRIQPVHILTSVSSLRGTRECSVTSDLDFP...TQVIPL    98
            ...:  |  |.| :..|.    .. : ...||| ::| .| :|:
     46     HNVQDLYCESKVWQAKPYD....PPHVDCVKRAEVTSYNGIPSGPQKVPI    91

99     KTLNAVASVPIMYSWSPLQQNFMVEDETVLHNIPYMGDEVLDQDGTFIEE   148
            .:|||..:|.||.|.| ||||||||||||||||||||||.||.||||
     92     CVINAVTPIPTMYTWAPTQQNFMVEDETVLHNIPYMGDEVLDKDGKFIEE   141

149     LIKNYDGKVHGDRECGFINDEIFVELVNAL....................   178
            |||||||||||||:::.:|::|.||||||:||
    142     LIKNYDGKVHGDKDPSFMDDAIFVELVHALMRSYSKELEEAAPSTSTAIK   191

179     .......GQYNDDDDDDDGDDPE.....EREEKQKDLED..........H   206
                   | :||: | :.|.|       |:.|.. ||.|
    192     TEPLAKSKQGEDDGVVDVDADCESPMKLEKTESKGDLTDVEKKETEEPVE   241

207     RDDKESRPPRK.......FPSDKIFEAISSMFPDKGTAEELKEKYKELTE   249
            :| : :|:  .       ||.. ||:|||. |||||||:||||| ||||
    242     TEDADVKPAVEEVKDKLPFPAPIIFQAISANFPDKGTAQELKEKYIELTE   291

250     QQLPGALPPECTPNIDGPNAKSVQREQSLHSFHTLFCRRCFKYDCFLHPF   299
            :| |: |.|||||||| .|.|| ||...:|||||||||||||||||||.:
    292     HQDPER.PQECTPNIDGIKAESVSRERTMHSFHTLPCRRCFKYDCFLHRL   340

300     ..HATPNTYKRKNTETALDNKPCGPGCYQHLEGAKEFAAALTAERIKTPP   347
            ||.|| ||: .|  ..||: || ::|||  ||        ||||
    341     QGHAGPNLQKRRYPELKPFAERCSNSCYMLIDGMKEKLAA....DSKTPP   386

348     KRPGGRRRGRLPNNSSRPSTPTINVLESKDTDSDREAGTETGGENNDKEE   397
                         :  ..:.| :  ...:.. .|.| :.
    387     ......................IDSCNEASSEDSNDSNSQFSNKDFNH   412

398     EEKKDET.SSSSEANSRCQTPIKMKPNIEPPENVEWSGAEASMFRVLIGT   446
            |:.||:.  .|.|  ... : .||...| |.||:::|||  .
    413     ENSKDNGLTVNSAAVAEINSIMAGMMNITSTQCV.WTGADQALYRVLHKV   461

447     YYDNRCAIARLIGTKTCRQVYEFRVKESSIIAPAPAEDVDTPPRKKKRKH   496
            |..|:||||: :||||||||||||  ||.. :. .  : |||||||:|:
    462     YLKNYCAIAHNMLTKTCRQVYEFAQKEDAEFSFEDLRQDFTPPRKKKKKQ   511
```

FIG. 1A

```
497  RLWAAHCRKIQLKKDGSSNHVYNYQPCDHPRQPCDSSCPCVIAQNFCEKF  546  ⎤
     |||.||||||||||:|||||||| |||||| :|||  .|.|:  .|||||||     |
512  RLWSLHCRKIQLKKDSSSNHVYNYTPCDHPCHPCDMNCSCIQTQNFCEKF  561  ⎬ C-rich
                                                                75%
547  CDCSSECDNRFPGCRCKAQCNTKQCPCYLAVRECDPDLCLTCGAADHWDS  596  |
     |.|||:||||||||||||||||||||||||||||||||||||| .|| ||:::.    |
562  CNCSSDCDNRFPGCRCKAQCNTKQCPCYLAVRECDPDDCQACG.ADQFKL  610  ⎦

597  KNVSCKNCSIQRGSKKHLLLAP SDVAGWGIFIKDPVQKNEFISEYCGEII  646  ⎤
     ..:.|||.::|||.|||||:||||:|:|||||:|:...|||||||||||||      |
611  TKITCKNVCVQRGLHKHLLMAPSDIAGWGIFLKEGAQKNEFISEYCGEII  660  |
                                                                |
647  SQDEADRRGKVYDKYMCSFLFNLNNDFVVDATRKGNKIRFANHSVNPNCY  696  |
     ||||||||||||||||||||||||||||||||||||||||||||:||||        ⎬ SET
661  SQDEADRRGKVYDKYMCSFLFNLNNDFVVDATRKGNKIRFANHSINPNCY  710     88%
                                                                |
697  AKVMMVNGDHRIGIFAKRAIQTGEELFFDYRYSQADALKYVGIEREMEIP  746  |
     ||||||.|||||||||||||.||||||||:....||:||||||||||.         |
711  AKVMMVTGDHRIGIFAKRAIQPGEELFFDYRYGPTEQLKFVGIEREMEIV  760  ⎦
```

FIG. 1B

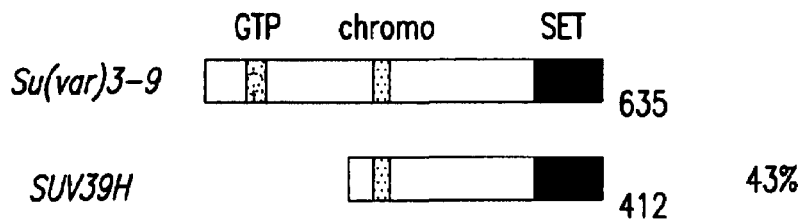

FIG. 2A

```
SUV39H
   ⌐ 1     MAENLKGCSVCCKSSWNQLQDLCRLAKLSCPALGISKRNLYDEEVEYLCD  50
Su(var)3-9          :. :||  ...:        : || :.                      ⌐
   ⌐ 207   ................MCVIAKRPPKG........EYVVERIEC  226         │
                                                                      │ CHROMO
    51     YKKIREQEYYLVKWRGYPDSESTWEPRQNLK.................  81       │  39%
           .. . |: ::||| ||.|||.|||. .|:                               │
    227    VENDQYQPVFFVKWLGYHDSENTWESLANVADCAEMEKFVERHQQLYETY 276     ⌐

82     CVRILKQFHKDLERELLRRHHRSKTPRHLDP.SLANYLVQKAKQRRALRR 130
           ..: | .::.:|:||    |.:     .:| .|. |:  |. | | .|
    277    IAKITTELEKQLEALPLMENITVAEVDAYEPLNLQIDLILLAQYRAAGSR 326

131    WEQE..........LNAKRSHLGR.....................IT  146
           ..|           :. ||.::.|                      |
    327    SQREPQKIGERALKSMQIKRAQFVRRKQLADLALFEKRMNHVEKPSPPIR 376

147    VENEVDLDGPPRAFVYINEYRVGEGITLNQVA.VQCECQDCLWAPTGCQC 195
           |||::|||. ...|:||:: ::|.:.  .: |||.|  :   ..|::.
    377    VENNIDLDTIDSNFMYIHDNIIGKDVPKPEAGIVQCKCTEDTEECTASTK 426

196    PGASL..HKFAYNDQC.QVRLRAGLPIYECNSRCRCGYDCPNRVVQKCIR 242
           ..|.:  . |||:   . .:|||:|  |:|||||||| .|.||.||.|.
    427    CCARFAGELFAYERSTRRLRLRPGSAIYECNSRCSCDSSCSNRLVQHGRQ 476

243    YDLCIFRTDDGRGWGVRTLEKIRKNSEVMEYVGEIITSEEAERRGQIYDR 292    ⌐
           .|.:|:|..:|.||||.. :||..|| ||::|||||||||: ||. ||          │
    477    VPLVLFKTANGSGWGVRAATALRKGEEVCEYIEEIITSDEANERGRAYDD 526      │

293    QGATYLFDLDY...VEDVYTVDAAYYGNISHFVNHSCDPNLQVYNVEIDN 339      │
           | |||||||||    :. ||:||| ||||||||.|:||||||.|: ..|:.          │
    527    NGRTYLFDLDYNTAQDSEYTIDAANYGNISHFINHSCDPNLAVEPCWIEH 576       │ SET
                                                                       │ 51%
    340    LDERLPRIAFFATRTIRAGEEELTFDYNMQVDPVDMESTRMDSNFGLAGLP 389
           |. ||::.||. |:|||||||.|||    :..|  |:.  ......
    577    LNVALPHLVFFTLRPIKAGEELSFDY.IRADNEDVPYENLSTA....... 618

390    GSPKKRVRIECKCGTESCRKYLF                            412
           ||:||:|| :.||| ||                                            │
    619    ......VRVECRCGRDNCRKVLF                            635    ⌐
```

FIG. 2B

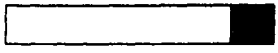
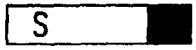
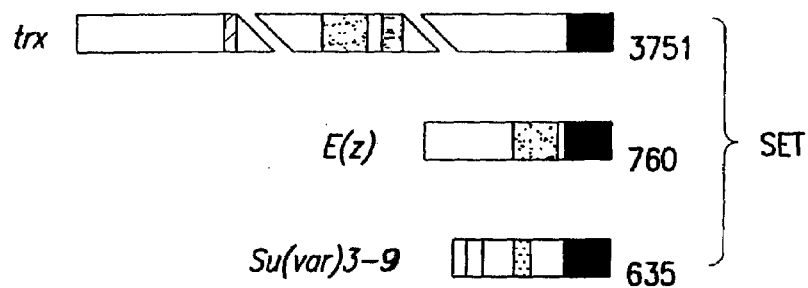
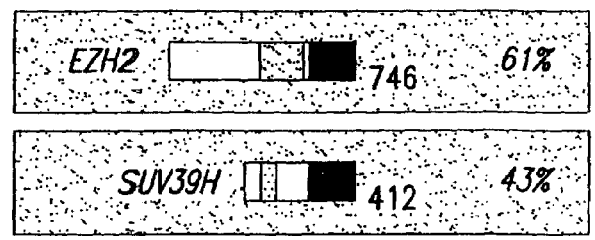
FIG. 4

```
E(z)     SDIAGWGIFL KEGAQKNEFI SEYCGEIISQ DEADRRGKVY DK..YMCSFL    50
EZH2     SDVAGWGIFI KDPVQKNEFI SEYCGEIISQ DEADRRGKVY DK..YMCSFL

HRX      SPIHGRGLFC KRNIDAGEMV IEYAGNVIRS IQTDKREKYY DSKGIG.CYM
trx      SHIHGRGLYC TKDIEAGEMV IEYAGELIRS TLTDKRERYY DSRGIG.CYM
C26      SRIHGWGLYA MESIAPDEMI VEYIGQTIRS LVAEEREKAY ERRGIGSSYL
YHR      SAIHNWGLYA LDSIAAKEMI IEYVGERTRQ PVAENREKRY LKNGIGSSYL Su3-9    ANGSGWGVRA ATALRKGEFV CEYIEEIITS DEANERGKAY DDNG..RTYL
SUV39H   DDGRGWGVRT LEKIRKNSFV MEYVGEIITS EEAERRGQIY DRQG..ATYL
G9a      TAKMGWGVRA LQTIPQGTFI CEYVGELISD AEAD...V.. .RED..DSYL
KG-1     TQNKGWGIRC LDDIAKGSFV CIYAGKILTD DFADKEGL.. .EMG..DEYF E(z)     FNLN...... NDFVVDATRK CNKIRFANHS INPNCYAKVM MVTGDH....    100
EZH2     FNLN...... NDFVVDATRK CNKIRFANHS VNPNCYAKVM MVNGDH....

HRX      FRID...... DSEVVDATMH CNRARFINHS CEPNCYSRVI NIDGQK....
trx      FKID...... DNLVVDATMR CNAARFINHC CEPNCYSKVV DILGHK....
C26      FRID...... LHHVIDATKR CNFARFINHS CCPNCYAKVL TIEGEK....
YHR      FRVD...... ENTVIDATKK CGIARFINHC CDPNCTAKII KVGGRR....

Su3-9    FDLDYNTAQD SEYTIDAANY CNISHFINHS CDPNLAVFPC WIEHLNVALP
SUV39H   FDLDY...VE DVYTVDAAYY CNISHFVNHS CDPNLQVYNV FIDNLDERLP
G9a      FDLDNK..DG EVYCIDARYY CNISRFINHL CDPNIIPVRV FMLHQDLRFP
KG-1     ANLDHI..ES VEYIIDAKLE CNLGRYLNHS CSPNLFVQNV FVDTHDLRFP
                  ↑

E(z)     RIGIFAKRAI QPGEELFFDY ..RYGPTEQL K.....FVCI EREMEIV*      150
EZH2     RIGIFAKRAI QTGEELFFDY ..RYSQADAL K.....YVCI EREMEIP*

HRX      HIVIFAMRKI YRGEELTYDY ..KFPIE.DA SNKLPCNCCA KKCRKFLN*
trx      HIIIFAVRRI VCGEELTYDY ..KFPFE.D. .EKIPCSCCS KRCRKYLN*
C26      RIVIYSRTII KKGEEITYDY ..KFPIE... DDKIDCLCCA KTCRGYLN*
YHR      RIVIYALRDI AASEELTYDY ..KFEREKDD EERLPCLCCA PNCKGFLN*

Su3-9    HLVFFTLRPI KAGEELSFDY .IRADNEDVP YENLSTA... ..........
SUV39H   RIAFFATRTI RAGEELTFDY NMQVDPVDME STRMDSNFCL AGLPGSPKKR
G9a      RIAFFSSRDT RTGEELGFDY GDRFW..DIK SKYFTCQCCS EKCKHSAEAI
KG-1     WVAFFASKRI RAGTELTWDY NYEVG..SVE GKELLCCCGA IECR......

E(z)
EZH2

HRX
trx
C26
YHR

Su3-9    VRVECRCGRD NCRKVLF*
SUV39H   VRIECKCGTE SCRKYLF*
G9a      ALEQSRLARL DPHPELLPEL GSLPPVNT*         FIG.5
KG-1     ....GRLL*
```

EZH2 length: 2600bp (coding: 90-2330)

```
   1  AGGCAGTGGAGCCCCGGCGGCGGCGGCGGCGGCGCGCGGGGGCGACGCGCGGGAACAACG   60
  61  CGAGTCGGCGCGCGGGACGAAGAATAATCATGGGCCAGACTGGGAAGAAATCTGAGAAGG  120
                                     M  G  Q  T  G  K  K  S  E  K  G
 121  GACCAGTTTGTTGGCCGAAGCGTGTAAAATCAGAGTACATGCGACTGAGACAGCTCAAGA  180
       P  V  C  W  R  K  R  V  K  S  E  Y  M  R  L  R  Q  L  K  R
 181  GGTTCAGACGAGCTGATGAAGTAAAGAGTATGTTTAGTTCCAATCGTCAGAAAATTTTGG  240
       F  R  R  A  D  E  V  K  S  M  F  S  S  N  R  Q  K  I  L  E
 241  AAAGAACGGAAATCTTAAACCAAGAATGGAAACAGCGAAGGATACAGCCTGTGCACATCC  300
       R  T  E  I  L  N  Q  E  W  K  Q  R  R  I  Q  P  V  H  I  L
 301  TGACTTCTGTGAGCTCATTGCGCGGGACTAGGGAGTGTTCGGTGACCAGTGACTTGGATT  360
       T  S  V  S  S  L  R  G  T  R  E  C  S  V  T  S  D  L  D  F
 361  TTCCAACACAAGTCATCCCATTAAAGACTCTGAATGCAGTTGCTTCAGTACCCATAATGT  420
       P  T  Q  V  I  P  L  K  T  L  N  A  V  A  S  V  P  I  M  Y
 421  ATTCTTGGTCTCCCCTACAGCAGAATTTTATGGTGGAAGATGAAACTGTTTTACATAACA  480
       S  W  S  P  L  Q  Q  N  F  M  V  E  D  E  T  V  L  H  N  I
 481  TTCCTTATATGGGAGATGAAGTTTTAGATCAGGATGGTACTTTCATTGAAGAACTAATAA  540
       P  Y  M  G  D  E  V  L  D  Q  D  G  T  F  I  E  E  L  I  K
 541  AAAAATTATGATGGGAAAGTACACGGGGATAGAGAATGTGGGTTTATAAATGATGAAATTT  600
       N  Y  D  G  K  V  H  G  D  R  E  C  G  F  I  N  D  E  I  F
 601  TTGTGGAGTTGGTGAATGCCCTTGGTCAATATAATGATGATGACGATGATGATGATGGAG  660
       V  E  L  V  N  A  L  G  Q  Y  N  D  D  D  D  D  D  D  G  D
 661  ACGATCCTGAAGAAAGAGAAGAAAAGCAGAAAGATCTGGAGGATCACCGAGATGATAAAG  720
       D  P  E  E  R  E  E  K  Q  K  D  L  E  D  H  R  D  D  K  E
 721  AAAGCCGCCCACCTCGGAAATTTCCTTCTGATAAAATTTTTGAAGCCATTTCCTCAATGT  780
       S  R  P  P  R  K  F  P  S  D  K  I  F  E  A  I  S  S  M  F
 781  TTCCAGATAAGGGCACAGCAGAAGAACTAAAGGAAAAATATAAAGAACTCACCGAACAGC  840
       P  D  K  G  T  A  E  E  L  K  E  K  Y  K  E  L  T  E  Q  Q
 841  AGCTCCCAGGCGCACTTCCTCCTGAATGTACCCCCAACATAGATGGACCAAATGCTAAAT  900
       L  P  G  A  L  P  P  E  C  T  P  N  I  D  G  P  N  A  K  S
 901  CTGTTCAGAGAGAGCAAAGCTTACACTCCTTTCATACGCTTTTCTGTAGGCGATGTTTTA  960
       V  Q  R  E  Q  S  L  H  S  F  H  T  L  F  C  R  R  C  F  K
 961  AATATGACTGCTTCCTACATCCTTTTCATGCAACACCCAACACTTATAAGCGGAAGAACA 1020
       Y  D  C  F  L  H  P  F  H  A  T  P  N  T  Y  K  R  K  N  T
1021  CAGAAACAGCTCTAGACAACAAACCTTGTGGACCACAGTGTTACCAGCATTTGGAGGGAG 1080
       E  T  A  L  D  N  K  P  C  G  P  Q  C  Y  Q  H  L  E  G  A
1081  CAAAGGAGTTTGCTGCTGCTCTCACCGCTGAGCGGATAAAGACCCCACCAAAACGTCCAG 1140
       K  E  F  A  A  A  L  T  A  E  R  I  K  T  P  P  K  R  P  G
```

FIG. 6A

```
1141 GAGGCCGCAGAAGAGGACGGCTTCCCAATAACAGTAGCAGGCCCAGCACCCCCACCATTA 1200
      G  R  R  R  G  R  L  P  N  N  S  S  R  P  S  T  P  T  I  N

1201 ATGTGCTGGAATCAAAGGATACAGACAGTGATAGGGAAGCAGGGACTGAAACGGGGGAG 1260
      V  L  E  S  K  D  T  D  S  D  R  E  A  G  T  E  T  G  G  E

1261 AGAACAATGATAAAGAAGAAGAAGAGAAGAAAGATGAAACTTCGAGCTCCTCTGAAGCAA 1320
      N  N  D  K  E  E  E  E  K  K  D  E  T  S  S  S  E  A  N

1321 ATTCTCGGTGTCAAACACCAATAAAGATGAAGCCAAATATTGAACCTCCTGAGAATGTGG 1380
      S  R  C  Q  T  P  I  K  M  K  P  N  I  E  P  P  E  N  V  E

1381 AGTGGAGTGGTGCTGAAGCCTCAATGTTTAGAGTCCTCATTGGCACTTACTATGACAATT 1440
      W  S  G  A  E  A  S  M  F  R  V  L  I  G  T  Y  Y  D  N  F

1441 TCTGTGCCATTGCTAGGTTAATTGGGACCAAAACATGTAGACAGGTGTATGAGTTTAGAG 1500
      C  A  I  A  R  L  I  G  T  K  T  C  R  Q  V  Y  E  F  R  V

1501 TCAAAGAATCTAGCATCATAGCTCCAGCTCCCGCTGAGGATGTGGATACTCCTCCAAGGA 1560
      K  E  S  S  I  I  A  P  A  P  A  E  D  V  D  T  P  P  R  K

1561 AAAAGAAGAGGAAACACCGGTTGTGGGCTGCACACTGCAGAAAGATACAGCTGAAAAAGC 1620
      K  K  R  K  H  R  L  W  A  A  H  C  R  K  I  Q  L  K  K  D

1621 ACGGCTCCTCTAACCATGTTTACAACTATCAACCCTGTGATCATCCACGGCAGCCTTGTG 1680
      G  S  S  N  H  V  Y  N  Y  Q  P  C  D  H  P  R  Q  P  C  D

1681 ACAGTTCGTGCCCTTGTGTGATAGCACAAAATTTTTGTGAAAAGTTTTGTCAATGTAGTT 1740
      S  S  C  P  C  V  I  A  Q  N  F  C  E  K  F  C  Q  C  S  S

1741 CAGAGTGTCAAAACCGCTTTCCGGGATGCCGCTGCAAAGCACAGTGCAACACCAAGCAGT 1800
      E  C  Q  N  R  F  P  G  C  R  C  K  A  Q  C  N  T  K  Q  C

1801 GCCCGTGCTACCTGGCTGTCCGAGAGTGTGACCCTGACCTCTGTCTTACTTGTGGAGCCG 1860
      P  C  Y  L  A  V  R  E  C  D  P  D  L  C  L  T  C  G  A  A

1861 CTGACCATTGGGACAGTAAAAATGTGTCCTGCAAGAACTGCAGTATTCAGCGGGGCTCCA 1920
      D  H  W  D  S  K  N  V  S  C  K  N  C  S  I  Q  R  G  S  K

1921 AAAAGCATCTATTGCTGGCACCATCTGACGTGGCAGGCTGGGGGATTTTTATCAAAGATC 1980
      K  H  L  L  A  P  S  D  V  A  G  W  G  I  F  I  K  D  P

1981 CTGTGCAGAAAAATGAATTCATCTCAGAATACTGTGGAGAGATTATTTCTCAAGATGAAG 2040
      V  Q  K  N  E  F  I  S  E  Y  C  G  E  I  I  S  Q  D  E  A

2041 CTGACAGAAGAGGGAAAGTGTATGATAAATACATGTGCAGCTTTCTGTTCAACTTGAACA 2100
      D  R  R  G  K  V  Y  D  K  Y  M  C  S  F  L  F  N  L  N  N

2101 ATGATTTTGTGGTGGATGCAACCCGCAAGGGTAACAAAATTCGTTTTGCAAATCATTCGG 2160
      D  F  V  V  D  A  T  R  K  G  N  K  I  R  F  A  N  H  S  V

2161 TAAATCCAAACTGCTATGCAAAAGTTATGATGGTTAACGGTGATCACAGGATAGGTATTT 2220
      N  P  N  C  Y  A  K  V  M  M  V  N  G  D  H  R  I  G  I  F

2221 TTGCCAAGAGAGCCATCCAGACTGGCGAAGAGCTGTTTTTTGATTACAGATACAGCCAGG 2280
      A  K  R  A  I  Q  T  G  E  E  L  F  F  D  Y  R  Y  S  Q  A
```

FIG. 6B

```
2281  CTGATGCCCTGAAGTATGTCGGCATCGAAAGAGAAATGGAAATCCCTTGACATCTGCTAC  2340
       D   A   L   K   Y   V   G   I   E   R   E   M   E   I   P   *
2341  CTCCTCCCCCTCCTCTGAAACAGCTGCCTTAGCTTCAGGAACCTCGAGTACTGTGGGCAA  2400
2401  TTTAGAAAAAGAACATGCAGTTTGAAATTCTGAATTTGCAAAGTACTGTAAGAATAATTT  2460
2461  ATAGTAATGAGTTTAAAAATCAACTTTTTATTGCCTTCTCACCAGCTGCAAAGTGTTTTG  2520
2521  TACCAGTGAATTTTTGCAATAATGCAGTATGGTACATTTTTCAACTTTGAATAAAGAATA  2580
2581  CTTGAACTTGTCAAAAAAAA                                          2600
```

FIG. 6C

SUV39H length: 2732bp (coding: 45-1284)

```
   1 TCGCGAGGCCGGCTAGGCCCGAATGTCGTTAGCCGTGGGGAAAGATGGCGGAAAATTTAA   60
                                                  M  A  E  N  L  K

61 AAGGCTGCAGCGTGTGTTGCAAGTCTTCTTGGAATCAGCTGCAGGACCTGTGCCGCCTGG  120
      G  C  S  V  C  C  K  S  S  W  N  Q  L  Q  D  L  C  R  L

121 CCAAGCTCTCCTGCCCTGCCCTCGGTATCTCTAAGAGGAACCTCTATGACTTTGAAGTCG  180
      A  K  L  S  C  P  A  L  G  I  S  K  R  N  L  Y  D  F  E  V  E

181 AGTACCTGTGCGATTACAAGAAGATCCGCGAACAGGAATATTACCTGGTGAAATGGCGTG  240
      Y  L  C  D  Y  K  K  I  R  E  Q  E  Y  Y  L  V  K  W  R

241 GATATCCAGACTCAGAGAGCACCTGGGAGCCACGGCAGAATCTCAAGTGTGTGCGTATCC  300
      G  Y  P  D  S  E  S  T  W  E  P  R  Q  N  L  K  C  V  R  I  L

301 TCAAGCAGTTCCACAAGGACTTAGAAAGGGAGCTGCTCCGGCGGCACCACCGGTCAAAGA  360
      K  Q  F  H  K  D  L  E  R  E  L  L  R  R  H  H  R  S  K  T

361 CCCCCCGGCACCTGGACCCAAGCTTGGCCAACTACCTGGTGCAGAAGGCCAAGCAGAGGC  420
      P  R  H  L  D  P  S  L  A  N  Y  L  V  Q  K  A  K  Q  R  R

421 GGGCGCTCCGTCGCTGGGAGCAGGAGCTCAATGCCAAGCGCAGCCATCTGGGACGCATCA  480
      A  L  R  R  W  E  Q  E  L  N  A  K  R  S  H  L  G  R  I  T

481 CTGTAGAGAATGAGGTGGACCTGGACGGCCCTCCGCGGGCCTTCGTGTACATCAATGAGT  540
      V  E  N  E  V  D  L  D  G  P  P  R  A  F  V  Y  I  N  E  Y

541 ACCGTGTTGGTGAGGGCATCACCCTCAACCAGGTGGCTGTGGGCTGCGAGTGCCAGGACT  600
      R  V  G  E  G  I  T  L  N  Q  V  A  V  G  C  E  C  Q  D  C

601 GTCTGTGGGCACCCACTGGAGGCTGCTGCCCGGGGGCGTCACTGCACAAGTTTGCCTACA  660
      L  W  A  P  T  G  G  C  C  P  G  A  S  L  H  K  F  A  Y  N

661 ATGACCAGGGCCAGGTGCGGCTTCGAGCCGGGCTGCCCATCTACGAGTGCAACTCCCGCT  720
      D  Q  G  Q  V  R  L  R  A  G  L  P  I  Y  E  C  N  S  R  C

721 GCCGCTGCGGCTATGACTGCCCCAAATCGTGTGGTACAGAAGGGTATCCGATATGACCTCT  780
      R  C  G  Y  D  C  P  N  R  V  V  Q  K  G  I  R  Y  D  L  C

781 GCATCTTCCGGACCGATGATGGGCGTGGCTGGGGCGTCCGCACCCTGGAGAAGATTCGCA  840
      I  F  R  T  D  D  G  R  G  W  G  V  R  T  L  E  K  I  R  K

841 AGAACAGCTTCGTCATGGAGTACGTGGGAGAGATCATTACCTCAGAGGAGGCAGAGCGGC  900
      N  S  F  V  M  E  Y  V  G  E  I  I  T  S  E  E  A  E  R  R

901 GGGGCCAGATCTACGACCGTCAGGGCGCCACCTACCTCTTTGACCTGGACTACGTGGAGG  960
      G  Q  I  Y  D  R  Q  G  A  T  Y  L  F  D  L  D  Y  V  E  D

961 ACGTGTACACCGTGGATGCCGCCTACTATGGCAACATCTCCCACTTTGTCAACCACAGTT  1020
      V  Y  T  V  D  A  A  Y  Y  G  N  I  S  H  F  V  N  H  S  C

1021 GTGACCCCAACCTGCAGGTGTACAACGTCTTCATAGACAACCTTGACGAGCGGCTGCCCC  1080
      D  P  N  L  Q  V  Y  N  V  F  I  D  N  L  D  E  R  L  P  R

1081 GCATCGCTTTCTTTGCCACAAGAACCATCCGGGCACGCGAGGAGCTCACCTTTGATTACA  1140
      I  A  F  F  A  T  R  T  I  R  A  G  E  E  L  T  F  D  Y  N
```

FIG. 7A

```
1141  ACATGCAAGTGGACCCCGTGGACATGGAGAGCACCCGCATGGACTCCAACTTTGGCCTGG  1200
       M  Q  V  D  P  V  D  M  E  S  T  R  M  D  S  N  F  G  L
1201  CTGGGCTCCCTGGCTCCCCTAAGAAGCGGGTCCGTATTGAATGCAAGTGTGGGACTGAGT  1260
       G  L  P  G  S  P  K  K  R  V  R  I  E  C  K  C  G  T  E  S
1261  CCTGCCGCAAATACCTCTTCTAGCCCTTAGAAGTCTGAGGCCAGACTGACTGAGGGGCC  1320
       C  R  K  Y  L  F  *
1321  TGAAGCTACATGCACCTCCCCCACTGCTGCCCTCCTGTCGAGAATGACTGCCAGGGCCTC  1380
1381  GCCTGCCTCCACCTGCCCCCACCTGCTCCTACCTGCTCTACGTTCAGGGCTGTGGCCGTG  1440
1441  GTGAGGACCGACTCCAGGAGTCCCCTTTCCCTGTCCCAGCCCCATCTGTGGGTTGCACTT  1500
1501  ACAAACCCCCACCCACCTTCAGAAATAGTTTTTCAACATCAAGACTCTCTGTCGTTGGGA  1560
1561  TTCATGCCTATTAAGGAGGTCCAAGGGGTGAGTCCCAACCCAGCCCCAGAATATATTTG  1620
1621  TTTTTGCACCTGCTTCTGCCTGGAGATTGAGGGGTCTGCTGCAGGCCTCCTCCCTGCTGC  1680
1681  CCCAAAGGTATGGGGAAGCAACCCCAGAGCAGGCAGACATCAGAGGCCAGAGTGCCTAGC  1740
1741  CCGACATGAAGCTGGTTCCCCAACCACAGAAACTTTGTACTAGTGAAAGAAAGGGGTCCC  1800
1801  TGGCCTACGGGCTGAGGCTGGTTTCTGCTCGTGCTTACAGTGCTGGGTAGTGTTGGCCCT  1860
1861  AAGAGCTGTAGGGTCTCTTCTTCAGGGCTGCATATCTGAGAAGTGGATGCCCACATGCCA  1920
1921  CTGGAAGGGAAGTGGGTGTCCATGGGCCACTGAGCAGTGAGAGGAAGGCAGTGCAGAGCT  1980
1981  GGCCAGCCCTGGAGGTAGCCTGGGACCAAGCTCTGCCTTCACAGTGCAGTGAAGGTACCT  2040
2041  AGGGCTCTTGGGAGCTCTGCGGTTGCTAGGGGCCCTGACCTGGGGTGTCATGACCGCTGA  2100
2101  CACCACTCAGAGCTGGAACCAAGATCTAGATAGTCCGTAGATAGCACTTAGGACAAGAAT  2160
2161  GTGCATTGATGGGGTGGTGATGAGGTGCCAGGCACTAGGTAGAGCACCTGGTCCACCTGG  2220
2221  ATTGTCTCAGGGAAGCCTTGAAAACCACGGAGGTGGATGCCAGGAAAGGGCCCATGTGGC  2280
2281  AGAAGGCAAAGTACAGGCCAAGAATTGGGGGTGGGGGAGATGGCTTCCCCACTATGGGAT  2340
2341  GACGAGGCGAGAGGGAAGCCCTTGCTGCCTGCCATTCCCAGACCCCAGCCCTTTGTGCTC  2400
2401  ACCCTGGTTCCACTGGTCTCAAAAGTCACCTGCCTACAAATGTACAAAAGGCGAAGGTTC  2460
2461  TGATGGCTGCCTTGCTCCTTGCTCCCCCACCCCCTGTGAGGACTTCTCTAGGAAGTCCTT  2520
2521  CCTGACTACCTGTGCCCAGAGTGCCCCTACATGAGACTGTATGCCCTGCTATCAGATGCC  2580
2581  AGATCTATGTGTCTGTCTGTGTGTCCATCCCGCCGGCCCCCCAGACTAACCTCCAGCCAT  2640
2641  GGACTGAATCTGGTTCTCCTCTTGTACACCCCTCAACCCTATGCAGCCTGGAGTGGGCAT  2700
2701  CAATAAAATGAACTGTCGACTGAAAAAAAAAA                               2732
```

FIG. 7B

```
EZH2 ─── 1844 TCTTACTTGTGGAGCCGCTGACCATTGGGACAGTAAAAATGTGTCCTGCA 1893
              || || |||||| ||| | || || ||||||| | ||    || |||||| |
EZH1 ───    1 ACTCACCTGTGGGGCCTCAGAGCACTGGGACTGCAAGGTGGTTTCCTGTA 50

1894 AGAACTGCAGTATTCAGCGGGGCTCCAAAAAGCATCTATTGCTGGCACCA 1943
              | |||||||| || |||||| ||    || ||||| || |||||| ||
           51 AAAACTGCAGCATCCAGCGTGGACTTAAGAAGCACCTGCTGCTGGCCCCC 100

1944 TCTGACGTGGCAGGCTGGGGGATTTTTATCAAAGATCCTGTGCAGAAAAA 1993
              ||||| ||||| || |||||| | || || || |||||||||| ||
B52······ 101 TCTGATGTGGCCGGATGGGGCACCTTCATAAAGGAGTCTGTGCAGAAGAA 150

1994 TGAATTCATCTCAGAATACTGTGCAGAGATTATTTCTCAAGATGAAGCTG 2043
              |||||||| || ||||||||||| |||  | || ||||| ||||| ||||
          151 CGAATTCATTTCTGAATACTGTGGTGAGCTCATCTCTCAGGATGAGGCTG 200

2044 ACAGAAGAGGGAAAGTGTATGATAAATACATGTGCAGCTTTCTGTTCAAC 2093
              |  || | || || || ||||| |||||||||||| ||||| || ||||||
          201 ATCGACGCGGAAAGGTCTATGACAAATACATGTCCAGCTTCCTCTTCAAC 250

2094 TTGAACAATGATTTTGTCGTGGATGCAACCCGCAAGGGTAACAAAATTCG 2143
              | || ||||||||||| || |||||||| || || || || |||||||||
          251 CTCAATAATGATTTTGTAGTGGATGCTACTCGGAAAGGAAACAAAATTCG 300

2144 TTTTGCAAATCATTCGGTAAATCCAAACTGCTATGCAAAAGTT...ATGAT 2191
              ||||||||||||||| || ||||| ||||| ||||| ||||||      |
          301 ATTTGCAAATCATTCAGTGAATCCCAACTGTTATGCCAAAGGTGAGTCCC 350

2192 GGTTAACGGTGATCACAGGATAGGTATTTTTGCCAAGAGAGCCATCCAGA 2241
              || | | ||    ||  || || |||| |    |
          351 AGTAACCTGGGAGGTGGGGTGGGGGATGGATGCCTCTTTACTGTGATTTC 400

2242 CTGGCGAAGAGCTGTTTTTTGATTACAGATACAGCCAGGCTGATGCCCTG 2291
              |  || |     |||| |||         |  |
          401 CATTCGTTGTTGAACATTTTCCTTAGCTGAGCTATCTTTTGTCCAAAGAT 450

2292 AAGTATGTCGGCATCGAAAGAGAAATGGAAATCCCTTGA *          2330
              ||  |||        |  |  |  | ||||
          451 AATCATGATTAATATCTGGTATCATTTTAGGCCCCTCTC            489
```

CHROMATIN REGULATOR GENES

CROSS-REFERENCE TO RELATED APPLICATIONS

This application is a continuation-in-part of U.S. application Ser. No. 08/945,988, filed Nov. 10, 1997, which is the national phase entry application of PCT/EP96/01818, filed May. 2, 1996, claiming priority to German Application No. DE 195 16 776.7, filed May 10, 1995. These applications are incorporated herewith by reference in their entirety.

BACKGROUND OF THE INVENTION

1. Field of the Invention

The present invention relates to genes which play a part in the structural and functional regulation of chromatin, and their use in therapy and diagnosis.

2. Related Art

Higher-order chromatin is essential for epigenetic gene control and for the functional organization of chromosomes. Differences in higher-order chromatin structure have been linked with distinct covalent modifications of histone tails which regulate transcriptional 'on' or 'off' states and influence chromosome condensation and segregation.

Histones constitute a highly conserved family of proteins (H3, H4, H2A, H2B, H1) which are the major components of eucaryotic chromatin structure. Histones compact genomic DNA into basic repeating structural units, the nucleosomes. In addition to their DNA packaging function, histones have been proven to be integral components of the molecular machinery that regulates gene expression.

Post-translational modifications of histone N-termini, particularly of H4 and H3, are well-documented and have functionally been characterized as changes in acetylation, phosphorylation and, most recently, methylation. In contrast to the large number of described histone acetyltransferases (HATs) and histone deacetylases (HDACs), genes encoding enzymatic activities that regulate phosphorylation or methylation of histone N-termini are only beginning to be identified. Moreover, the interdependence of the different histone tail modifications for the integration of transcriptional output or higher-order chromatin organization is currently not understood.

Overall, there is increasing evidence that the regulation of normal and aberrant cellular proliferation is not only affected on the transcriptional level, but that also a higher level of regulation is involved, i.e., the organization of chromatin structure through the modification of histone molecules. The determination of the proteins and the molecular mechanisms involved in histone modification will contribute to the understanding of the cellular proliferation program and will thus shed light on the mechanisms involved in aberrant proliferation occurring in tumor formation and progression.

The functional organization of eucaryotic chromosomes in centromeres, telomeres and eu- and heterochromatic regions is a crucial mechanism for ensuring exact replication and distribution of genetic information on each cell division. By contrast, tumor cells are frequently characterized by chromosomal rearrangements, translocations and aneuploidy (Solomon, et al., *Science* 254:1153–1160 (1991); Pardue, *Cell* 66:427–431 (1991)).

Although the mechanisms which lead to increased chromosome instability in tumor cells have not yet been clarified, a number of experimental systems, beginning with telomeric positional effects in yeast (Renauld, et al., *Genes & Dev.* 7: 1133–1145 (1993); Buck and Shore, *Genes & Dev.* 9:370–384 (1995); Allshire, et al., *Cell* 76:157–169 (1994)), via positional effect variegation (PEV) in *Drosophila* (Reuter and Spierer, *BioEssays* 14:605–612 (1992)), and up to the analysis of translocation fracture points in human leukaemias (Solomon, et al., *Science* 254:1153–1160 (1991); Cleary, et al., *Cell* 66:619–622 (1991)), have made it possible to identify chromosomal proteins which are involved in causing deregulated proliferation.

First, it was found that the overexpression of a shortened version of the SIR4-protein leads to a longer life in yeast (Kennedy, et al., *Cell* 80:485–496 (1995)). Since SIR proteins contribute to the formation of multimeric complexes at the stationary mating type loci and at the telomere, it could be that overexpressed SIR4 interferes with these heterochromatin-like complexes, finally resulting in uncontrolled proliferation. This assumption accords with the frequency of occurrence of a deregulated telomere length in most types of human cancer (Counter, et al., *Embo. J.* 11:1921–1928 (1992)).

Second, genetic analyses of PEV in *Drosophila* have identified a number of gene products which alter the structure of chromatin at heterochromatic positions and within the homeotic gene cluster (Reuter and Spierer, *BioEssays* 14:605–612 (1992)). Mutations of some of these genes, such as modulo (Garzino, et al., *Embo J.* 11:4471–4479 (1992)) and polyhomeotic (Smouse and Perrimon, *Dev. Biol.* 139: 169–185 (1990)), can cause deregulated cell proliferation or cell death in *Drosophila*.

Third, mammalian homologues of both activators, e.g., trithorax or trx-group, and also repressors, e.g., polycomb or Pc-group, of the chromatin structure of homeotic *Drosophila* selector genes have been described. Among these, human HRX/ALL-1 (trx-group) has been shown to be involved in leukaemogenesis induced by translocation (Tkachuk, et al., *Cell* 71:691–700 (1992); Gu, et al., *Cell* 71:701–708 (1992)), and it has been shown that the overexpression of murine bmi (Pc-group) leads to the formation of lymphomas (Haupt, et al., *Cell* 65:753–763 (1991); Brunk, et al., *Nature* 353:351–355 (1991); Alkema, et al., *Nature* 374:724–727 (1995)). A model for the function of chromosomal proteins leads one to conclude that they form multimeric complexes which determine the degree of condensation of the surrounding chromatin region depending on the balance between activators and repressors in the complex (Locke, et al., *Genetics* 120:181–198 (1988)). A shift in this equilibrium, caused by overexpression of one of the components of the complex, exhibited a new distribution of eu- and heterochromatic regions (Buck and Shore, *Genes & Dev.* 9:370–384 (1995); Reuter and Spierer, *BioEssays* 14:605–612 (1992); Eissenberg, et al., *Genetics* 131:345–352 (1992)) which can destabilize the chromatin structure at predetermined loci, and lead to a transition from the normal to the transformed state.

In spite of the characterization of HRX/ALL-1 and bmi as protooncogenes which are capable of changing the chromatin structure, knowledge of mammalian gene products which interact with chromatin is still very limited. By contrast, by genetic analyses of PEV in *Drosophila*, about 120 alleles for chromatin regulators have been described (Reuter and Spierer, *BioEssays* 14:605–612 (1992)).

Recently, a carboxy-terminal region was identified with similarity in the sequence to a positive (trx (trx-group)) and a negative (E(z) (Pc-group)) *Drosophila* chromatin regulator (Jones and Gelbart, *MCB* 13(10):6357–6366 (1993)). Moreover, this carboxy terminus is conserved in Su(var)3-9, a member of the Su(var) group, and a dominant suppressor of chromatin distribution in *Drosophila* (Tschiersch, et al., *Embo J*. 13(16):3822–3831 (1994)).

Genetic screens for suppressors of position effect variegation (PEV) in *Drosophila* and *S. pombe* have identified a subfamily of approximately 30–40 loci which are referred to as Su(var)-group genes. Interestingly, several histone deacetylases, protein phosphatase type 1 and S-adenosyl methionine synthetase have been classified as Su(var)s. In contrast, Su(var)2-5 (which is allelic to HP1), Su(var)3-7 and Su(var)3-9 encode heterochromatin-associated proteins. Su(var) gene function thus suggests a model in which modifications at the nucleosomal level may initiate the formation of defined chromosomal subdomains that are then stabilized and propagated by heterochromatic SU(VAR) proteins. Su(var)3-9 is dominant over most PEV modifier mutations, and mutants in the corresponding *S. pombe* clr4 gene disrupt heterochromatin association of other modifying factors and result in chromosome segregation defects. Recently, human (SUV39H1) and murine (Suv39h1 and Suv39h2) Su(var)3-9 homologues have been isolated. It has been shown that they encode heterochromatic proteins which associate with mammalian HP1. The SU(VAR)3-9 protein family combines two of the most evolutionarily conserved domains of 'chromatin regulators': the chromo and the SET domain. Whereas the 60 amino acid chromo domain represents an ancient histone-like fold that directs eu- or heterochromatic localizations, the molecular role of the 130 amino acid SET domain has remained enigmatic. Overexpression studies with human SUV39H1 mutants indicated a dominant interference with higher-order chromatin organization that, surprisingly, suggested a functional relationship between the SET domain and the distribution of phosphorylated (at serine 10) H3.

The experiments of the present invention show that mammalian SUV39H1 or Suv39h proteins are SET domain-dependent, H3-specific histone methyltransferases (HMTases) which selectively methylate lysine 9 of the H3 N-terminus. Methylation of lysine 9 negatively regulates phosphorylation of serine 10 and reveals a 'histone code' that appears intrinsically linked to the organization of higher-order chromatin.

SUMMARY OF THE INVENTION

The Su(var)3-9 protein family combines two of the most evolutionarily conserved domains of chromatin regulators: the chromo (Aasland, R. and Stewart, A. F., *Nucleic Acids Res* 23:3168–74 (1995); Koonin, E. V., et al., *Nucleic Acids Res* 23:4229–33 (1995)) and the SET (Jenuwein, T., et al., *Cell Mol Life Sci* 54:80–93 (1998)) domain. Whereas the 60 amino acid chromo domain represents an ancient histone-like fold (Ball, L. J., et al., *EMBO J* 16:2473–2481 (1997)) that directs eu- or heterochromatic localizations (Platero, J. S., et al., *Embo J* 14:3977–86 (1995)), the molecular role of the 130 amino acid SET domain has remained enigmatic.

The present invention started from the premise that the protein domain referred to as "SET" (Tschiersch, et al., *Embo J*. 13(16):3822–3831 (1994)) defines a new genetic family of mammalian chromatin regulators which are important in terms of their developmental history on account of their evolutionary conservation and their presence in antagonistic gene products. Moreover, the characterization of other members of the group of SET domain genes, apart from HRX/ALL-1, helps to explain the mechanisms which are responsible for structural changes in chromatin possibly leading to malignant transformation.

One aspect of the present invention is therefore to identify mammalian, such as human and murine, chromatin regulator genes, clarify their function and use them for diagnosis and therapy. More specifically, the sequences of the SUV39H proteins, and variants thereof, and EZH2 proteins, and variants thereof, according to the invention, may be used to analyze the interaction of SET domain proteins with chromatin or with other members of heterochromatin complexes. Starting from the findings thus obtained regarding the mode of activity of these proteins, the detailed possibilities for targeted intervention in the mechanisms involved therein are defined and may be used for therapeutic applications as described in detail below.

In order to achieve this objective, the sequence information of the SET domain was used to obtain the human cDNA homologous to the SET domain genes of *Drosophila* from human CDNA banks. Two cDNAs were obtained which constitute human homologues of E(z) and Su(var)3-9. The corresponding human genes are referred to as EZH2 and SUV39H. See FIGS. 6A–6C and 7A–7B. In addition, a variant form of EZH2 was identified which is referred to as EZH1. See FIG. 8.

The present invention thus relates to DNA molecules containing a nucleotide sequence coding for a chromatin regulator protein which has a SET-domain, or a partial sequence thereof, characterized in that the nucleotide sequence is that shown in FIGS. 6A–6C (SEQ ID NO:1), or a partial sequence thereof, or FIGS. 7A–7B (SEQ ID NO:3), or a partial sequence thereof. The DNA molecules, including variants and mutants thereof such as dominant-negative mutants, are also referred to as "genes according to the invention." Two examples of genes according to the invention are designated EZH2 and SUV39H. They were originally referred to as "HEZ-2" and "H3-9," respectively.

According to another aspect, the invention relates to the cDNAs derived from the genes of the invention, including the degenerate variants thereof, and mutants thereof, which code for functional chromatin regulators and which can be traced back to gene duplication. An example of this is EZH1 (SEQ ID NO:5), the partial sequence of which is shown by comparison with EZH2 (SEQ ID NO:1) in FIG. 8.

According to another aspect, the invention relates to recombinant DNA molecules containing the cDNA molecules, functionally connected to expression control sequences, for expression in procaryotic or eucaryotic host organisms. Thus, the invention further relates to procaryotic or eucaryotic host organisms transformed with the recombinant DNA.

The invention further relates to antisense(deoxy)ribonucleotides with complementarity to a partial sequence of an inventive DNA molecule.

The invention further relates to transgenic animals, such as transgenic mice, which comprise a trans gene for the expression of a chromatin regulator gene which has a SET domain, or a mutated version or degenerate variant of such a protein.

The invention further relates to knock-out animals such as knock-out mice, obtainable from embryonic stem cells in which the endogenous mouse loci for EZH1 and SUV39H are interrupted by homologous recombination.

The invention further relates to a process for identifying mammalian chromatin regulator genes which have a SET domain, or mutated versions thereof, wherein mammalian cDNA or genomic DNA libraries are hybridized under non-stringent conditions with a DNA molecule coding for the SET domain or a portion thereof.

The invention further relates to antibody molecules which bind to a polypeptide which contains the amino acid sequence depicted in SEQ ID NOS:2 or 4 or degenerate variants or mutants thereof.

Other aspects of the invention are set forth in the Detailed Description of the Preferred Embodiments.

BRIEF DESCRIPTION OF THE FIGURES

FIGS. 1A–1B are an amino acid sequence comparison between EZH2 (SEQ ID NO:2) and *Drosophila* enhancer of zeste (E(z)) (SEQ ID NO:11). The conserved carboxy terminal SET-domain (shaded box) and the Cys-rich region (Cys groups are emphasized) are shown. Percent identity is shown on the right side. The presumed nucleus locating signals are underlined.

FIGS. 2A–2B are an amino acid sequence comparison between the human homologue SUV39H (SEQ ID NO:4) and *Drosophila* Su(var)3-9 (SEQ ID NO:16). The conserved carboxy terminal SET-domain (shaded box) and the Chromo-domain (darker shaded box) are shown. Percent identity is shown on the right side. The presumed nucleus locating signals are underlined. FIG. 2A is a diagrammatic summary of the two protein structures which shows that, in the human homologue, 207 amino acids are missing at the N-terminus.

FIG. 3 shows, inter alia, the three genes (HRX/ALL-1, EZH1/B52 and SUV39H/MG-44) for which aberrant cDNAs have been mapped on translocation fracture points or unstable chromatin regions. Four of the five SET-domain genes shown have mutations, all of which interrupt the carboxy terminal SET-domain. A translocation connects the amino terminal half of HRX to a non-correlated gene sequence which is shown as a dotted box designated ENL. Mutations and a premature stop codon change the SET-domain of EZH1/B52. Point and frameshift mutations interrupt the Chromo- and SET-domain in MG-44. A large insertion cleaves the SET-domain of KG-1 into two halves. At present, there are no known aberrant transcripts for G9a. The cysteine-rich cluster in B52 is shown as a dotted box. In HRX/ALL-1, the region of homology with methyltransferase is shown as a shaded box and the A/T-hooks are shown as vertical lines.

FIG. 4 shows the evolutionary conservation of SET-domain proteins. Using the tfasta program of the Wisconsin GCG Network Service, proteins and open reading frames with homology to the SET-domain were identified. The figure shows a representative selection from yeasts to humans. The numbers indicate the amino acids. The carboxy terminal SET-domain is represented by a black box, Cys-rich regions are indicated by a darkly dotted box, and the chromo-domain of Su(var)3-9 and SUV39H are indicated by an open box with light dots. A region which is homologous to methyltransferase (trx and HRX) is shown as a shaded box. A/T hooks are indicated by vertical lines. Another Ser-rich region (S in C26E6.10) and a Glu-rich region (E in G9a) or ankyrin repeats (ANK in G9a) are also emphasized. YHR119 (GeneBank Accession No. U00059) and C26E6.10 (GeneBank Accession No. U13875) are open reading frames of cosmids in the databank without functional characterization. The percentages indicate the total amino acid identity between the human and the *Drosophila* proteins.

FIG. 5 shows the concordance between the amino acids in the SET domain in various *Drosophila* and human proteins. Specifically, the EZH2 (SEQ ID NO:2) and SUV39H (SEQ ID NO:4) amino acid sequences were compared to the E(z) (SEQ ID NO:11), HRX (SEQ ID NO:12), trx (SEQ ID NO:13), C26 (SEQ ID NO:14), YHR (SEQ ID NO:15), Su(var)3-9 (SEQ ID NO:16); G9a (SEQ ID NO:17) and KG-1 (SEQ ID NO:18) amino acid sequences. The SET domain of the genes shown in FIG. 5 was arranged using the Pileup program of the Wisconsin GCG Network Service. In order to compare the KG-1 SET domain, the large amino acid insert which splits the SET domain into two halves was removed before the pileup. See FIG. 3.

FIGS. 6A–6C illustrate the DNA and amino acid sequences of EZH2 (SEQ ID NOS:1 and 2, respectively).

FIGS. 7A–7B illustrate the DNA and amino acid sequences of SUV39H (SEQ ID NOS:3 and 4, respectively).

FIG. 8 is a sequence comparison between the cDNAs of human EZH2 (SEQ ID NO:1) and EZH1 (SEQ ID NO:5). More specifically, FIG. 8 shows the nucleotide sequence of EZH2 (SEQ ID NO:1) cDNA from position 1844 to 2330 in the upper line, the 5' splicing site and the potential stop codon being underlined. In order to ascribe a partial sequence of the cDNA of the EZH1 variant (SEQ ID NO:5) to the EZH2 sequence (SEQ ID NO:1) we used the gap program of the Wisconsin GCG Network Service. The premature stop codon in EZH1 (position 353) is underlined. Sequences which code for the conserved SET-domain are emboldened. Moreover, the 3'-end (position 151 in EZH1) of the aberrant transcript B52 (discussed below) is shown. Over the available sequence, B52 was found to be 97% identical to EZH1 and 72% identical to EZH2.

In FIG. 9B, recombinant GST-fusion proteins encoding different domains of murine Suv39h1 were used in increasing protein concentrations for in vitro HMTase reactions as described above. The top panel is the Coomassie stain and the bottom panel is the fluorogram.

FIG. 10C illustrates automated sequencing of the wild-type H3 N-terminal peptide (aa 1-20) that had been methylated in vitro by recombinant GST-Suv39h1(aa 82-412). Displayed is the $^3$H-incorporation of individual amino acids identified at each successive round of microsequencing.

DETAILED DESCRIPTION OF THE PREFERRED EMBODIMENTS

Sequencing

Figure 3:
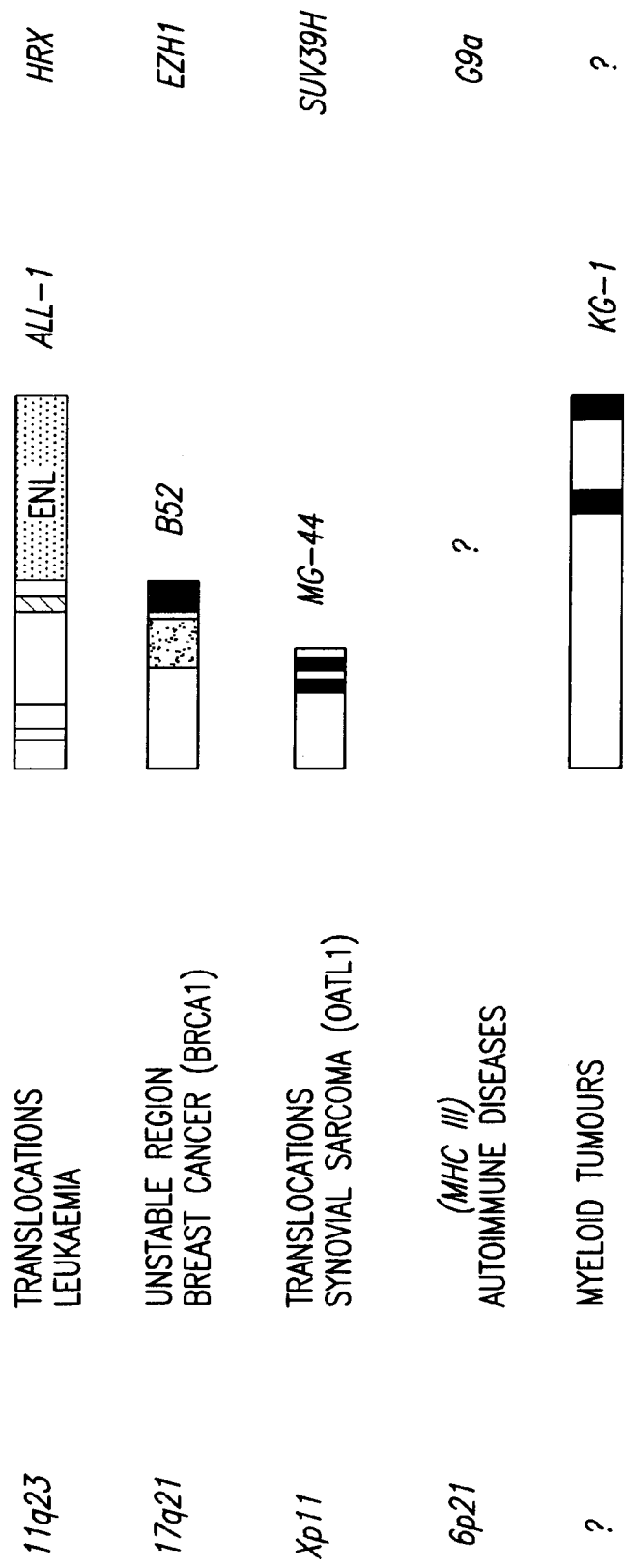
FIG. 3 shows the aberrant transcripts of human SET-domain genes. On the left of the figure is the position of the five currently known SET-domain genes on the appropriate chromosome. The names of the authentic genes in each case are given on the right side of FIG. 3. More specifically.

Starting from the sequence information of the conserved SET-domain, a human B-cell-specific cDNA library was screened, under reduced stringency, with a mixed *Drosophila*-DNA probe which codes for the SET-domains of E(z) and Su(var)3-9. From 500,000 plaques, 40 primary phages were selected. After another two rounds of screening, it became apparent that 31 phages code for authentic E(z)-sequences and 5 phages constitute E(z)-variants. By contrast, only two phages hybridized with the probe containing the SET-domain of Su(var)3-9 alone. The phage inserts were amplified by polymerase chain reaction (PCR) and analyzed by restriction mapping and partial sequencing. Representative cDNA inserts were subcloned and sequenced over their entire length. The 5'-ends were isolated by screening positive phages once more with 5'-DNA probes, whereupon, after subcloning, complete cDNAs were obtained.

The complete cDNA coding for the human homologue of E(z) was designated EZH2 (SEQ ID NO:1) and the DNA coding for the human homologue of Su(var)3-9 was designated SUV39H (SEQ ID NO:3). All in all, the identity of the amino acids between *Drosophila* and the human proteins amounts to 61% for EZH2 and 43% for SUV39H, whilst the C-terminal SET-domain is very highly conserved (88% for EZH2 and 53% SUV39H). Sequence comparison showed other clear regions of homology, e.g., a cysteine-rich domain in EZH2 and a Chromo-Box in SUV39H. (In polycomb, it was shown that the Chromo-Box is the essential domain for the interaction between DNA and chromatin (Messmer, et al., *Genes & Dev.* 6:1241–1254 (1992)). By contrast, the 207 amino acids which make-up the amino terminal GTP-binding motif of the *Drosophila* protein are absent from the human homologue SUV39H. A comparison of the amino acid sequences between *Drosophila* and the human genes is shown in FIGS. 1A–1B and 2A–2B. Moreover, another cDNA of the SET-domain family known as MG-44 (see below) also lacks the 5'-end of the *Drosophila* gene.

Since translational consensus sequences are also present in the environment of the start-ATG of human SUV39H-cDNA, even at the corresponding internal position in Su(var)3-9, the *Drosophila* protein ought to contain additional exons which become dispensable for function at a later stage of evolution. The correctness of this hypothesis can be confirmed by expressing human SUV39H-cDNA and cDNAs of Su(var)3-9 which are either complete or shortened at the 5'-end in *Drosophila*.

In addition to the human cDNA of SUV39H, the homologous locus was also isolated in the mouse, the sequence analysis and promoter structure of which clearly confirm the amino terminal shortening of mammal-homologous genes compared with *Drosophila* Su(var)3-9.

DNA blot analyses carried out within the scope of the present invention indicate that mammal-homologous genes of Su(var)3-9 are represented in mice and humans by individual loci, whereas mammal-homologous genes of E(z) are coded by two separate loci in mice and humans. The second human locus (known as EZH1) was confirmed by characterizing a small number of cDNA variants which differ in their 3'-flanking sequences from the majority of the clones isolated from the human cDNA library. The differences between EZH2 (SEQ ID NO:1) and EZH1 (SEQ ID NO:5) in the sequenced area are shown in FIG. 8. The SET-domain of EZH1 exhibits mutations compared with EZH2. Moreover, the EZH1 variant which was isolated (in all probability, an aberrantly spliced cDNA) carries a stop codon located in the reading frame which shortens the protein by 47 C-terminal amino acids. Sequence comparison of EZH1 (SEQ ID NO:5) with EZH2 (SEQ ID NO:1) and the finding that there are two separate E(z)-homologous loci in humans and in mice, lead one to conclude that gene duplication has occurred in mammals.

In the light of the knowledge of the nucleotide sequence of the SET domain genes, it is possible to produce the corresponding proteins derived from the cDNA sequences, which is also an object of the present invention, in recombinant form, by inserting the cDNAs coding for them in suitable vectors and expressing them in host organisms. The techniques used to produce recombinant proteins are well known to the skilled person and may be taken from relevant manuals (Sambrook, J., Fritsch, E. F. and Maniatis, T., 1989, Cold Spring Harbor Laboratory Press). The present invention thus relates, in another aspect, to recombinant DNA molecules, containing the DNA coding for EZH2 (SEQ ID NO:1) or variants thereof, SUV39H (SEQ ID NO:3) or variants thereof, or EZH1 (SEQ ID NO:5) or variants thereof, or another SET-dependent protein or variant thereof, expression control sequences functionally connected thereto, and the host organisms transformed therewith.

SET Domain Mutations and Functionality

In a comparison with cDNA sequences in the GeneBank databank, it was surprisingly found that certain cDNA partial sequences recorded in the databank, which are derived from aberrant transcripts in tumor tissues, constitute mutated versions of the cDNAs according to the invention. For example, in the search for BRCA1, a gene which indicates a predisposition to breast and ovarian cancer, a partial cDNA sequence with 271 nucleotides was isolated, known as B52, which codes for a mutated variant of the SET-domain and it was mapped on the human chromosome 17q21 (Friedman, et al., *Cancer Research* 54:6374–6382 (1994)). Within the scope of the present invention, it was surprisingly found that B52 shows 97% identity with the EZH1 cDNA variant according to the invention. EZH1 might possibly be a gene the reactivation of which plays a part in deregulated proliferation.

As another example, a cDNA (2,800 nucleotides; MG-44) was isolated from human chromosome Xp11 (Geraghty, et al., *Genomics* 16:440–446(1993)), a region which indicates a predisposition to degenerative disorders of the retina and synovial sarcoma. It was found, surprisingly, that this cDNA has 98% identity with the SUV39H cDNA according to the invention.

The new genes prepared within the scope of the present invention thus make it possible to infer a correlation between certain cancers and mutations in chromatin regulators. For example, in the case of MG-44 cDNA, as it has numerous point and frameshift mutations which interrupt the chromo- and SET-domains, it became possible for the first time, using the SUV39H cDNA according to the invention, to clarify a correlation between Su(var)3-9 and MG-44.

Apart from the sequences already mentioned, the GeneBank databank also records, as other human members of the SET-protein family, the well-documented human homologue of *Drosophila* trx, HRX/ALL-1 (Tkachuk, et al., *Cell* 71:691–700 (1992); Gu, et al., *Cell* 71:701–708 (1992)); a gene of unknown function known as G9a which is present in the human Major Histocompatibility Complex (Milner and Campbell, *Biochem J.* 290:811–818 (1993)); and thirdly, an unpublished cDNA (KG-1) which was isolated from immature myeloid tumor cells (Nomura, et al., Unpublished, GeneBank Accession Number:D31891 (1994)). Whereas G9a is currently the only human gene with a SET-domain for which no mutated version is known hitherto, KG-1 carries an insertion of 342 amino acids which cleaves the SET-domain into an amino-terminal half and a carboxy-terminal half. Probably, this KG-1 cDNA constitutes an aberrantly spliced variant since there are 5' and 3' consensus splicing sites at both ends of the insertion. In all, four of the five currently known human members of the SET-protein family have undergone changes, all of which mutate the SET-domain (HRX/ALL-1, EZH1/B52, SUV39H/MG-44 and KG-1). Moreover, in three cases, the corresponding human gene loci in the vicinity of translocational fracture points or unstable chromosomal regions have been mapped (HRX/ALL-1, EZH1/B52 and SUV39H/MG-44). See FIG. 3.

The fact that a mammalian gene of the SET-protein family, HRX/ALL-1, has been connected with translocation-induced leukaemogenesis (Tkachuk, et al., *Cell* 71:691–700 (1992); Gu, et al., *Cell* 71:701–708 (1992)) is a strong indication that proteins with the SET-domain are not only important regulators of development which co-determine chromatin-dependent changes in gene expression, but that, after mutation, they also disrupt normal cell proliferation.

Since all the mutations described hitherto interrupt the primary structure of the SET-domain, it is fair to assume that it is the SET-domain as such which plays a crucial part in the transition from the normal state into the transformed state. Furthermore, the SET-domain may have an important role in view of its evolutionary conservation in gene products which occurs from yeasts to humans.

To investigate the frequency with which the SET domain is subjected to specific mutations, it is possible to use the SET-specific DNA probes to analyze single-strand conformation polymorphisms (SSCP; Gibbons, et al., *Cell* 80:837–845 (1995)). Types of cancer in which SET-specific DNA probes can be used as diagnostic markers are breast cancer (EZH1; Friedman, et al., *Cancer Research* 54:6374–6382 (1994)), synovial sarcoma (SUV39H; Geraghty, et al., *Genomics* 16:440–446 (1993)) and leukaemias.

It has been assumed by other authors (DeCamillis, et al., *Genes & Dev.* 6:223–232 (1992); Rastelli, et al., *Embo J.* 12:1513–1522 (1993); Orlando and Paro, *Cell* 75:1187–1198 (1993)) that complexing between various members of heterochromatin proteins is essential for their functioning. In view of the availability of the SET domain genes according to the invention, it is possible to determine whether the SET region constitutes a domain which functions because of interactions or whether it contributes to the formation of multimeric heterochromatic complexes. Similarly, it is possible to determine whether the SET domain has an inhibitory function, similar to the amino-terminal BTB domain of various chromatin regulators, including the GAGA factor (Adams, et al., *Genes & Dev.* 6:1589–1607 (1992)).

Investigations which serve to analyze the function of the SET domain may be carried out, for example, by expressing cDNAs coding for human EZH2 or SUV39H, and providing an epitope against which antibodies are available in vitro and in tissue cultures. After immune precipitation with the appropriate epitope-specific antibodies, it is possible to establish whether EZH2 and SUV39H are able to interact with each other in vitro and whether complexing occurs in vivo between EZH2 and/or SUV39H with other chromatin regulators. In all, the analyses of interactions with EZH2 and SUV39H proteins provided with epitopes allow for further characterization of the function of the SET domain. This opens up possibilities of taking action against deregulated activity by, e.g., introducing dominant-negative variants of the SET domain cDNA sequences into the cell using gene-therapy methods. Such variants are obtained, for example, by first defining the functional domains of the SET proteins, e.g., the sequence portions responsible for the DNA/chromatin interaction or protein/protein interaction, and then expressing the DNA sequences shortened by the relevant domain(s), or sections thereof, in the cell in question in order to compete with the deregulated proliferation caused by the intact functional protein.

The availability of the cDNAs according to the invention also makes it possible to produce transgenic animals, e.g., mice, wherein SET domain genes can either be overexpressed ("gain-of-function") or wherein these genes can be switched off ("loss-of-function"). Such transgenic animals are also an object of the present invention.

In particular, the "gain-of-function" analyses, in which alleles of the genes according to the invention are introduced into the mouse, provide final conclusions as to the causative participation of EZH2 and SUV39H in the chromatin-dependent requirements of tumor formation. For the "gain-of-function" analysis, the complete cDNA sequences of human EZH2 and SUV39H, and mutated versions thereof, such as EZH1/B52 and MG-44, may be driven by vectors which allow high expression rates, e.g., plasmids with the human β-actin promoter, and by the enhancer of the heavy chain of immunoglobulins (Eµ) and also by Moloney virus enhancers (Mo-LTR). Recently, it was shown that the Eµ/Mo-LTR-dependent overexpression of the bmi gene, which, in common with EZH2, belongs to the Pc group of negative chromatin regulators, is sufficient to produce lymphomas in transgenic mice (Alkema, et al., *Nature* 374: 724–727 (1995)).

In the "loss-of-function" analyses, the endogenous mouse loci for EZH1 and SUV39H are interrupted by homologous recombination in embryonic stem cells, thus, it is possible to determine whether the loss of the in vivo gene function leads to abnormal development of the mouse.

As a result of these in vivo systems, the activity of EZH2 and SUV39H can be confirmed. These systems also form the basis for animal models in connection with human gene therapy.

For a detailed analysis of the function of the cDNAs according to the invention or partial sequences thereof with respect to the diagnostic use of SET domain gene sequences, within the scope of the present invention, homologous murine cDNAs were isolated from EZH1 and SUV39H. When using a mouse-specific DNA probe coding for the SET domain in "RNAse protection" analyses to investigate the EZH1 gene activity during normal mouse development, a somewhat broad expression profile became apparent which is similar to that of the bmi gene (Haupt, et al., *Cell* 65:153–763 (1991)). The analyses carried out with the murine sequences were expanded with human sequences to compare the quantities of RNA between immature precursor cells, tumor cells and differentiated cells in various human cell culture systems.

SUV39H Proteins

Overexpression studies with human SUV39H mutants indicate a dominant interference with higher-order chromatin organization that, surprisingly, suggests a functional relationship between the SET domain and the distribution of phosphorylated (at seine 10) H3 (Melcher, M., et al., *Mol Cell Biol* 20:3728–41 (2000)). The experiments of the present invention, as shown in the Examples, show that mammalian SUV39H1, or other SUV39H proteins, are SET domain-dependent, H3-specific histone methyltransferases (HMTases) which selectively methylate lysine 9 of the H3 N-terminus. See FIGS. 9A–9B and 10A–10C. Methylation of lysine 9 negatively regulates phosphorylation of seine 10 and reveals a histone code that appears intrinsically linked to the organization of higher-order chromatin.

In the present invention, the function of members of the SU(VAR)3-9 protein family was investigated with the view to develop novel strategies to interfere with chromosome stability and high fidelity chromosome segregation. Such strategies can be employed in therapies for the treatment of conditions in which aberrant gene expression and genomic instability through chromosome missegregation are causally involved. (The term "high fidelity chromosome segregation" implies successful segregation of chromosomes resulting in the maintenance of a stable karyotype).

Figure 10A:
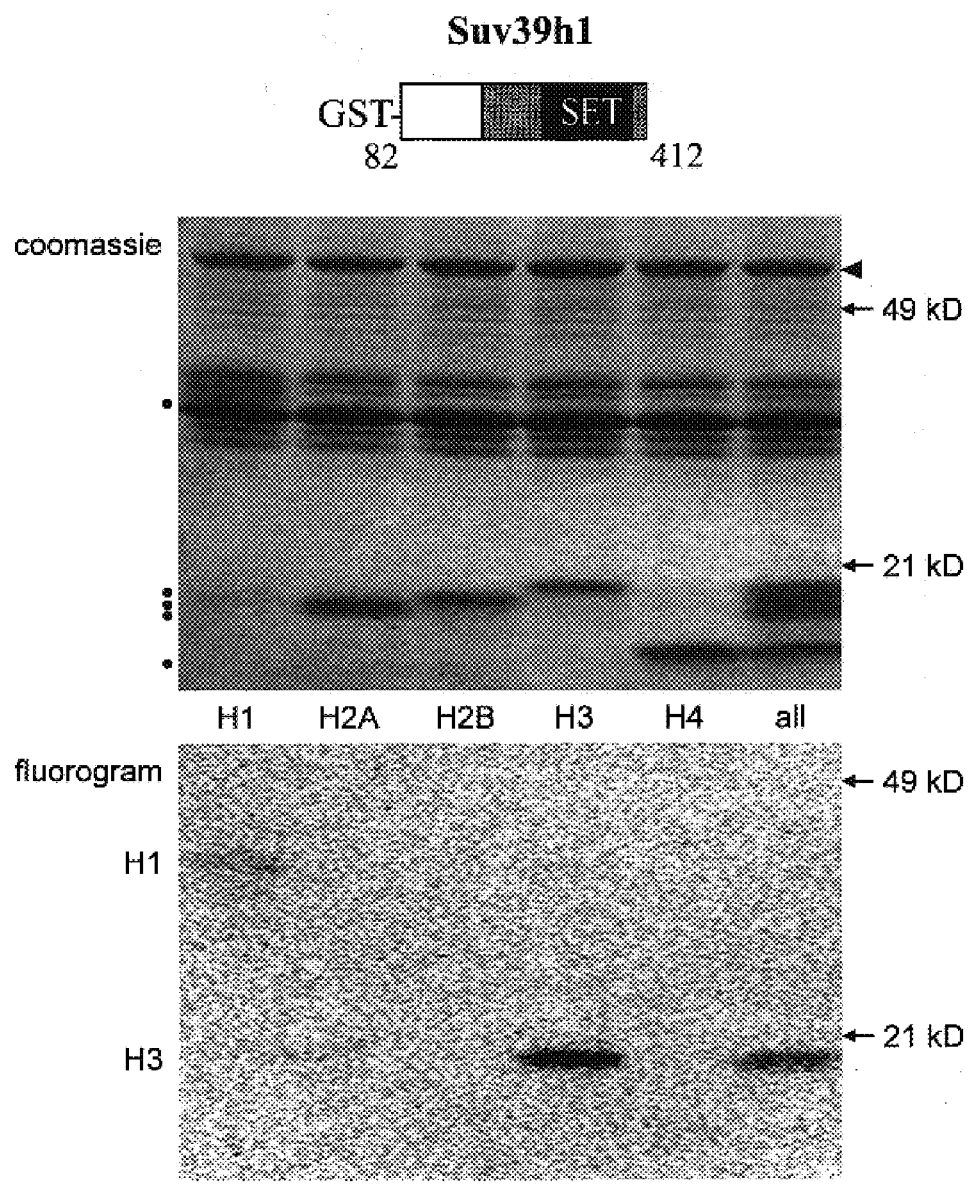
FIGS. 10A–C illustrate that lysine 9 of the H3 N-terminus is the major site for in vitro methylation by recombinant Suv39h1. More specifically, for FIG. 10A, approximately 10 μg of murine GST-Suv39h1(aa 82-412) were used in in vitro HMTase reactions with individual histones as outlined in FIGS. 9A–9B. The top panel is the Coomassie stain and the bottom panel is the fluorogram. For FIG. 10B, in vitro methylation assays using GST-Suv39h1(aa 82-412) as enzyme and the indicated N-terminal peptides of wild-type H3, mutated H3 (K9L), CENP-A, macroH2A or insulin as substrates.
Figure 10B:
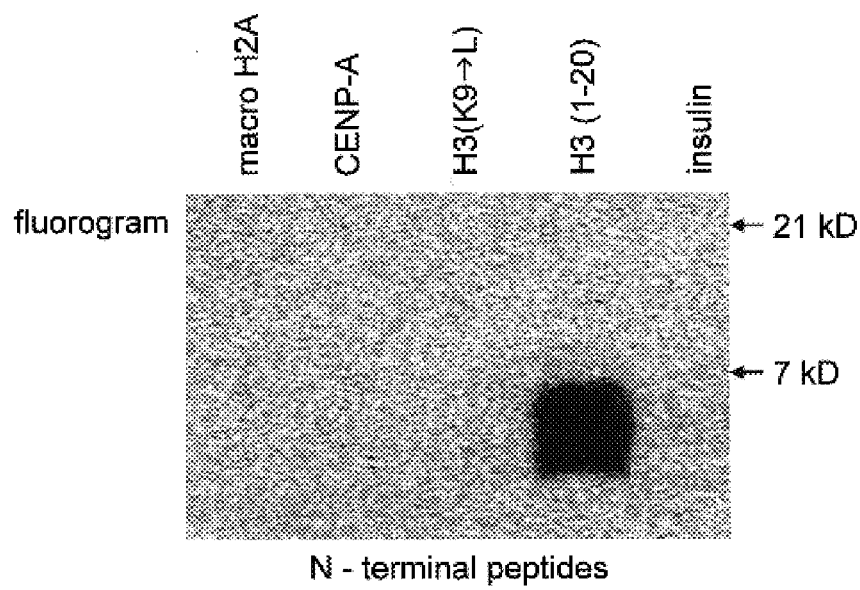
Figure 10C:
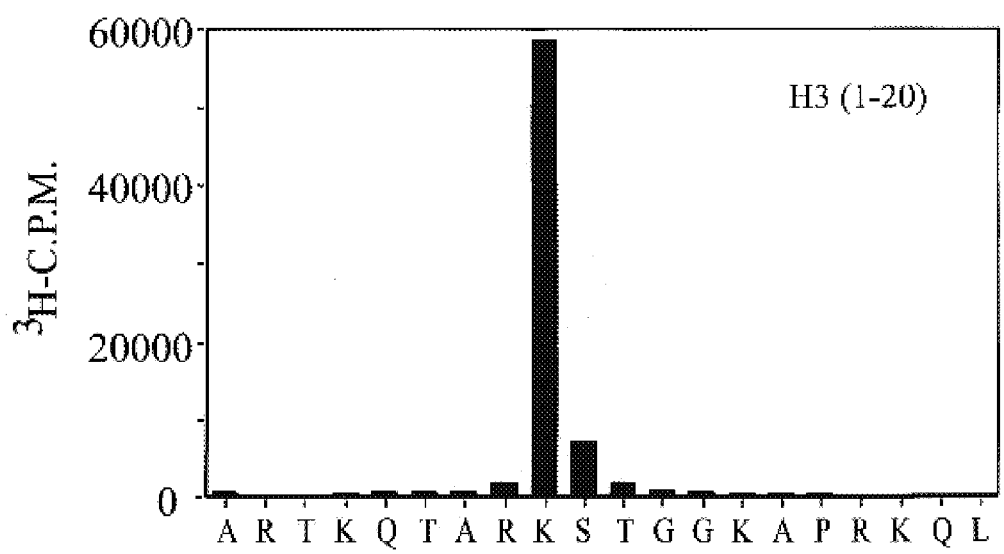

To this end, in a first step, bioinformatic techniques were applied. Using the SET domains of the SU(VAR)3-9 protein family as a starting alignment, distant sequence and secondary structure similarities to six plant protein methyltransferases were detected. To investigate whether the SET domain of human SUV39H1 has enzymatic activity, histones were tested as possible substrates for in vitro methylation. The obtained results demonstrate that SUV39H1 harbors an intrinsic histone methyltransferase activity and suggest that this HMTase activity resides in the C-terminal SET domain. Experiments indicated that the HMTase activity of mammalian SU(VAR)3-9 related proteins is selective for H3 under the chosen assay conditions. To examine this finding in more detail, in vitro methylation reactions were performed with individual histones. It could be shown that H3 is specifically methylated by GST-Suv39h1 (aa 82-412), whereas no signals are detected with H2A, H2B or H4. Methylation of H3 has been shown to occur predominantly at lysine 4 in a wide range of organisms, as well as at lysine 9 in HeLa cells, although the responsible HMTase(s) have yet to be defined. To investigate the site utilization profile of Suv39h1, unmodified peptides comprising the wild-type H3 N-terminus and a mutant K9L peptide were tested as substrates. Additionally, insulin and peptides comprising the N-termini of CENP-A and macroH2A were included. These in vitro assays revealed selective methylation of the wild-type H3 peptide. The data obtained also suggested that the H3 N-terminus is a preferred residue for Suv39h1-dependent HMTase activity. To more definitively determine this site preference, the wild-type H3 N-terminal peptide was in vitro methylated by GST-Suv39h1 (aa 82-412), using S-adenosyl-(methyl-$^3$H)-L-methionine. The labeled peptide, purified by reverse-phase HPLC, was then directly microsequenced, and $^3$H-incorporation associated with each individual amino acid was analyzed. The results confirmed selective transfer of methyl-label to lysine 9, demonstrating that Suv39h1 is a highly site-specific HMTase for the H3 N-terminus in vitro (FIG. 10C). The identification of members of the SU(VAR) 3-9 protein family, exemplified by human SUV39H1, murine Suv39h1 and murine Suv39h2, as K9 specific histone H3 MTases is the prerequisite for designing assay methods that allow for finding compounds altering, in particular interfering with, chromosome stability, which is the basis for novel therapeutic approaches. Suv39h proteins and other methyl transferases with Suv39h-like activity are useful in a method for identifying compounds that have the ability of modulating chromosome stability in plant or animal cells. This method is characterized in that a MTase with Suv39h-like MTase activity is incubated, in the presence of the substrate(s) for its enzyme activity and optionally its co-factor(s), with test compounds and that the modulating effect of the test compounds on the MTase activity of the MTase is determined.

Since it has been shown in the present invention that recombinant Suv39h retains MTase activity, most preferably, recombinant enzymes are employed. Suv39h or Suv39h variants can be produced recombinantly according to standard methods by expression in suitable hosts, e.g., bacteria, yeast, insect or eucaryotic cells and purified, e.g., on glutathione-agarose columns if it has been tagged with GST. For testing the compounds for their effect on Suv39h activity, the assay comprises, as its essential features, incubating a histone H3 protein or histone H3 N-terminal fragment including K9, a methyl donor, S-adenosyl-L-Methionine with a preparation containing a Suv39h MTase activity and determining MTase activity in the presence or absence of a test substance.

MTase substrates useful in the method of the invention may be those equivalent to or mimicking the naturally occurring substrates, e.g., biochemically purified histone H3, recombinantly produced histone H3, or a histone H3 peptide that contains the K9 methylation site, or other yet to be identified proteins which act as substrates for Suv39h MTases. Additional novel Suv39h substrates can be identified by bioinformatic/biochemical techniques and tested using the biochemical assays described herein. These novel Suv39h substrates can be identified by co-immunoprecipitation techniques. Suv39h proteins or tagged versions of Suv39h proteins could be immunoprecipitated with specific anti-sera and interacting proteins identified by mass spectroscopy techniques. A yeast two-hybrid screen using Suv39h proteins or portions of Suv39h proteins as a bait could also be employed to identify novel interacting protein from a variety of cDNA libraries.

In a preferred embodiment, the histone H3 fragment ARTKQTARKSTGGKAPRKQL (SEQ ID NO:19) is employed. Alternatively, a similar peptide may be used for which the MTase has increased affinity/activity. The methyl donor preferably carries a detectable label, e.g., a radioactive or a chromogenic label, which can be quantified upon transfer to the substrate. Preferably, the methyl donor is the natural methyl donor S-adenosyl-L-Methionine. Alternatively to using a labeled methyl donor, the substrate, upon methylation by the enzyme, serves as an epitope which can be recognized by a specific antibody and hence used for quantification by standard immunoassay techniques, e.g., ELISAs. Antibodies useful in this type of assay can be obtained by using the methylated substrate, preferably a small peptide, e.g., the K9 methylated peptide ARTKQTARKSTGGKAPRKQL (SEQ ID NO:19) as an antigen and obtaining polyclonal or monoclonal antibodies according to standard techniques. For small scale applications, the screening method can be based on the principal of the assay as described in Example 3. In a preferred embodiment, the method is performed on a high-throughput scale. For this embodiment the major assay components, in particular Suv39h, are employed in recombinant form. The thus obtained recombinant protein can then be used in an inhibitor screen. For the high-throughput format, the screening methods to identify MTase inhibitors, are carried out according to standard assay procedures. Such assays are based on the catalytic transfer, mediated by Suv39h or a Suv39h variant, of a methyl group from a substrate to a histone H3 peptide. To achieve this, the substrate histone H3 peptide would be immobilized and incubated with recombinant Suv39h or Suv39h variant and a chromogenic methyl donor or radioactively labeled methyl donor or a unmodified methyl donor. Upon transfer of the methyl group to the histone H3 peptide by Suv39h, the chromogenic methyl donor would change color which and can be quantified or the radioactive methyl group transferred to the substrate quantified or the methylation of the substrate quantified by ELISA using an antibody specific for the methylated substrate. If a test substance is an inhibitor of the MTase activity, there will be, depending on the detection system and depending on whether the test substance has an inhibiting or an activating effect, a decrease or an increase in the detectable signal. In the high-throughput format, compounds with a modulating effect Suv39h MTase activity can be identified by screening test substances from compound libraries according to known assay principles, e.g., in an automated system on microtiter plates.

Applications for Therapy

On the basis of the criteria laid down within the scope of the present invention, it transpires that the genes which have a SET domain are involved in the chromatin-dependent occurrence of deregulated proliferation. These genes or the cDNAs derived therefrom, or partial or mutated sequences thereof, can thus be used in the treatment and diagnosis of diseases which can be attributed to such proliferation. Specifically, oligonucleotides coding for the SET domain as such or parts thereof may be used as diagnostic markers in order to diagnose certain types of cancer in which the SET domain is mutated.

The DNA sequences according to the invention, or sequences derived therefrom, e.g., complementary antisense oligonucleotides, may be used in gene therapy—depending on whether the disease to be treated can be put down to deregulation of chromatin as a result of the absence of the functional gene sequence or as a result of overexpression of the corresponding gene(s)—by introducing the functional gene sequence, by inhibiting gene expression, e.g., using antisense oligonucleotides, or by introducing a sequence coding for a dominant-negative mutant. For example, as SUV39H is required to maintain a stable karyotype as described above, it can be considered as possessing tumor suppressor gene activity. If SUV39H mutations are factors underlying cellular transformation events, the re-introduction of a wild type SUV39H gene by gene therapy may result in increased genomic stability delaying or inhibiting cancer progression.

The inventive DNA molecules may be administered, preferably in recombinant form as plasmids, directly or as part of a recombinant virus or bacterium. In theory, any method of gene therapy may be used for therapy of cancer based on DNA, e.g., on SUV39H DNA, both in vivo and ex vivo. Thus, the DNA sequences in question may be inserted into the cell using standard processes for the transfection of higher eukaryotic cells, which may include gene transfer using viral vectors (retrovirus, adenovirus, adeno-associated virus, vaccinia virus or Listeria monocytogenes) or using non-viral systems based on receptor-mediated endocytosis. Surveys of the common methods are provided by, for example, Mitani, K. and Caskey, C. T., *Trends in Biotechnology* 11:162–166; Jolly, D., *Cancer Gene Therapy* 1:51 (1994); Vile, R. and Russel, S;, *Gene Therapy* 1:88 (1994); Tepper, R. I. and Mule, J. J., *Human Gene Therapy* 5:153 (1994); Zatloukal, K, et al., *Gene* 135:199 (1993); WO 93/07283. Examples of in vivo administration are the direct injection of "naked" DNA, either by intramuscular route or using a gene gun. Moreover, synthetic carriers for nucleic acids such as cationic lipids, microspheres, micropellets or liposomes may be used for in vivo administration of nucleic acid molecules coding for the SUV39H polypeptide.

To inhibit the expression of the genes according to the invention, it is also possible to use lower-molecular substances which interfere with the machinery of transcription. After analyzing the 5'-regulatory region of the genes, it is possible to screen for substances which wholly or partially block the interaction of the relevant transcription factors with this region by, e.g., using the method described in WO 92/13092.

Inhibition of deregulated proliferation may also act on the gene product, by therapeutically using the corresponding antibodies against the EZH2- or SUV39H-protein, preferably human or humanized antibodies. Such antibodies are produced by known methods, e.g., as described by Malavsi, F. and Albertini, A., *TIBTECH* 10:267–269 (1992), or by Rhein, R., *The Journal of NIH Res.* 5:40–46 (1993). Thus, the invention also relates to antibodies against EZH2 or SUV39H or other SET-dependent proteins which may be used therapeutically or diagnostically.

As another therapeutic approach, by providing a method to identify compounds which exert their effect by directly modulating, in particular, by inhibiting, SUV39H, for example, a novel approach for inhibiting the proliferation of rapidly dividing animal cells, in particular tumor cells, is provided. Compounds identified in the above-described assays have the ability to modulate chromosome stability by modulating the MTase activity of SUV39H. Compounds, which act as modulators of SUV39H, can also be used in human therapy, in particular cancer therapy.

The efficacy of compounds identified as SUV39H modulators can be tested for in vivo efficacy in mammalian cells with SUV39H double null cells serving as a positive control. Effective compounds should interfere with chromosome stability which can be measured by karyotyping, e.g., by analyzing DNA content by FACS, or by standard cytological techniques. Substances whose potential for therapeutic use has been confirmed in such secondary screen can be further tested for their effect on tumor cells.

To test the inhibition of tumor cell proliferation, primary human tumor cells may be incubated with the compound identified in the screen and the inhibition of tumor cell proliferation tested by conventional methods, e.g., bromodesoxy-uridine or $^3$H incorporation. Compounds that exhibit an anti-proliferative effect in these assays may be further tested in tumor animal models and used for the therapy of tumors.

Toxicity and therapeutic efficacy of the compounds identified as drug candidates by the methods described above can be determined by standard pharmaceutical procedures, which include conducting cell culture and animal experiments to determine the $IC_{50}$, $LD_{50}$ and $ED_{50}$. The data obtained may be used for determining the human dose range, which will also depend on the dosage form (tablets, capsules, aerosol sprays, ampules, etc.) and the administration route (oral, buccal, nasal, parenteral, rectal, etc.). A pharmaceutical composition containing the compound as the active ingredient may be formulated in a conventional manner using one or more physiologically active carriers and excipients. Methods for making such formulations can be found in manuals, e.g., "Remington Pharmaceutical Sciences."

SUV39H mediates dynamic transitions in higher order mammalian chromatin in part through its intrinsic HMTase activity. K9 methylation of histone H3 (K9-Me) represents an important epigenetic imprint for chromosome dynamics during cell division. Antibodies specific for K9-Me could be used to screen cells/patients for heterochromatin based genome instabilities. In essence, K9-Me specific anti-sera can be used a diagnostic tool for several potential human diseases.

Further, differences in the transcription level of SET domain RNAs between normal and transformed cells can be used as diagnostic parameters for diseases in which the expression of SET domain genes is deregulated. To find out whether the SET domain is accordingly suitable as a diagnostic tumor marker for specific cancers or as a general diagnostic parameter, it is possible to use current methods for determining the RNA concentration, as described in the relevant laboratory manuals (Sambrook, J., Fritsch, E. F. and Maniatis, T., 1989, Cold Spring Harbor Laboratory Press) such as Northern Blot, S1-nuclease protection analysis or RNAse protection analysis.

The following examples are provided by way of illustration to further describe certain preferred embodiments of the invention, and are not intended to be limiting of the present invention, unless specified.

EXAMPLES

Example 1

Preparation of a cDNA Library

Human B-cell-specific cDNA library as described by Bardwell and Treisman, *Genes & Dev.* 8:1644–1677 (1994), was prepared by isolating poly(A)$^+$-RNA from human BJA-B-cells, reverse-transcribing it by poly(dT)$_{15}$, priming and converting it into double-stranded cDNA. After the addition of an EcoRI adapter of the sequence 5' AATTCTC-GAGCTCGTCGACA (SEQ ID NO:6), the cDNA was ligated into the EcoRI site of the bacteriophage gt10. The propagation and amplificiation of the library were carried out in *E. coli* C600.

Preparation of DNA Probes

*Drosophila* DNA probes coding for the conserved SET domains of E(z) and Su(var)3-9 were prepared on the basis of the published *Drosophila* sequences (Jones and Gelbart, *MCB* 13(10):6357–6366 (1993); Tschiersch, et al., *Embo J.* 13(16):3822–3831 (1994)) by polymerase chain reaction (PCR): 1 µg of *Drosophila melanogaster*-DNA (Clontech) was subjected with the two primers, E(z) 1910 (5'ACT-GAATTCGGCTGGGGCATCTTTCTTAAGG) (SEQ ID NO:7) and E(z) 2280 (5' ACTCTAGACAATTTC-CATTTCACGCTCTATG) (SEQ ID NO:8), to PCR amplification (35 cycles of 30 sec at 94° C., 30 sec at 55° C. and 30 sec at 72° C.). The corresponding SET domain probe for Su(var)3-9 was amplified from 10 ng of plasmid DNA (Tschiersch et al., 1994; clone M4) with the pair of primers suvar.up (5' ATATAGTACTTCAAGTCCATTCAAAA-GAGG) (SEQ ID NO:9) and suvar.dn (5' CCAGGTACCGT-TGGTGCTGTTTAAGACCG) (SEQ ID NO:10), using the same cycle conditions. The SET domain DNA fragments obtained were gel-purified and partially sequenced in order to verify the accuracy of the amplified sequences.

Screening the cDNA Library

5×10$^5$ plaque forming units (pfu) were incubated with 5 ml of culture of the bacterial host strain of *E. coli* C600 (suspended at an optical density OD$_{600}$ of 0.5 in 10 mM MgSO$_4$) at 37° C. for 15 min and then poured onto a large (200 mm×200 mm) preheated LB dish. After growing overnight at 37° C., the phages were absorbed on a nylon membrane (GeneScreen). The membrane was left floating with the side containing the absorbed phages facing upwards, for 30 sec in denaturing solution (1.5 M NaCl, 0.5 M NaOH), then immersed for 60 sec in denaturing solution and finally neutralized for 5 min in 3 M NaCl, 0.5 M Tris (pH 8). The membrane was then briefly rinsed in 3×SSC and the phage DNA was fixed on the nylon filter by UV-crosslinking. The filter was prehybridized for 30 min. at 50° C. in 30 ml of church buffer (1% BSA, 1 mM EDTA and 0.5 M NaHPO$_4$, pH 7.2), then 2×10$^6$ cpm of the radiolabeled DNA probe mixture of E(z)-SET and Su(var)3-9-SET were added. The DNA probes were prepared by random priming using the RediPrime Kit (Amersham). Hybridization was carried out overnight at 50° C. After the hybridizing solution had been removed, the filter was washed for 10 sec in 2×SSC, 1% SDS at ambient temperature, then for 10 sec at 50° C. The filter was wrapped in Saranwrap and subjected to autoradiography using an intensifier film.

Positive phage colonies were identified on the original plate by matching the autoradiogram and the corresponding agar fragments were removed using the larger end of a Pasteur pipette. The phage pool was eluted overnight at 4° C. in 1 ml SM-Buffer (5.8 g NaCl, 2 g MgSO$_4$—H$_2$O, 50 ml Tris (pH 7.5), 5 ml 2% gelatine on 1 l H$_2$O), containing a few drops of CHCl$_3$. The phage lysate was plated out for a second and third round of screening in order to obtain individual, well isolated positive plaques (20 to 100 plaques per plate in the third round).

Sequence Analysis

The cDNA inserts from recombinant phages were subcloned into the polylinker of pBluescript KS (Stratagene) and sequenced in an automatic sequencer (Applied Biosystems) using the dideoxy method. The complete sequence of at least two independent isolates per gene obtained was determined by primer walking. The sequences were analyzed with the GCG-Software package (University of Wisconsin), and the investigation for homology was carried out using the "Blast and fasta" or "tfasta" network service. The complete sequences of EZH2 (SEQ ID NO:1) and SUV39H (SEQ ID NO:3) are shown in FIGS. 6A–6C and 7A–7B.

Examples 2–4

Materials and Methods

Sequence Alignments and Secondary Structure Predictions

The SET domains of human SUV39H1, *Drosophila* Su(var)3-9 and *S. pombe* CLR4 were used as a multiple starting alignment for database similarity searches using Profile, hidden Markov and position-specific iterative BLAST methods (representative listings are available from the SET domain page of the SMART WWW-server). These searches revealed significant similarities to six plant proteins (accession numbers Q43088, O65218, P94026, O80013, AAC29137 and AC007576__12) described as putative lysine N-methyltransferases. For example, a PSI-BLAST search with the *S. pombe* hypothetical protein SPAC3c7.09 as query identified these plant sequences and well-known SET domain sequences within ten rounds using an E-value inclusion threshold of 0.001. The same search also revealed the presence of a SET domain in YHR109w (which is known to encode a cytochrome c MTase) within three rounds. Consensus secondary structures were predicted by described algorithms.

Epitope-Tagged SUV39H1 Proteins in HeLa Cells

The HeLa cell lines overexpressing full-length (myc)$_3$-SUV39H1 (aa 3-412) or (myc)$_3$-Nchromo (aa 3-118) have been described. Nuclear extracts were immunoprecipitated with anti-myc antibody beads, and approximately 1–3 μg of matrix-bound (myc)$_3$-tagged SUV39H1 proteins were used for in vitro HMTase assays.

Generation and Purification of GST-Fusion Proteins

The GST-Suv1(aa 82-412) product expressed from the pGEX-2T vector (Pharmacia) as a glutathione-S-transferase (GST) fusion protein has been described. Additional GST constructs were generated by transferring BamHI-EcoRI PCR amplicons into pGEX-2T. All constructs were confirmed by sequencing. Recombinant proteins were expressed in 11 cultures of *E. coli* strain BL21 and solubilized in 10 ml RIPA buffer ((20 mM Tris (pH 7.5), 500 mM NaCl, 5 mM EDTA, 1% NP-40, 0.5% sodium deoxycholate) containing a full set of protease inhibitors (Boehringer Mannheim) and lysozyme (5 mg/ml; Sigma)) by freeze-thawing in liquid N$_2$, followed by sonication. Soluble proteins were cleared by centrifugation, purified with 800 ml glutathione Sepharose beads (Pharmacia) and washed twice in RIPA buffer. Protein concentration was determined by Coomassie staining of SDS-PAGE gels. Matrix-bound fusion proteins were used immediately for in vitro HMTase assays or stored at 4° C.

In Vitro Histone Methyltransferase (HMTase) Assay

In vitro HMTase reactions were modified based on described protocols and carried out in a volume of 50 μl of methylase activity buffer (MAB: 50 mM Tris (pH 8.5), 20 mM KCl, 10 mM MgCl$_2$, 10 mM b-ME, 250 mM sucrose), containing 10 μg of free histones (mixture of H1, H3, H2B, H2A and H4; Boehringer Mannheim) as substrates and 300 nCi S-adenosyl-(methyl-$^{14}$C)-L-methionine (25 mCi/ml) (Amersham) as methyl donor. 10 μg of matrix-bound GST-fusion proteins were routinely used to assay for HMTase activity. After incubation for 60 min. at 37° C., reactions were stopped by boiling in SDS loading buffer, and proteins were separated by 15% or 18% SDS-PAGE and visualized by Coomassie staining and fluorography. HMTase assays with individual histones (Boehringer Mannheim), insulin (Sigma) or N-terminal peptides were performed with 5 μg of substrate. The following peptides were used: wild-type N-terminus of human histone H3 (ARTKQTARKSTG-GKAPRKQL) (SEQ ID NO:19) and mutant peptide which changes lysine 9 (bold) to leucine; N-terminus of human CENP-A (MGPRRRSRKPEAPRRRSPSP) (SEQ ID NO:20); N-terminus of rat macro-H2A (MSSRGGKKKST-KTSRSAKAG) (SEQ ID NO:21). Peptide microsequencing of the in vitro methylated wild-type H3 N-terminal peptide and determination of $^3$H-incorporation of individual amino acids by scintillation counting was done as described.

Example 2

Sequence Similarity of SET Domains with Plant Methyltransferases

Using the SET domains of the SU(VAR)3-9 protein family as a starting alignment, significant sequence and secondary structure similarities (see Methods above) to six plant protein methyltransferases were detected. Although some of these plant sequences have been classified as potential histone lysine N-methyltransferases, only one had been functionally characterized, but was found to lack HMTase activity. Detected were amino acid and secondary structure (β-sheet (b) or α-helix (h)) similarities of the C-terminal halves of SET domain sequences from human SUV39H1 (AF019968), murine Suv39h1 (AF019969), murine Suv39h2 (AF149205), *Drosophila* Su(var)3-9 (P45975), a *C. elegans* Su(var)3-9-like ORF C15H11.5 (CAB02737), *S. pombe* CLR4(O74565), human EZH2 (Q15910), the human trithorax homologue HRX (Q03164), and MTases from *P. sativum* (rubisco ls-MT; Q43088) and *A. thaliana* (O65218). The plant MTase sequences contain an insertion of approximately 100 amino acids in the middle of the SET domain.

Example 3

HMTase Activity of Transfected and Recombinant SUV39H1 and Suv39h1 Proteins

Figure 9A:
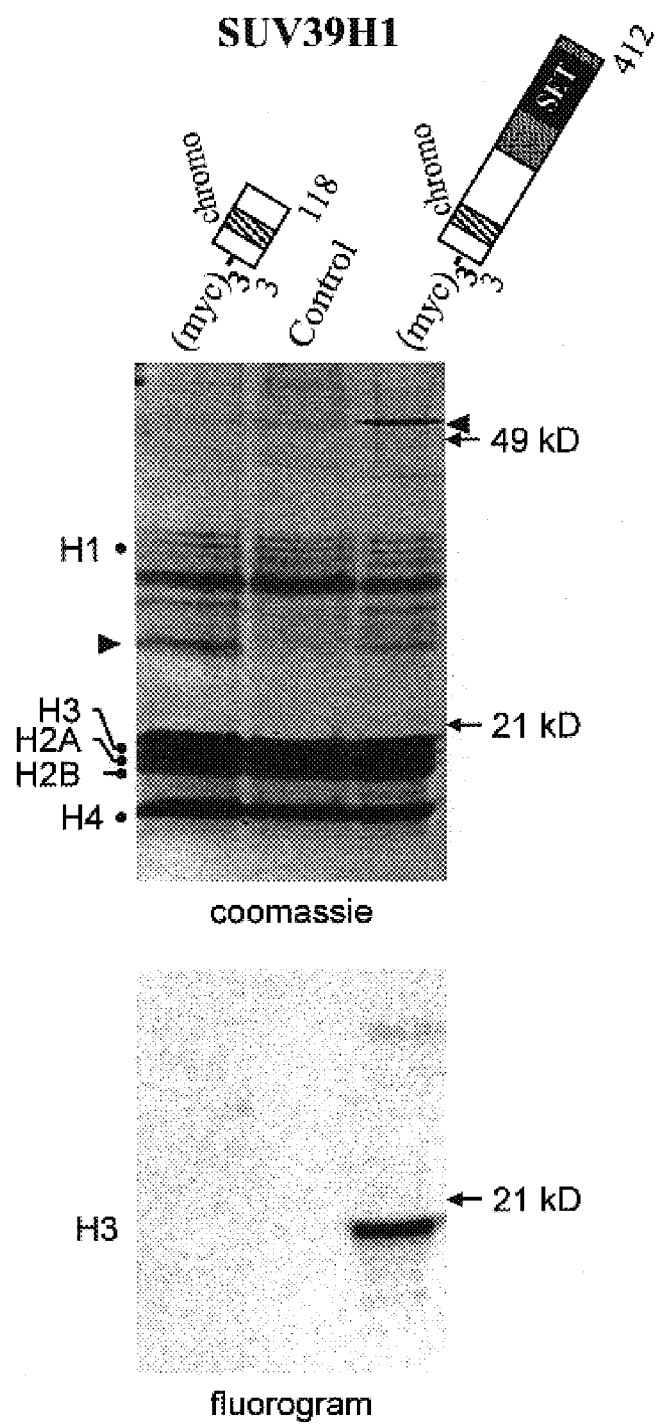
FIGS. 9A–B illustrate HMTase activity of transfected and recombinant SUV39H1/Suv39h1 proteins. More specifically, in FIG. 9A, triple myc-tagged full-length human SUV39H1 (aa 3-412) or a C-terminally truncated SUV39H1 protein (aa 3-118) were immunoprecipitated from 'stably' transfected HeLa cell lines with anti-myc antibody beads and used in in vitro HMTase reactions with free histones as substrates and S-adenosyl-(methyl-$^{14}$C)-L-methionine as methyl donor. The Coomassie stain (top panel) shows purified proteins by arrowheads and free histones by dots. Fluorography (bottom panel) indicates HMTase activity of $(myc)_3$-SUV39H1 (aa 3-412).
Figure 9B:
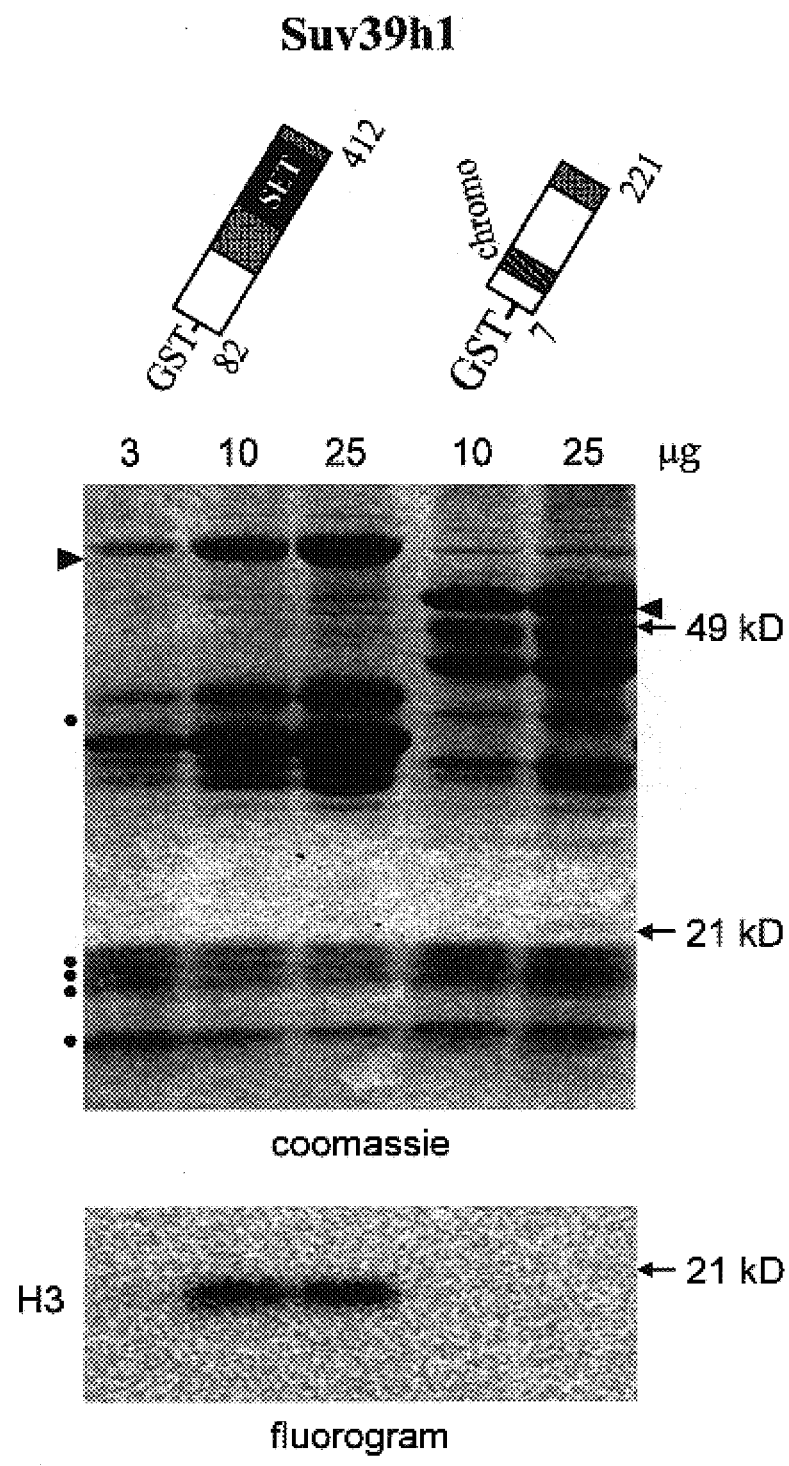

To investigate whether the SET domain of human SUV39H1 has enzymatic activity, histones were tested as possible substrates for in vitro methylation. Using HeLa cell lines 'stably' expressing triple myc-tagged full-length SUV39H1 (aa 3-412), the ectopic protein was enriched from nuclear extracts by immunoprecipitation with anti-myc beads (see FIG. 9A, arrowhead top panel) and probed for activity to transfer a labeled methyl group from S-adenosyl-(methyl-$^{14}$C)-L-methionine to free histones according to described conditions. Reaction products were separated by SDS-PAGE and visualized by fluorography, indicating selective transfer of the methyl-label to H3 (FIG. 9A, bottom panel). By contrast, no signals were detected with extracts from a HeLa cell line that expresses only the N-terminal third of SUV39H1 (aa 3-118) or with extracts from HeLa control cells. To confirm that the HMTase activity is an intrinsic property of SUV39H1 and not mediated by a SUV39H1-associated factor, the in vitro HMTase reactions was repeated with recombinant products that were purified as GST-fusion proteins from *E. coli* (see FIG. 9B, arrowheads top panel). For this analysis, murine Suv39h1, which is 95% identical to human SUV39H1 (Aagaard, L., et al., *EMBO J.* 18:1923–1938 (1999)) was used. A purified GST-product comprising aa 82-412 maintained HMTase activity (although at a reduced level as compared to transfected SUV39H1), whereas a purified GST-product comprising aa 7-221 proved negative, even at higher protein concentrations (FIG. 9B, bottom panel). These results suggest that the HMTase activity resides in the C-terminal SET domain.

Example 4

Lysine 9 of the H3 N-Terminus is the Major Site for In Vitro Methylation by Recombinant Suv39h1

The above Examples indicated that the HMTase activity of mammalian Su(var)3-9 related proteins is selective for H3 under the chosen assay conditions. To examine this finding in more detail, in vitro methylation reactions were performed with individual histones, using GST-Suv39h1(aa 82-412) as an enzyme. As shown in FIG. 10A, H3 is specifically methylated by GST-Suv39h1(aa 82-412), whereas no signals are detected with H2A, H2B or H4. A weak signal is present if H1 was used as the sole substrate; the significance of H1 methylation remains to be determined. Methylation of H3 has been shown to occur predominantly at lysine 4 in a wide range of organisms, as well as at lysine 9 in HeLa cells, although the responsible HMTase(s) have yet to be defined. To investigate the site utilization profile of Suv39h1, unmodified peptides comprising the wild-type H3 N-terminus (aa 1-20) and a mutant K9L peptide, changing lysine 9 to leucine were tested as substrates. Additionally, insulin and peptides comprising the N-termini of CENP-A and macroH2A were included. Peptides were in vitro methylated by GST-Suv39h1 (aa 82-412), and reaction products were separated by high percentage SDS-PAGE and visualized by fluorography. These in vitro assays revealed selective methylation of the wild-type H3 peptide, whereas no signals were detected with the CENP-A or macroH2A peptides, or with insulin (see FIG. 10B). Importantly, the mutated H3 (K9L) peptide was not a substrate, suggesting that lysine 9 of the H3 N-terminus is a preferred residue for Suv39h1-dependent HMTase activity. To more definitively determine this site preference, the wild-type H3 N-terminal peptide was in vitro methylated by GST-Suv39h1(aa 82-412), using S-adenosyl-(methyl-$^3$H)-L-methionine. The labeled peptide, purified by reverse-phase HPLC, was then directly microsequenced, and $^3$H-incorporation associated with each individual amino acid was analyzed by scintillation counting. The results confirmed selective transfer of methyl-label to lysine 9 (see FIG. 10C), demonstrating that Suv39h1 is a highly site-specific HMTase for the H3 N-terminus in vitro.

The invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

REFERENCES

Aagaard, L., et al., *EMBO J.* 18:1923–1938 (1999)
Aasland, R., and Stewart, A. F., *Nucl. Acids Res.* 23:3168–3174 (1995)
Allshire, R. C., et al., *Genes Dev.* 9:218–233 (1995)
Altschul, S. F., et al., *Nucl. Acids Res.* 25:3389–3402 (1997)
Baksa, K., et al., *Genetics* 135:117–1125 (1993)
Ball, L. J., et al., *EMBO J.* 16:2473–2481 (1997)
Birney, E., et al., *Nucl. Acids Res.* 24:2730–2739 (1996)
Chen, D., et al., *Science* 284:2174–2177 (1999)
Cleard, F., et al., *EMBO J.* 16:5280–5288 (1997)
De Rubertis, F., et al., *Nature* 384:589–591 (1996)
Eddy, S. R., *Genetics* 131:345–352 (1998)
Ekwall, K., et al., *J. Cell. Sci.* 109:2637–2648 (1996)
Frishman, D., and Argos, P., *Proteins,* 27:329–335 (1997)
Grunstein, M., *Cell* 93:325–328 (1998)
Henikoff, S., "Position effect variegation in *Drosophila*: recent progress," in *Epigenetic mechanisms of gene regulation.* CSHL press (1997)
Ivanova, A. V., et al., *Nat. Genet.* 19:192–195 (1998)
Jacobson, S., and Pillus, L., *Curr. Opin. Genet. Dev.* 9:175–184 (1999)
Jenuwein, T., et al., *Cell. Mol. Life Sci.* 54:80–93 (1998)
Karpen, G. H., and Allshire, R. C., *TIG* 13:489–496 (1997)
Klein, R. R., and Houtz, R. L., *Plant Mol. Biol.* 27:249–261 (1995)
Koonin, E. V., et al., *Nucl. Acids Res.* 23:4229–4233 (1995)
Laible, G., et al., *EMBO J.* 16:3219–3232 (1997)
Larsson, J., et al., *Genetics* 143:887–896 (1996)
Martzen, M. R., et al., *Science* 286:1153–1155 (1999)
Melcher, M., et al., *Mol. Cell Biol.* 20:3728–3741 (2000)
Pehrson, J. R., and Fried, V. A., *Science* 257:1398–1400 (1992)
Platero, J. S., et al., *EMBO J.* 14:3977–3986 (1995)
Reuter, G., and Spierer, P., *BioEssays* 14:605–612 (1992)
Sassone-Corsi, P., et al., *Science* 285:886–891 (1999)
Schotta, G., and Reuter, G., *Mol. Gen. Genet,* 262:916–920 (2000)
Schultz, J., et al., *Nucl. Acids Res.* 28:231–234 (2000)
Strahl, B. D., and Allis, C. D., *Nature* 403:41–45 (2000)
Strahl, B. D., et al., *Proc. Natl. Acad. Sci. USA* 96:14967–14972 (1999)
Sullivan, K. F., et al., *J. Cell Biol.* 127:581–592 (1994)
Tkachuk, D. C., et al., *Cell* 71:691–700 (1992)
Tschiersch, B., et al., *EMBO J.* 13:3822–3831 (1994)
Turner, B. M., *Cell. Mol. Life Sci.* 54:21–31 (1998)
Wallrath, L. L., *Curr. Opin. Genet. Dev.* 8:147–153 (1998)
Wei, Y., et al., *Cell* 97:99–109 (1999)
Zheng, Q., et al., *Protein Expr. Purif.* 14:104–112 (1998)

What is claimed is:

1. An isolated nucleic acid molecule comprising a polynucleotide selected from the group consisting of:
    (a) a polynucleotide encoding amino acids 1 to 746 of SEQ ID NO:2;
    (b) a polynucleotide enoding a protein containing amino acids of SEQ ID NO: 2, wherein a stop codon shortens the protein by 47 C-terminal amino acids; and with a polynucleotide encoding a protein containing amino acids 1–699 of SEQ ID NO:2; and
    (c) a polynucleotide complementary to the polynucleotide of (a) or (b).

2. The nucleic acid molecule of claim 1, wherein said polynucleotide is (a).

3. The nucleic acid molecule of claim 2, wherein said polynucleotide comprises nucleotides 90–2330 of SEQ ID NO:1.

4. The nucleic acid molecule of claim 1, wherein said polynucleotide is (b).

5. The nucleic acid molecule of claim 1, wherein said polynucleotide is (c).

6. A vector comprising the isolated nucleic acid molecule of claim 1.

7. A method of producing a vector comprising inserting the isolated nucleic acid molecule of claim 1 into a vector.

8. An isolated recombinant DNA molecule comprising:
    (a) the isolated DNA molecule of claim 1; and
    (b) expression control sequences.

9. A host cell comprising the isolated nucleic acid molecule of claim 1.

10. The host cell of claim 9 that is prokaryotic.

11. The host cell of claim 9 that is eukaryotic.

12. The host cell of claim 9 wherein said isolated nucleic acid molecule is operably associated with a heterologous regulatory sequence.

13. A method of producing a polypeptide comprising culturing the host cell of claim 9 under conditions such that said polypeptide is expressed, and recovering said polypeptide.

* * * * *

UNITED STATES PATENT AND TRADEMARK OFFICE
CERTIFICATE OF CORRECTION

PATENT NO. : 7,252,968 B2
APPLICATION NO. : 10/773302
DATED : August 7, 2007
INVENTOR(S) : Jenuwein et al.

It is certified that error appears in the above-identified patent and that said Letters Patent is hereby corrected as shown below:

In column 51, lines 6-8, please delete "a polynucleotide encoding a protein containing amino acids of SEQ ID NO: 2, wherein a stop codon shortens the protein by 47 C-terminal amino acids; and with".

Signed and Sealed this

Sixth Day of November, 2007

JON W. DUDAS
*Director of the United States Patent and Trademark Office*

SEQUENCE LISTING

```
<160> NUMBER OF SEQ ID NOS: 21

<210> SEQ ID NO 1
<211> LENGTH: 2600
<212> TYPE: DNA
<213> ORGANISM: Homo sapiens
<220> FEATURE:
<221> NAME/KEY: 5'UTR
<222> LOCATION: (1)..(89)
<220> FEATURE:
<221> NAME/KEY: CDS
<222> LOCATION: (90)..(2330)
<220> FEATURE:
<221> NAME/KEY: 3'UTR
<222> LOCATION: (2331)..(2600)

<400> SEQUENCE: 1
aggcagtgga gccccggcgg cggcggcggc ggcgcgcggg ggcgacgcgc gggaacaacg      60
cgagtcggcg cgcgggacga agaataatc atg ggc cag act ggg aag aaa tct     113
                                Met Gly Gln Thr Gly Lys Lys Ser
                                  1               5
```

-continued

```
gag aag gga cca gtt tgt tgg cgg aag cgt gta aaa tca gag tac atg    161
Glu Lys Gly Pro Val Cys Trp Arg Lys Arg Val Lys Ser Glu Tyr Met
     10              15                  20 cga ctg aga cag ctc aag agg ttc aga cga gct gat gaa gta aag agt    209
Arg Leu Arg Gln Leu Lys Arg Phe Arg Arg Ala Asp Glu Val Lys Ser
 25              30                  35                  40 atg ttt agt tcc aat cgt cag aaa att ttg gaa aga acg gaa atc tta    257
Met Phe Ser Ser Asn Arg Gln Lys Ile Leu Glu Arg Thr Glu Ile Leu
                 45                  50                  55 aac caa gaa tgg aaa cag cga agg ata cag cct gtg cac atc ctg act    305
Asn Gln Glu Trp Lys Gln Arg Arg Ile Gln Pro Val His Ile Leu Thr
             60                  65                  70 tct gtg agc tca ttg cgc ggg act agg gag tgt tcg gtg acc agt gac    353
Ser Val Ser Ser Leu Arg Gly Thr Arg Glu Cys Ser Val Thr Ser Asp
         75                  80                  85 ttg gat ttt cca aca caa gtc atc cca tta aag act ctg aat gca gtt    401
Leu Asp Phe Pro Thr Gln Val Ile Pro Leu Lys Thr Leu Asn Ala Val
     90                  95                 100 gct tca gta ccc ata atg tat tct tgg tct ccc cta cag cag aat ttt    449
Ala Ser Val Pro Ile Met Tyr Ser Trp Ser Pro Leu Gln Gln Asn Phe
105                 110                 115                 120 atg gtg gaa gat gaa act gtt tta cat aac att cct tat atg gga gat    497
Met Val Glu Asp Glu Thr Val Leu His Asn Ile Pro Tyr Met Gly Asp
                125                 130                 135 gaa gtt tta gat cag gat ggt act ttc att gaa gaa cta ata aaa aat    545
Glu Val Leu Asp Gln Asp Gly Thr Phe Ile Glu Glu Leu Ile Lys Asn
            140                 145                 150 tat gat ggg aaa gta cac ggg gat aga gaa tgt ggg ttt ata aat gat    593
Tyr Asp Gly Lys Val His Gly Asp Arg Glu Cys Gly Phe Ile Asn Asp
        155                 160                 165 gaa att ttt gtg gag ttg gtg aat gcc ctt ggt caa tat aat gat gat    641
Glu Ile Phe Val Glu Leu Val Asn Ala Leu Gly Gln Tyr Asn Asp Asp
    170                 175                 180 gac gat gat gat gat gga gac gat cct gaa gaa aga gaa gaa aag cag    689
Asp Asp Asp Asp Asp Gly Asp Asp Pro Glu Glu Arg Glu Glu Lys Gln
185                 190                 195                 200 aaa gat ctg gag gat cac cga gat gat aaa gaa agc cgc cca cct cgg    737
Lys Asp Leu Glu Asp His Arg Asp Asp Lys Glu Ser Arg Pro Pro Arg
                205                 210                 215 aaa ttt cct tct gat aaa att ttt gaa gcc att tcc tca atg ttt cca    785
Lys Phe Pro Ser Asp Lys Ile Phe Glu Ala Ile Ser Ser Met Phe Pro
            220                 225                 230 gat aag ggc aca gca gaa gaa cta aag gaa aaa tat aaa gaa ctc acc    833
Asp Lys Gly Thr Ala Glu Glu Leu Lys Glu Lys Tyr Lys Glu Leu Thr
        235                 240                 245 gaa cag cag ctc cca ggc gca ctt cct cct gaa tgt acc ccc aac ata    881
Glu Gln Gln Leu Pro Gly Ala Leu Pro Pro Glu Cys Thr Pro Asn Ile
    250                 255                 260 gat gga cca aat gct aaa tct gtt cag aga gag caa agc tta cac tcc    929
Asp Gly Pro Asn Ala Lys Ser Val Gln Arg Glu Gln Ser Leu His Ser
265                 270                 275                 280 ttt cat acg ctt ttc tgt agg cga tgt ttt aaa tat gac tgc ttc cta    977
Phe His Thr Leu Phe Cys Arg Arg Cys Phe Lys Tyr Asp Cys Phe Leu
                285                 290                 295 cat cct ttt cat gca aca ccc aac act tat aag cgg aag aac aca gaa   1025
His Pro Phe His Ala Thr Pro Asn Thr Tyr Lys Arg Lys Asn Thr Glu
            300                 305                 310 aca gct cta gac aac aaa cct tgt gga cca cag tgt tac cag cat ttg   1073
Thr Ala Leu Asp Asn Lys Pro Cys Gly Pro Gln Cys Tyr Gln His Leu
        315                 320                 325
```

| | | |
|---|---|---|
| gag gga gca aag gag ttt gct gct gct ctc acc gct gag cgg ata aag<br>Glu Gly Ala Lys Glu Phe Ala Ala Ala Leu Thr Ala Glu Arg Ile Lys<br>330 335 340 | | 1121 |
| acc cca cca aaa cgt cca gga ggc cgc aga aga gga cgg ctt ccc aat<br>Thr Pro Pro Lys Arg Pro Gly Gly Arg Arg Arg Gly Arg Leu Pro Asn<br>345 350 355 360 | | 1169 |
| aac agt agc agg ccc agc acc ccc acc att aat gtg ctg gaa tca aag<br>Asn Ser Ser Arg Pro Ser Thr Pro Thr Ile Asn Val Leu Glu Ser Lys<br>365 370 375 | | 1217 |
| gat aca gac agt gat agg gaa gca ggg act gaa acg ggg gga gag aac<br>Asp Thr Asp Ser Asp Arg Glu Ala Gly Thr Glu Thr Gly Gly Glu Asn<br>380 385 390 | | 1265 |
| aat gat aaa gaa gaa gaa gag aag aaa gat gaa act tcg agc tcc tct<br>Asn Asp Lys Glu Glu Glu Lys Lys Asp Glu Thr Ser Ser Ser Ser<br>395 400 405 | | 1313 |
| gaa gca aat tct cgg tgt caa aca cca ata aag atg aag cca aat att<br>Glu Ala Asn Ser Arg Cys Gln Thr Pro Ile Lys Met Lys Pro Asn Ile<br>410 415 420 | | 1361 |
| gaa cct cct gag aat gtg gag tgg agt ggt gct gaa gcc tca atg ttt<br>Glu Pro Pro Glu Asn Val Glu Trp Ser Gly Ala Glu Ala Ser Met Phe<br>425 430 435 440 | | 1409 |
| aga gtc ctc att ggc act tac tat gac aat ttc tgt gcc att gct agg<br>Arg Val Leu Ile Gly Thr Tyr Tyr Asp Asn Phe Cys Ala Ile Ala Arg<br>445 450 455 | | 1457 |
| tta att ggg acc aaa aca tgt aga cag gtg tat gag ttt aga gtc aaa<br>Leu Ile Gly Thr Lys Thr Cys Arg Gln Val Tyr Glu Phe Arg Val Lys<br>460 465 470 | | 1505 |
| gaa tct agc atc ata gct cca gct ccc gct gag gat gtg gat act cct<br>Glu Ser Ser Ile Ile Ala Pro Ala Pro Ala Glu Asp Val Asp Thr Pro<br>475 480 485 | | 1553 |
| cca agg aaa aag aag agg aaa cac cgg ttg tgg gct gca cac tgc aga<br>Pro Arg Lys Lys Lys Arg Lys His Arg Leu Trp Ala Ala His Cys Arg<br>490 495 500 | | 1601 |
| aag ata cag ctg aaa aag gac ggc tcc tct aac cat gtt tac aac tat<br>Lys Ile Gln Leu Lys Lys Asp Gly Ser Ser Asn His Val Tyr Asn Tyr<br>505 510 515 520 | | 1649 |
| caa ccc tgt gat cat cca cgg cag cct tgt gac agt tcg tgc cct tgt<br>Gln Pro Cys Asp His Pro Arg Gln Pro Cys Asp Ser Ser Cys Pro Cys<br>525 530 535 | | 1697 |
| gtg ata gca caa aat ttt tgt gaa aag ttt tgt caa tgt agt tca gag<br>Val Ile Ala Gln Asn Phe Cys Glu Lys Phe Cys Gln Cys Ser Ser Glu<br>540 545 550 | | 1745 |
| tgt caa aac cgc ttt ccg gga tgc cgc tgc aaa gca cag tgc aac acc<br>Cys Gln Asn Arg Phe Pro Gly Cys Arg Cys Lys Ala Gln Cys Asn Thr<br>555 560 565 | | 1793 |
| aag cag tgc ccg tgc tac ctg gct gtc cga gag tgt gac cct gac ctc<br>Lys Gln Cys Pro Cys Tyr Leu Ala Val Arg Glu Cys Asp Pro Asp Leu<br>570 575 580 | | 1841 |
| tgt ctt act tgt gga gcc gct gac cat tgg gac agt aaa aat gtg tcc<br>Cys Leu Thr Cys Gly Ala Ala Asp His Trp Asp Ser Lys Asn Val Ser<br>585 590 595 600 | | 1889 |
| tgc aag aac tgc agt att cag cgg ggc tcc aaa aag cat cta ttg ctg<br>Cys Lys Asn Cys Ser Ile Gln Arg Gly Ser Lys Lys His Leu Leu Leu<br>605 610 615 | | 1937 |
| gca cca tct gac gtg gca ggc tgg ggg att ttt atc aaa gat cct gtg<br>Ala Pro Ser Asp Val Ala Gly Trp Gly Ile Phe Ile Lys Asp Pro Val<br>620 625 630 | | 1985 |
| cag aaa aat gaa ttc atc tca gaa tac tgt gga gag att att tct caa<br>Gln Lys Asn Glu Phe Ile Ser Glu Tyr Cys Gly Glu Ile Ile Ser Gln | | 2033 |

```
                         635                 640                 645
gat gaa gct gac aga aga ggg aaa gtg tat gat aaa tac atg tgc agc                2081
Asp Glu Ala Asp Arg Arg Gly Lys Val Tyr Asp Lys Tyr Met Cys Ser
        650                 655                 660 ttt ctg ttc aac ttg aac aat gat ttt gtg gtg gat gca acc cgc aag                2129
Phe Leu Phe Asn Leu Asn Asn Asp Phe Val Val Asp Ala Thr Arg Lys
665                 670                 675                 680 ggt aac aaa att cgt ttt gca aat cat tcg gta aat cca aac tgc tat                2177
Gly Asn Lys Ile Arg Phe Ala Asn His Ser Val Asn Pro Asn Cys Tyr
                685                 690                 695 gca aaa gtt atg atg gtt aac ggt gat cac agg ata ggt att ttt gcc                2225
Ala Lys Val Met Met Val Asn Gly Asp His Arg Ile Gly Ile Phe Ala
            700                 705                 710 aag aga gcc atc cag act ggc gaa gag ctg ttt ttt gat tac aga tac                2273
Lys Arg Ala Ile Gln Thr Gly Glu Glu Leu Phe Phe Asp Tyr Arg Tyr
                715                 720                 725 agc cag gct gat gcc ctg aag tat gtc ggc atc gaa aga gaa atg gaa                2321
Ser Gln Ala Asp Ala Leu Lys Tyr Val Gly Ile Glu Arg Glu Met Glu
            730                 735                 740 atc cct tga catctgctac ctcctccccc tcctctgaaa cagctgcctt                        2370
Ile Pro
745 agcttcagga acctcgagta ctgtgggcaa tttagaaaaa gaacatgcag tttgaaattc              2430 tgaatttgca aagtactgta agaataattt atagtaatga gtttaaaaat caactttta              2490 ttgccttctc accagctgca aagtgttttg taccagtgaa ttttttgcaat aatgcagtat             2550 ggtacatttt tcaactttga ataaagaata cttgaacttg tcaaaaaaaa                         2600
```

<210> SEQ ID NO 2
<211> LENGTH: 746
<212> TYPE: PRT
<213> ORGANISM: Homo sapiens

<400> SEQUENCE: 2

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175
```

```
-continued

Ala Leu Gly Gln Tyr Asn Asp Asp Asp Asp Asp Gly Asp Asp
            180                 185                 190

Pro Glu Glu Arg Glu Lys Gln Lys Asp Leu Glu Asp His Arg Asp
            195                 200                 205

Asp Lys Glu Ser Arg Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
            275                 280                 285

Cys Phe Lys Tyr Asp Cys Phe Leu His Pro Phe His Ala Thr Pro Asn
    290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
            355                 360                 365

Thr Ile Asn Val Leu Glu Ser Lys Asp Thr Asp Ser Asp Arg Glu Ala
    370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
            420                 425                 430

Ser Gly Ala Glu Ala Ser Met Phe Arg Val Leu Ile Gly Thr Tyr Tyr
            435                 440                 445

Asp Asn Phe Cys Ala Ile Ala Arg Leu Ile Gly Thr Lys Thr Cys Arg
    450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Arg Lys His
                485                 490                 495

Arg Leu Trp Ala Ala His Cys Arg Lys Ile Gln Leu Lys Lys Asp Gly
            500                 505                 510

Ser Ser Asn His Val Tyr Asn Tyr Gln Pro Cys Asp His Pro Arg Gln
            515                 520                 525

Pro Cys Asp Ser Ser Cys Pro Cys Val Ile Ala Gln Asn Phe Cys Glu
    530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
            580                 585                 590

His Trp Asp Ser Lys Asn Val Ser Cys Lys Asn Cys Ser Ile Gln Arg
```

```
              595                 600                 605
Gly Ser Lys Lys His Leu Leu Leu Ala Pro Ser Asp Val Ala Gly Trp
    610                 615                 620

Gly Ile Phe Ile Lys Asp Pro Val Gln Lys Asn Glu Phe Ile Ser Glu
625                 630                 635                 640

Tyr Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
                660                 665                 670

Phe Val Val Asp Ala Thr Arg Lys Gly Asn Lys Ile Arg Phe Ala Asn
                675                 680                 685

His Ser Val Asn Pro Asn Cys Tyr Ala Lys Val Met Met Val Asn Gly
    690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745

<210> SEQ ID NO 3
<211> LENGTH: 2732
<212> TYPE: DNA
<213> ORGANISM: Homo sapiens
<220> FEATURE:
<221> NAME/KEY: 5'UTR
<222> LOCATION: (1)..(44)
<220> FEATURE:
<221> NAME/KEY: CDS
<222> LOCATION: (45)..(1283)
<220> FEATURE:
<221> NAME/KEY: 3'UTR
<222> LOCATION: (1284)..(2732)

<400> SEQUENCE: 3
tcgcgaggcc ggctaggccc gaatgtcgtt agccgtgggg aaag atg gcg gaa aat        56
                                                Met Ala Glu Asn
                                                  1 tta aaa ggc tgc agc gtg tgt tgc aag tct tct tgg aat cag ctg cag       104
Leu Lys Gly Cys Ser Val Cys Cys Lys Ser Ser Trp Asn Gln Leu Gln
 5                  10                  15                  20 gac ctg tgc cgc ctg gcc aag ctc tcc tgc cct gcc ctc ggt atc tct       152
Asp Leu Cys Arg Leu Ala Lys Leu Ser Cys Pro Ala Leu Gly Ile Ser
                25                  30                  35 aag agg aac ctc tat gac ttt gaa gtc gag tac ctg tgc gat tac aag       200
Lys Arg Asn Leu Tyr Asp Phe Glu Val Glu Tyr Leu Cys Asp Tyr Lys
            40                  45                  50 aag atc cgc gaa cag gaa tat tac ctg gtg aaa tgg cgt gga tat cca       248
Lys Ile Arg Glu Gln Glu Tyr Tyr Leu Val Lys Trp Arg Gly Tyr Pro
        55                  60                  65 gac tca gag agc acc tgg gag cca cgg cag aat ctc aag tgt gtg cgt       296
Asp Ser Glu Ser Thr Trp Glu Pro Arg Gln Asn Leu Lys Cys Val Arg
    70                  75                  80 atc ctc aag cag ttc cac aag gac tta gaa agg gag ctg ctc cgg cgg       344
Ile Leu Lys Gln Phe His Lys Asp Leu Glu Arg Glu Leu Leu Arg Arg
85                  90                  95                 100 cac cac cgg tca aag acc ccc cgg cac ctg gac cca agc ttg gcc aac       392
His His Arg Ser Lys Thr Pro Arg His Leu Asp Pro Ser Leu Ala Asn
                105                 110                 115 tac ctg gtg cag aag gcc aag cag agg cgg gcg ctc cgt gcc tgg gag       440
```

```
Tyr Leu Val Gln Lys Ala Lys Gln Arg Arg Ala Leu Arg Arg Trp Glu
            120                 125                 130 cag gag ctc aat gcc aag cgc agc cat ctg gga cgc atc act gta gag    488
Gln Glu Leu Asn Ala Lys Arg Ser His Leu Gly Arg Ile Thr Val Glu
            135                 140                 145 aat gag gtg gac ctg gac ggc cct ccg cgg gcc ttc gtg tac atc aat    536
Asn Glu Val Asp Leu Asp Gly Pro Pro Arg Ala Phe Val Tyr Ile Asn
    150                 155                 160 gag tac cgt gtt ggt gag ggc atc acc ctc aac cag gtg gct gtg ggc    584
Glu Tyr Arg Val Gly Glu Gly Ile Thr Leu Asn Gln Val Ala Val Gly
165                 170                 175                 180 tgc gag tgc cag gac tgt ctg tgg gca ccc act gga ggc tgc tgc ccg    632
Cys Glu Cys Gln Asp Cys Leu Trp Ala Pro Thr Gly Gly Cys Cys Pro
                185                 190                 195 ggg gcg tca ctg cac aag ttt gcc tac aat gac cag ggc cag gtg cgg    680
Gly Ala Ser Leu His Lys Phe Ala Tyr Asn Asp Gln Gly Gln Val Arg
            200                 205                 210 ctt cga gcc ggg ctg ccc atc tac gag tgc aac tcc cgc tgc cgc tgc    728
Leu Arg Ala Gly Leu Pro Ile Tyr Glu Cys Asn Ser Arg Cys Arg Cys
            215                 220                 225 ggc tat gac tgc cca aat cgt gtg gta cag aag ggt atc cga tat gac    776
Gly Tyr Asp Cys Pro Asn Arg Val Val Gln Lys Gly Ile Arg Tyr Asp
        230                 235                 240 ctc tgc atc ttc cgg acg gat gat ggg cgt ggc tgg ggc gtc cgc acc    824
Leu Cys Ile Phe Arg Thr Asp Asp Gly Arg Gly Trp Gly Val Arg Thr
245                 250                 255                 260 ctg gag aag att cgc aag aac agc ttc gtc atg gag tac gtg gga gag    872
Leu Glu Lys Ile Arg Lys Asn Ser Phe Val Met Glu Tyr Val Gly Glu
                265                 270                 275 atc att acc tca gag gag gca gag cgg cgg ggc cag atc tac gac cgt    920
Ile Ile Thr Ser Glu Glu Ala Glu Arg Arg Gly Gln Ile Tyr Asp Arg
            280                 285                 290 cag ggc gcc acc tac ctc ttt gac ctg gac tac gtg gag gac gtg tac    968
Gln Gly Ala Thr Tyr Leu Phe Asp Leu Asp Tyr Val Glu Asp Val Tyr
            295                 300                 305 acc gtg gat gcc gcc tac tat ggc aac atc tcc cac ttt gtc aac cac   1016
Thr Val Asp Ala Ala Tyr Tyr Gly Asn Ile Ser His Phe Val Asn His
        310                 315                 320 agt tgt gac ccc aac ctg cag gtg tac aac gtc ttc ata gac aac ctt   1064
Ser Cys Asp Pro Asn Leu Gln Val Tyr Asn Val Phe Ile Asp Asn Leu
325                 330                 335                 340 gac gag cgg ctg ccc cgc atc gct ttc ttt gcc aca aga acc atc cgg   1112
Asp Glu Arg Leu Pro Arg Ile Ala Phe Phe Ala Thr Arg Thr Ile Arg
                345                 350                 355 gca ggc gag gag ctc acc ttt gat tac aac atg caa gtg gac ccc gtg   1160
Ala Gly Glu Glu Leu Thr Phe Asp Tyr Asn Met Gln Val Asp Pro Val
            360                 365                 370 gac atg gag agc acc cgc atg gac tcc aac ttt ggc ctg gct ggg ctc   1208
Asp Met Glu Ser Thr Arg Met Asp Ser Asn Phe Gly Leu Ala Gly Leu
            375                 380                 385 cct ggc tcc cct aag aag cgg gtc cgt att gaa tgc aag tgt ggg act   1256
Pro Gly Ser Pro Lys Lys Arg Val Arg Ile Glu Cys Lys Cys Gly Thr
        390                 395                 400 gag tcc tgc cgc aaa tac ctc ttc tag cccttagaag tctgaggcca          1303
Glu Ser Cys Arg Lys Tyr Leu Phe
405                 410 gactgactga gggggcctga agctacatgc acctccccca ctgctgccct cctgtcgaga  1363
atgactgcca gggcctcgcc tgcctccacc tgccccacc tgctcctacc tgctctacgt   1423
```

-continued

```
tcagggctgt ggccgtggtg aggaccgact ccaggagtcc cctttccctg tcccagcccc   1483
atctgtgggt tgcacttaca aaccccacc caccttcaga aatagttttt caacatcaag   1543
actctctgtc gttgggattc atggcctatt aaggaggtcc aagggtgag tcccaaccca   1603
gccccagaat atatttgttt ttgcacctgc ttctgcctgg agattgaggg gtctgctgca   1663
ggcctcctcc ctgctgcccc aaaggtatgg ggaagcaacc ccagagcagg cagacatcag   1723
aggccagagt gcctagcccg acatgaagct ggttccccaa ccacagaaac tttgtactag   1783
tgaaagaaag gggtccctgg cctacgggct gaggctggtt tctgctcgtg cttacagtgc   1843
tgggtagtgt tggccctaag agctgtaggg tctcttcttc agggctgcat atctgagaag   1903
tggatgccca catgccactg gaagggaagt gggtgtccat gggccactga gcagtgagag   1963
gaaggcagtg cagagctggc cagccctgga ggtaggctgg gaccaagctc tgccttcaca   2023
gtgcagtgaa ggtacctagg gctcttggga gctctgcggt tgctaggggc cctgacctgg   2083
ggtgtcatga ccgctgacac cactcagagc tggaaccaag atctagatag tccgtagata   2143
gcacttagga caagaatgtg cattgatggg gtggtgatga ggtgccaggc actaggtaga   2203
gcacctggtc cacgtggatt gtctcaggga agccttgaaa accacggagg tggatgccag   2263
gaaagggccc atgtggcaga aggcaaagta caggccaaga attgggggtg ggggagatgg   2323
cttcccccact atgggatgac gaggcgagag ggaagcccctt gctgcctgcc attcccagac   2383
cccagcccctt tgtgctcacc ctggttccac tggtctcaaa agtcacctgc ctacaaatgt   2443
acaaaaggcg aaggttctga tggctgcctt gctccttgct ccccaccccc ctgtgaggac   2503
ttctctagga agtccttcct gactacctgt gcccagagtg cccctacatg agactgtatg   2563
ccctgctatc agatgccaga tctatgtgtc tgtctgtgtg tccatcccgc cggcccccca   2623
gactaacctc caggcatgga ctgaatctgg ttctcctctt gtacaccctc aacctatg    2683
cagcctggag tgggcatcaa taaaatgaac tgtcgactga aaaaaaaa               2732
```

<210> SEQ ID NO 4
<211> LENGTH: 412
<212> TYPE: PRT
<213> ORGANISM: Homo sapiens

<400> SEQUENCE: 4

```
Met Ala Glu Asn Leu Lys Gly Cys Ser Val Cys Cys Lys Ser Ser Trp
1               5                   10                  15

Asn Gln Leu Gln Asp Leu Cys Arg Leu Ala Lys Leu Ser Cys Pro Ala
            20                  25                  30

Leu Gly Ile Ser Lys Arg Asn Leu Tyr Asp Phe Glu Val Glu Tyr Leu
        35                  40                  45

Cys Asp Tyr Lys Lys Ile Arg Glu Gln Glu Tyr Tyr Leu Val Lys Trp
    50                  55                  60

Arg Gly Tyr Pro Asp Ser Glu Ser Thr Trp Glu Pro Arg Gln Asn Leu
65                  70                  75                  80

Lys Cys Val Arg Ile Leu Lys Gln Phe His Lys Asp Leu Glu Arg Glu
                85                  90                  95

Leu Leu Arg Arg His His Arg Ser Lys Thr Pro Arg His Leu Asp Pro
            100                 105                 110

Ser Leu Ala Asn Tyr Leu Val Gln Lys Ala Lys Gln Arg Arg Ala Leu
        115                 120                 125

Arg Arg Trp Glu Gln Glu Leu Asn Ala Lys Arg Ser His Leu Gly Arg
    130                 135                 140
```

| | | | | | | | | | | | |
|---|---|---|---|---|---|---|---|---|---|---|---|
|Ile|Thr|Val|Glu|Asn|Glu|Val|Asp|Leu|Asp|Gly|Pro Pro Arg Ala Phe|
|145| | | |150| | | |155| | |160|

Val Tyr Ile Asn Glu Tyr Arg Val Gly Glu Gly Ile Thr Leu Asn Gln
                165                 170                 175

Val Ala Val Gly Cys Glu Cys Gln Asp Cys Leu Trp Ala Pro Thr Gly
            180                 185                 190

Gly Cys Cys Pro Gly Ala Ser Leu His Lys Phe Ala Tyr Asn Asp Gln
        195                 200                 205

Gly Gln Val Arg Leu Arg Ala Gly Leu Pro Ile Tyr Glu Cys Asn Ser
    210                 215                 220

Arg Cys Arg Cys Gly Tyr Asp Cys Pro Asn Arg Val Val Gln Lys Gly
225                 230                 235                 240

Ile Arg Tyr Asp Leu Cys Ile Phe Arg Thr Asp Asp Gly Arg Gly Trp
                245                 250                 255

Gly Val Arg Thr Leu Glu Lys Ile Arg Lys Asn Ser Phe Val Met Glu
            260                 265                 270

Tyr Val Gly Glu Ile Ile Thr Ser Glu Glu Ala Glu Arg Arg Gly Gln
        275                 280                 285

Ile Tyr Asp Arg Gln Gly Ala Thr Tyr Leu Phe Asp Leu Asp Tyr Val
    290                 295                 300

Glu Asp Val Tyr Thr Val Asp Ala Ala Tyr Tyr Gly Asn Ile Ser His
305                 310                 315                 320

Phe Val Asn His Ser Cys Asp Pro Asn Leu Gln Val Tyr Asn Val Phe
                325                 330                 335

Ile Asp Asn Leu Asp Glu Arg Leu Pro Arg Ile Ala Phe Phe Ala Thr
            340                 345                 350

Arg Thr Ile Arg Ala Gly Glu Glu Leu Thr Phe Asp Tyr Asn Met Gln
        355                 360                 365

Val Asp Pro Val Asp Met Glu Ser Thr Arg Met Asp Ser Asn Phe Gly
    370                 375                 380

Leu Ala Gly Leu Pro Gly Ser Pro Lys Lys Arg Val Arg Ile Glu Cys
385                 390                 395                 400

Lys Cys Gly Thr Glu Ser Cys Arg Lys Tyr Leu Phe
                405                 410

<210> SEQ ID NO 5
<211> LENGTH: 489
<212> TYPE: DNA
<213> ORGANISM: Homo sapiens

<400> SEQUENCE: 5

```
actcaccltgt ggggcctcag agcactggga ctgcaaggtg gtttcctgta aaaactgcag     60
catccagcgt ggacttaaga agcacctgct gctggccccc tctgatgtgg ccggatgggg    120
caccttcata aaggagtctg tgcagaagaa cgaattcatt tctgaatact gtggtgagct    180
catctctcag gatgaggctg atcgacgcgg aaaggtctat gacaaataca tgtccagctt    240
cctcttcaac ctcaataatg attttgtagt ggatgctact cggaaaggaa acaaaattcg    300
atttgcaaat cattcagtga atcccaactg ttatgccaaa ggtgagtccc agtaacctgg    360
gaggtggggt gggggatgga tgcctctta ctgtgatttc cattcgttgt tgaacatttt    420
ccttagctga gctatctttt gtccaaagat aatcatgatt aatatctggt atcattttag    480
gccctctc                                                             489
```

<210> SEQ ID NO 6

```
<211> LENGTH: 20
<212> TYPE: DNA
<213> ORGANISM: Artificial Sequence
<220> FEATURE:
<223> OTHER INFORMATION: EcoRI Adaptor oligonucleotide

<400> SEQUENCE: 6
aattctcgag ctcgtcgaca                                                    20

<210> SEQ ID NO 7
<211> LENGTH: 31
<212> TYPE: DNA
<213> ORGANISM: Drosophila melanogaster

<400> SEQUENCE: 7
actgaattcg gctggggcat ctttcttaag g                                       31

<210> SEQ ID NO 8
<211> LENGTH: 31
<212> TYPE: DNA
<213> ORGANISM: Drosophila melanogaster

<400> SEQUENCE: 8
actctagaca atttccattt cacgctctat g                                       31

<210> SEQ ID NO 9
<211> LENGTH: 30
<212> TYPE: DNA
<213> ORGANISM: Drosophila melanogaster.

<400> SEQUENCE: 9
atatagtact tcaagtccat tcaaaagagg                                         30

<210> SEQ ID NO 10
<211> LENGTH: 29
<212> TYPE: DNA
<213> ORGANISM: Drosophila melanogaster

<400> SEQUENCE: 10
ccaggtaccg ttggtgctgt ttaagaccg                                          29

<210> SEQ ID NO 11
<211> LENGTH: 760
<212> TYPE: PRT
<213> ORGANISM: Drosophila melanogaster

<400> SEQUENCE: 11
```

Met Asn Ser Thr Lys Val Pro Pro Glu Trp Lys Arg Arg Val Lys Ser
1               5                   10                  15

Glu Tyr Ile Lys Ile Arg Gln Gln Lys Arg Tyr Lys Arg Ala Asp Glu
                20                  25                  30

Ile Lys Glu Ala Trp Ile Arg Asn Trp Asp Glu His Asn His Asn Val
            35                  40                  45

Gln Asp Leu Tyr Cys Glu Ser Lys Val Trp Gln Ala Lys Pro Tyr Asp
        50                  55                  60

Pro Pro His Val Asp Cys Val Lys Arg Ala Glu Val Thr Ser Tyr Asn
65                  70                  75                  80

Gly Ile Pro Ser Gly Pro Gln Lys Val Pro Ile Cys Asx Ile Asn Ala
                85                  90                  95

Val Thr Pro Ile Pro Thr Met Tyr Thr Trp Ala Pro Thr Gln Gln Asn
            100                 105                 110

-continued

```
Phe Met Val Glu Asp Glu Thr Val Leu His Asn Ile Pro Tyr Met Gly
            115                 120                 125

Asp Glu Val Leu Asp Lys Asp Gly Lys Phe Ile Glu Glu Leu Ile Lys
            130                 135                 140

Asn Tyr Asp Gly Lys Val His Gly Asp Lys Asp Pro Ser Phe Met Asp
145                 150                 155                 160

Asp Ala Ile Phe Val Glu Leu Val His Ala Leu Met Arg Ser Tyr Ser
                165                 170                 175

Lys Glu Leu Glu Glu Ala Ala Pro Ser Thr Ser Thr Ala Ile Lys Thr
            180                 185                 190

Glu Pro Leu Ala Lys Ser Lys Gln Gly Glu Asp Asp Gly Val Val Asp
            195                 200                 205

Val Asp Ala Asp Cys Glu Ser Pro Met Lys Leu Glu Lys Thr Glu Ser
            210                 215                 220

Lys Gly Asp Leu Thr Asp Val Glu Lys Lys Glu Thr Glu Pro Val
225                 230                 235                 240

Glu Thr Glu Asp Ala Asp Val Lys Pro Ala Val Glu Glu Val Lys Asp
                245                 250                 255

Lys Leu Pro Phe Pro Ala Pro Ile Ile Phe Gln Ala Ile Ser Ala Asn
            260                 265                 270

Phe Pro Asp Lys Gly Thr Ala Gln Glu Leu Lys Glu Lys Tyr Ile Glu
            275                 280                 285

Leu Thr Glu His Gln Asp Pro Glu Arg Pro Gln Glu Cys Thr Pro Asn
            290                 295                 300

Ile Asp Gly Ile Lys Ala Glu Ser Val Ser Arg Glu Arg Thr Met His
305                 310                 315                 320

Ser Phe His Thr Leu Pro Cys Arg Arg Cys Phe Lys Tyr Asp Cys Phe
                325                 330                 335

Leu His Arg Leu Gln Gly His Ala Gly Pro Asn Leu Gln Lys Arg Arg
            340                 345                 350

Tyr Pro Glu Leu Lys Pro Phe Ala Glu Pro Cys Ser Asn Ser Cys Tyr
            355                 360                 365

Met Leu Ile Asp Gly Met Lys Glu Lys Leu Ala Ala Asp Ser Lys Thr
            370                 375                 380

Pro Pro Ile Asp Ser Cys Asn Glu Ala Ser Ser Glu Asp Ser Asn Asp
385                 390                 395                 400

Ser Asn Ser Gln Phe Ser Asn Lys Asp Phe Asn His Glu Asn Ser Lys
                405                 410                 415

Asp Asn Gly Leu Thr Val Asn Ser Ala Ala Val Ala Glu Ile Asn Ser
            420                 425                 430

Ile Met Ala Gly Met Met Asn Ile Thr Ser Thr Gln Cys Val Trp Thr
            435                 440                 445

Gly Ala Asp Gln Ala Leu Tyr Arg Val Leu His Lys Val Tyr Leu Lys
450                 455                 460

Asn Tyr Cys Ala Ile Ala His Asn Met Leu Thr Lys Thr Cys Arg Gln
465                 470                 475                 480

Val Tyr Glu Phe Ala Gln Lys Glu Asp Ala Glu Ser Phe Ser Glu Asp
                485                 490                 495

Leu Arg Gln Asp Phe Thr Pro Arg Lys Lys Lys Lys Gln Arg
            500                 505                 510

Leu Trp Ser Leu His Cys Arg Lys Ile Gln Leu Lys Lys Asp Ser Ser
            515                 520                 525

Ser Asn His Val Tyr Asn Tyr Thr Arg Cys Asp His Pro Gly His Pro
```

-continued

```
            530                 535                 540
Cys Asp Met Asn Cys Ser Cys Ile Gln Thr Gln Asn Phe Cys Glu Lys
545                 550                 555                 560

Phe Cys Asn Cys Ser Ser Asp Cys Gln Asn Arg Phe Pro Gly Cys Arg
                565                 570                 575

Cys Lys Ala Gln Cys Asn Thr Lys Gln Cys Pro Cys Tyr Leu Ala Val
            580                 585                 590

Arg Glu Cys Asp Pro Asp Leu Cys Gln Ala Cys Gly Ala Asp Gln Phe
        595                 600                 605

Lys Leu Thr Lys Ile Thr Cys Lys Asn Val Cys Val Gln Arg Gly Leu
    610                 615                 620

His Lys His Leu Leu Met Ala Pro Ser Asp Ile Ala Gly Trp Gly Ile
625                 630                 635                 640

Phe Leu Lys Glu Gly Ala Gln Lys Asn Glu Phe Ile Ser Glu Tyr Cys
                645                 650                 655

Gly Glu Ile Ile Ser Gln Asp Glu Ala Asp Arg Arg Gly Lys Val Tyr
            660                 665                 670

Asp Lys Tyr Met Cys Ser Phe Leu Phe Asn Leu Asn Asn Asp Phe Val
        675                 680                 685

Val Asp Ala Thr Arg Lys Gly Asn Lys Ile Arg Phe Ala Asn His Ser
    690                 695                 700

Ile Asn Pro Asn Cys Tyr Ala Lys Val Met Met Val Thr Gly Asp His
705                 710                 715                 720

Arg Ile Gly Ile Phe Ala Lys Arg Ala Ile Gln Pro Gly Glu Glu Leu
                725                 730                 735

Phe Phe Asp Tyr Arg Tyr Gly Pro Thr Glu Gln Leu Lys Phe Val Gly
            740                 745                 750

Ile Glu Arg Glu Met Glu Ile Val
        755                 760

<210> SEQ ID NO 12
<211> LENGTH: 134
<212> TYPE: PRT
<213> ORGANISM: Homo sapiens

<400> SEQUENCE: 12

Ser Pro Ile His Gly Arg Gly Leu Phe Cys Lys Arg Asn Ile Asp Ala
1               5                   10                  15

Gly Glu Met Val Ile Glu Tyr Ala Gly Asn Val Ile Arg Ser Ile Gln
                20                  25                  30

Thr Asp Lys Arg Glu Lys Tyr Tyr Asp Ser Lys Gly Ile Gly Cys Tyr
            35                  40                  45

Met Phe Arg Ile Asp Asp Ser Glu Val Val Asp Ala Thr Met His Gly
    50                  55                  60

Asn Arg Ala Arg Phe Ile Asn His Ser Cys Glu Pro Asn Cys Tyr Ser
65                  70                  75                  80

Arg Val Ile Asn Ile Asp Gly Gln Lys His Ile Val Ile Phe Ala Met
                85                  90                  95

Arg Lys Ile Tyr Arg Gly Glu Glu Leu Thr Tyr Asp Tyr Lys Phe Pro
            100                 105                 110

Ile Glu Asp Ala Ser Asn Lys Leu Pro Cys Asn Cys Gly Ala Lys Lys
        115                 120                 125

Cys Arg Lys Phe Leu Asn
    130
```

<210> SEQ ID NO 13
<211> LENGTH: 132
<212> TYPE: PRT
<213> ORGANISM: Drosophila melanogaster

<400> SEQUENCE: 13

Ser His Ile His Gly Arg Gly Leu Tyr Cys Thr Lys Asp Ile Glu Ala
1               5                   10                  15

Gly Glu Met Val Ile Glu Tyr Ala Gly Glu Leu Ile Arg Ser Thr Leu
            20                  25                  30

Thr Asp Lys Arg Glu Arg Tyr Tyr Asp Ser Arg Gly Ile Gly Cys Tyr
        35                  40                  45

Met Phe Lys Ile Asp Asp Asn Leu Val Val Asp Ala Thr Met Arg Gly
    50                  55                  60

Asn Ala Ala Arg Phe Ile Asn His Cys Cys Glu Pro Asn Cys Tyr Ser
65                  70                  75                  80

Lys Val Val Asp Ile Leu Gly His Lys His Ile Ile Phe Ala Val
                85                  90                  95

Arg Arg Ile Val Gln Gly Glu Glu Leu Thr Tyr Asp Tyr Lys Phe Pro
            100                 105                 110

Phe Glu Asp Glu Lys Ile Pro Cys Ser Cys Gly Ser Lys Arg Cys Arg
        115                 120                 125

Lys Tyr Leu Asn
    130

<210> SEQ ID NO 14
<211> LENGTH: 133
<212> TYPE: PRT
<213> ORGANISM: Caenorhabditis elegans

<400> SEQUENCE: 14

Ser Arg Ile His Gly Trp Gly Leu Tyr Ala Met Glu Ser Ile Ala Pro
1               5                   10                  15

Asp Glu Met Ile Val Glu Tyr Ile Gly Gln Thr Ile Arg Ser Leu Val
            20                  25                  30

Ala Glu Glu Arg Glu Lys Ala Tyr Glu Arg Arg Gly Ile Gly Ser Ser
        35                  40                  45

Tyr Leu Phe Arg Ile Asp Leu His His Val Ile Asp Ala Thr Lys Arg
    50                  55                  60

Gly Asn Phe Ala Arg Phe Ile Asn His Ser Cys Gln Pro Asn Cys Tyr
65                  70                  75                  80

Ala Lys Val Leu Thr Ile Glu Gly Glu Lys Arg Ile Val Ile Tyr Ser
            85                  90                  95

Arg Thr Ile Ile Lys Lys Gly Glu Glu Ile Thr Tyr Asp Tyr Lys Phe
            100                 105                 110

Pro Ile Glu Asp Asp Lys Ile Asp Cys Leu Cys Gly Ala Lys Thr Cys
        115                 120                 125

Arg Gly Tyr Leu Asn
    130

<210> SEQ ID NO 15
<211> LENGTH: 136
<212> TYPE: PRT
<213> ORGANISM: Saccharomyces cerevisiae

<400> SEQUENCE: 15

Ser Ala Ile His Asn Trp Gly Leu Tyr Ala Leu Asp Ser Ile Ala Ala

```
                1               5              10              15
Lys Glu Met Ile Ile Glu Tyr Val Gly Glu Arg Ile Arg Gln Pro Val
                    20              25              30

Ala Glu Met Arg Glu Lys Arg Tyr Leu Lys Asn Gly Ile Gly Ser Ser
                35              40              45

Tyr Leu Phe Arg Val Asp Glu Asn Thr Val Ile Asp Ala Thr Lys Lys
        50              55              60

Gly Gly Ile Ala Arg Phe Ile Asn His Cys Cys Asp Pro Asn Cys Thr
65              70              75              80

Ala Lys Ile Ile Lys Val Gly Arg Arg Arg Ile Val Ile Tyr Ala
                    85              90              95

Leu Arg Asp Ile Ala Ala Ser Glu Glu Leu Thr Tyr Asp Tyr Lys Phe
                    100             105             110

Glu Arg Glu Lys Asp Asp Glu Glu Arg Leu Pro Cys Leu Cys Gly Ala
                115             120             125

Pro Asn Cys Lys Gly Phe Leu Asn
        130             135

<210> SEQ ID NO 16
<211> LENGTH: 429
<212> TYPE: PRT
<213> ORGANISM: Drosophila melanogaster

<400> SEQUENCE: 16

Met Gly Val Ile Ala Lys Arg Pro Pro Lys Gly Glu Tyr Val Val Glu
1               5              10              15

Arg Ile Glu Cys Val Glu Asn Asp Gln Tyr Gln Pro Val Phe Phe Val
                    20              25              30

Lys Trp Leu Gly Tyr His Asp Ser Glu Asn Thr Trp Glu Ser Leu Ala
                35              40              45

Asn Val Ala Asp Cys Ala Glu Met Glu Lys Phe Val Glu Arg His Gln
        50              55              60

Gln Leu Tyr Glu Thr Tyr Ile Ala Lys Ile Thr Thr Glu Leu Glu Lys
65              70              75              80

Gln Leu Glu Ala Leu Pro Leu Met Glu Asn Ile Thr Val Ala Glu Val
                    85              90              95

Asp Ala Tyr Glu Pro Leu Asn Leu Gln Ile Asp Leu Ile Leu Leu Ala
                100             105             110

Gln Tyr Arg Ala Ala Gly Ser Arg Ser Gln Arg Glu Pro Gln Lys Ile
                115             120             125

Gly Glu Arg Ala Leu Lys Ser Met Gln Ile Lys Arg Ala Gln Phe Val
        130             135             140

Arg Arg Lys Gln Leu Ala Asp Leu Ala Leu Phe Glu Lys Arg Met Asn
145             150             155             160

His Val Glu Lys Pro Ser Pro Ile Arg Val Glu Asn Asn Ile Asp
                    165             170             175

Leu Asp Thr Ile Asp Ser Asn Phe Met Tyr Ile His Asp Asn Ile Ile
                    180             185             190

Gly Lys Asp Val Pro Lys Pro Glu Ala Gly Ile Val Gly Cys Lys Cys
            195             200             205

Thr Glu Asp Thr Glu Glu Cys Thr Ala Ser Thr Lys Cys Cys Ala Arg
        210             215             220

Phe Ala Gly Glu Leu Phe Ala Tyr Glu Arg Ser Thr Arg Arg Leu Arg
225             230             235             240
```

-continued

```
Leu Arg Pro Gly Ser Ala Ile Tyr Glu Cys Asn Ser Arg Cys Ser Cys
                245                 250                 255

Asp Ser Ser Cys Ser Asn Arg Leu Val Gln His Gly Arg Gln Val Pro
            260                 265                 270

Leu Val Leu Phe Lys Thr Ala Asn Gly Ser Gly Trp Gly Val Arg Ala
        275                 280                 285

Ala Thr Ala Leu Arg Lys Gly Glu Phe Val Cys Glu Tyr Ile Glu Glu
290                 295                 300

Ile Ile Thr Ser Asp Glu Ala Asn Glu Arg Gly Lys Ala Tyr Asp Asp
305                 310                 315                 320

Asn Gly Arg Thr Tyr Leu Phe Asp Leu Asp Tyr Asn Thr Ala Gln Asp
                325                 330                 335

Ser Glu Tyr Thr Ile Asp Ala Ala Asn Tyr Gly Asn Ile Ser His Phe
            340                 345                 350

Ile Asn His Ser Cys Asp Pro Asn Leu Ala Val Phe Pro Cys Trp Ile
        355                 360                 365

Glu His Leu Asn Val Ala Leu Pro His Leu Val Phe Phe Thr Leu Arg
370                 375                 380

Pro Ile Lys Ala Gly Glu Glu Leu Ser Phe Asp Tyr Ile Arg Ala Asp
385                 390                 395                 400

Asn Glu Asp Val Pro Tyr Glu Asn Leu Ser Thr Ala Val Arg Val Glu
                405                 410                 415

Cys Arg Cys Gly Arg Asp Asn Cys Arg Lys Val Leu Phe
            420                 425

<210> SEQ ID NO 17
<211> LENGTH: 166
<212> TYPE: PRT
<213> ORGANISM: Homo sapiens

<400> SEQUENCE: 17

Thr Ala Lys Met Gly Trp Gly Val Arg Ala Leu Gln Thr Ile Pro Gln
1               5                   10                  15

Gly Thr Phe Ile Cys Glu Tyr Val Gly Glu Leu Ile Ser Asp Ala Glu
            20                  25                  30

Ala Asp Val Arg Glu Asp Asp Ser Tyr Leu Phe Asp Leu Asp Asn Lys
        35                  40                  45

Asp Gly Glu Val Tyr Cys Ile Asp Ala Arg Tyr Tyr Gly Asn Ile Ser
    50                  55                  60

Arg Phe Ile Asn His Leu Cys Asp Pro Asn Ile Ile Pro Val Arg Val
65                  70                  75                  80

Phe Met Leu His Gln Asp Leu Arg Phe Pro Arg Ile Ala Phe Phe Ser
                85                  90                  95

Ser Arg Asp Ile Arg Thr Gly Glu Glu Leu Gly Phe Asp Tyr Gly Asp
            100                 105                 110

Arg Phe Trp Asp Ile Lys Ser Lys Tyr Phe Thr Cys Gln Cys Gly Ser
        115                 120                 125

Glu Lys Cys Lys His Ser Ala Glu Ala Ile Ala Leu Glu Gln Ser Arg
    130                 135                 140

Leu Ala Arg Leu Asp Pro His Pro Glu Leu Leu Pro Glu Leu Gly Ser
145                 150                 155                 160

Leu Pro Pro Val Asn Thr
                165

<210> SEQ ID NO 18
```

```
<211> LENGTH: 139
<212> TYPE: PRT
<213> ORGANISM: Homo sapiens

<400> SEQUENCE: 18

Thr Gln Asn Lys Gly Trp Gly Ile Arg Cys Leu Asp Asp Ile Ala Lys
1               5                   10                  15

Gly Ser Phe Val Cys Ile Tyr Ala Gly Lys Ile Leu Thr Asp Asp Phe
            20                  25                  30

Ala Asp Lys Glu Gly Leu Glu Met Gly Asp Glu Tyr Phe Ala Asn Leu
        35                  40                  45

Asp His Ile Glu Ser Val Glu Tyr Ile Ile Asp Ala Lys Leu Glu Gly
    50                  55                  60

Asn Leu Gly Arg Tyr Leu Asn His Ser Cys Ser Pro Asn Leu Phe Val
65                  70                  75                  80

Gln Asn Val Phe Val Asp Thr His Asp Leu Arg Phe Pro Trp Val Ala
                85                  90                  95

Phe Phe Ala Ser Lys Arg Ile Arg Ala Gly Thr Glu Leu Thr Trp Asp
            100                 105                 110

Tyr Asn Tyr Glu Val Gly Ser Val Glu Gly Lys Glu Leu Leu Cys Cys
        115                 120                 125

Cys Gly Ala Ile Glu Cys Arg Gly Arg Leu Leu
    130                 135

<210> SEQ ID NO 19
<211> LENGTH: 20
<212> TYPE: PRT
<213> ORGANISM: Homo sapiens

<400> SEQUENCE: 19

Ala Arg Thr Lys Gln Thr Ala Arg Lys Ser Thr Gly Gly Lys Ala Pro
1               5                   10                  15

Arg Lys Gln Leu
            20

<210> SEQ ID NO 20
<211> LENGTH: 20
<212> TYPE: PRT
<213> ORGANISM: Homo sapiens

<400> SEQUENCE: 20

Met Gly Pro Arg Arg Arg Ser Arg Lys Pro Glu Ala Pro Arg Arg Arg
1               5                   10                  15

Ser Pro Ser Pro
            20

<210> SEQ ID NO 21
<211> LENGTH: 20
<212> TYPE: PRT
<213> ORGANISM: Rattus sp.

<400> SEQUENCE: 21

Met Ser Ser Arg Gly Gly Lys Lys Lys Ser Thr Lys Thr Ser Arg Ser
1               5                   10                  15

Ala Lys Ala Gly
            20
```